(12) United States Patent
Long et al.

(10) Patent No.: US 10,058,855 B2
(45) Date of Patent: Aug. 28, 2018

(54) REDOX-ACTIVE METAL-ORGANIC FRAMEWORKS FOR THE CATALYTIC OXIDATION OF HYDROCARBONS

(71) Applicant: The Regents of the University of California, Oakland, CA (US)

(72) Inventors: Jeffrey R. Long, Oakland, CA (US); Dianne J. Xiao, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 77 days.

(21) Appl. No.: 15/153,997

(22) Filed: May 13, 2016

(65) Prior Publication Data

US 2016/0332948 A1 Nov. 17, 2016

Related U.S. Application Data

(60) Provisional application No. 62/161,374, filed on May 14, 2015.

(51) Int. Cl.
| | |
|---|---|
| *B01J 31/16* | (2006.01) |
| *C07C 29/48* | (2006.01) |
| *C07C 65/05* | (2006.01) |
| *C07C 45/28* | (2006.01) |
| *C07C 45/33* | (2006.01) |
| *B01J 31/22* | (2006.01) |

(52) U.S. Cl.
CPC ....... *B01J 31/1691* (2013.01); *B01J 31/2239* (2013.01); *C07C 29/48* (2013.01); *C07C 45/28* (2013.01); *C07C 45/33* (2013.01); *C07C 65/05* (2013.01); *B01J 2231/70* (2013.01); *B01J 2531/22* (2013.01); *B01J 2531/26* (2013.01); *B01J 2531/842* (2013.01)

(58) Field of Classification Search
CPC . B01J 31/1691; B01J 31/2239; B01J 2231/70
See application file for complete search history.

(56) References Cited

U.S. PATENT DOCUMENTS

| | | | |
|---|---|---|---|
| 2,684,967 A | 7/1954 | Berg | |
| 4,532,225 A | 7/1985 | Tsao | |
| 5,064,804 A | 11/1991 | Soo | |
| 5,160,500 A | 11/1992 | Chu | |
| 5,208,335 A | 5/1993 | Ramprasad | |
| 5,648,508 A | 7/1997 | Yaghi | |
| 5,733,505 A | 3/1998 | Goldstein | |
| 5,779,904 A | 7/1998 | Ruderman | |
| 6,479,447 B2 | 11/2002 | Bijl | |
| 6,501,000 B1 | 12/2002 | Stibrany | |
| 6,617,467 B1 | 9/2003 | Mueller | |
| 6,624,318 B1 | 9/2003 | Mueller | |
| 6,686,428 B2 | 2/2004 | Zhang | |
| 6,893,564 B2 | 5/2005 | Mueller | |
| 6,929,679 B2 | 8/2005 | Mueller | |
| 6,930,193 B2 | 8/2005 | Yaghi | |
| 7,196,210 B2 | 3/2007 | Yaghi | |
| 7,202,385 B2 | 4/2007 | Mueller | |
| 7,229,943 B2 | 6/2007 | Gibson | |
| 7,279,517 B2 | 10/2007 | Mueller | |
| 7,309,380 B2 | 12/2007 | Mueller | |
| 7,343,747 B2 | 3/2008 | Mueller | |
| 7,411,081 B2 * | 8/2008 | Mueller | .................. C07F 3/003 556/118 |
| 7,524,444 B2 | 4/2009 | Hesse | |
| 7,582,798 B2 | 9/2009 | Yaghi | |
| 7,637,983 B1 | 12/2009 | Liu | |
| 7,815,716 B2 | 10/2010 | Mueller | |
| 8,343,260 B2 | 1/2013 | Omary | |
| 8,480,955 B2 | 7/2013 | Yaghi | |
| 8,501,150 B2 | 8/2013 | Schubert | |
| 8,518,264 B2 | 8/2013 | Kiener | |
| 8,524,932 B2 | 9/2013 | Leung | |
| 8,709,134 B2 | 4/2014 | Yaghi | |
| 8,735,161 B2 | 5/2014 | Yaghi | |
| 8,742,152 B2 | 6/2014 | Yaghi | |
| 9,078,922 B2 | 7/2015 | Yaghi | |
| 2003/0004364 A1 | 1/2003 | Yaghi | |
| 2003/0078311 A1 | 4/2003 | Muller | |
| 2003/0148165 A1 | 8/2003 | Muller | |
| 2003/0222023 A1 | 12/2003 | Mueller | |
| 2004/0081611 A1 | 4/2004 | Muller | |
| 2004/0225134 A1 | 11/2004 | Yaghi | |

(Continued)

FOREIGN PATENT DOCUMENTS

| | | |
|---|---|---|
| CN | 1910191 A | 2/2007 |
| CN | 101270094 A | 9/2008 |

(Continued)

OTHER PUBLICATIONS

Nicola (Inorganic Chemistry, 46 (1), 2007).*
Du et al., "Direction of unusual mixed-ligand metal-organic frameworks: a new type of 3-D polythreading involving 1-D and 2-D structural motifs and a 2-fold interpenetrating porous network", Chem. Commun., 2005, 5521-5523.
Dugan et al., 'Covalent modification of a metal-organic framework with isocyanates: probing substrate scope and reactivity,' 29:3366-3368 (2008).
Eddaoudi, M et al., "Systematic Design of Pore Size and Functionality in Isoreticular MOFs and Their application in Methane Storage" Science, (2002), vol. 295, pp. 469-472.
Forster et al., 'A High-Throughput Investigation of the Role of pH, Temperature, Concentration, and Time on the Synthesis of Hybrid Inorganic-Organic Materials,' Angew. Chemie Int. Ed. 44(46):7608-7611 (2005).

(Continued)

*Primary Examiner* — Pancham Bakshi
(74) *Attorney, Agent, or Firm* — Gavrilovich, Dodd & Lindsey LLP

(57) ABSTRACT

The disclosure provides for metal organic frameworks (MOFs) which comprise a plurality of redox-active metals or metal ions that are linked together by a plurality of dioxide-benzenedicarboxylate-based organic linking ligands. The disclosure further provides for the use of these MOFs in variety of applications, including catalyzing the oxidization of various hydrocarbons to higher oxidation states.

17 Claims, 17 Drawing Sheets

(56) References Cited

U.S. PATENT DOCUMENTS

| | | |
|---|---|---|
| 2004/0249189 A1 | 12/2004 | Mueller |
| 2004/0265670 A1 | 12/2004 | Muller |
| 2005/0004404 A1 | 1/2005 | Muller |
| 2005/0014371 A1 | 1/2005 | Tsapatsis |
| 2005/0124819 A1 | 6/2005 | Yaghi |
| 2005/0154222 A1 | 7/2005 | Muller |
| 2005/0192175 A1 | 9/2005 | Yaghi |
| 2006/0057057 A1 | 3/2006 | Muller |
| 2006/0135824 A1 | 6/2006 | Mueller |
| 2006/0154807 A1 | 7/2006 | Yaghi |
| 2006/0185388 A1 | 8/2006 | Muller |
| 2006/0252641 A1 | 11/2006 | Yaghi |
| 2006/0252972 A1 | 11/2006 | Pilliod |
| 2006/0287190 A1 | 12/2006 | Eddaoudi |
| 2007/0068389 A1 | 3/2007 | Yaghi |
| 2007/0202038 A1 | 8/2007 | Yaghi |
| 2007/0217982 A1 | 9/2007 | Wright |
| 2007/0248575 A1 | 10/2007 | Connor |
| 2008/0017036 A1 | 1/2008 | Schultink |
| 2008/0190289 A1 | 8/2008 | Muller |
| 2009/0155588 A1 | 6/2009 | Hesse |
| 2009/0183996 A1 | 7/2009 | Richter |
| 2009/0216059 A1 | 8/2009 | Reyes |
| 2009/0247654 A1 | 10/2009 | Rajendran |
| 2010/0069234 A1 | 3/2010 | Willis |
| 2010/0258004 A1 | 10/2010 | Matzger et al. |
| 2011/0015388 A1 | 1/2011 | Youngblood |
| 2011/0282067 A1 | 11/2011 | Li |
| 2011/0282071 A1 | 11/2011 | Shi |
| 2012/0028846 A1 | 2/2012 | Yaghi |
| 2012/0031268 A1 | 2/2012 | Yaghi |
| 2012/0130113 A1 | 5/2012 | Yaghi |
| 2012/0133939 A1 | 5/2012 | Yaghi |
| 2013/0047849 A1 | 2/2013 | Zhang |
| 2013/0096210 A1 | 4/2013 | Yaghi |
| 2014/0037944 A1 | 2/2014 | Dichtel |
| 2014/0148596 A1 | 5/2014 | Dichtel |
| 2016/0159713 A1 | 6/2016 | Long |
| 2016/0250618 A1 | 9/2016 | Long |

FOREIGN PATENT DOCUMENTS

| | | |
|---|---|---|
| DE | 102005023856 A1 | 11/2006 |
| DE | 102005054523 A1 | 5/2007 |
| EP | 1070538 A2 | 1/2001 |
| JP | 2007534658 A | 11/2007 |
| KR | 20100055350 A | 5/2010 |
| WO | 9905151 A1 | 2/1999 |
| WO | 2006110740 A2 | 10/2006 |
| WO | 2006122920 A1 | 11/2006 |
| WO | 2006125761 A2 | 11/2006 |
| WO | 2007007113 A2 | 1/2007 |
| WO | 2007118843 A1 | 10/2007 |
| WO | 2009073739 A1 | 6/2009 |
| WO | 2010056092 A2 | 5/2010 |
| WO | 2010080618 A2 | 7/2010 |
| WO | 2010083418 A1 | 7/2010 |
| WO | 2011127301 A2 | 10/2011 |
| WO | 2011146155 A2 | 11/2011 |
| WO | 2012012495 A2 | 1/2012 |
| WO | 2012082213 A2 | 6/2012 |
| WO | 2012100224 A2 | 7/2012 |
| WO | 2012106451 A2 | 8/2012 |

OTHER PUBLICATIONS

Fracaroli et al., 'Isomers of Metal-Organic Complex Arrays,' Inorg. Chem. 51: 6437-6439 (Jun. 5, 2012).

Fracaroli, A.M. et al., Metal-Organic Frameworks with Precisely Designed Interior for Carbon Dioxide Capture in the Presence of Water, J. Am. Chem. Soc, Jun. 25, 2014, vol. 136, No. 25, pp. 8863-8866.

Furukawa et al., 'Isoreticular Expansion of MetalOrganic Frameworks with Triangular and Square Building Units and the Lowest Calculated Density for Porous Crystals,' Inorg. Chem. 50:9147-9152 (2011).

Furukawa et al., 'Storage of Hydrogen, Methane, and Carbon Dioxide in Highly Porous Covalent Organic Frameworks for Clean Energy Applications,' J. Am. Chem. Soc. 25:8876-8883 (2009).

Furukawa et al., "Water Adsorption in Porous Metal-Organic Frameworks and Related Materials," J. of the Amer. Chem. Soc, vol. 136, No. 11, pp. 4369-4381, Published: Mar. 3, 2014.

Gadzikwa, T. et al., 'Selective Bifunctional Modification of a Non-catenated Metal-Organic Framework Material via Click Chemistry,' J. Am. Chem. Soc. 131:13613-13615 (2009).

Galli et al., 'Adsorption of Harmful Organic Vapors by Flexible Hydrophobic Bis-pyrazolate Based MOFs,' Chem. Mater. 22(5):1664-1672 (2010).

Gandara et al., 'High Methane Storage Capacity in Aluminum Metal-Organic Frameworks', Journal of the American Chemical Society, vol. 136, No. 14, Mar. 21, 2014, pp. 5271-5274.

Gandara et al., 'Porous, Conductive Metal-Triazolates and Their Structural Elucidation by the Charge-Flipping Method,' Chem. Eur. J. 18:10595-10601 (2012).

Gandara, Felipe, et al., "Crystallography of metal-organic frameworks", IUCRJ, vol. 1, No. 6, Oct. 28, 2014, pp. 563-570.

Garibay et al., "Isoreticular synthesis and modification of frameworks with the UiO-66 topology," Chemical Communications, 46:7700-7702, Sep. 27, 2010.

Gassenmith et al., 'Strong and Reversible Binding of Carbon Dioxide in a Green Metal-Organic Framework,' J. Am. Chem. Soc. 133:15312-15315 (Aug. 30, 2011).

Gonzalez-Arellano et al., 'Homogeneous and heterogeneous Au(III) Schiff base-complexes as selective and general catalysts for self-coupling of aryl boronic acids,' Chem. Comm. 15:1990-1992 (2005).

Goto, Y et al., "Clickable Metal-Organic Framework," J. Am. Chem. Soc. 130:14354-14355 (2008).

Han et al., 'Covalent Organic Frameworks as Exceptional Hydrogen Storage Materials,' J. Am. Chem. Soc. 130:11580-11581 (2008).

Kirai et al., 'Homocoupling of arylboronic acids catalyzed by 1,10-phenanthroline—ligated copper complexes in air,' European Journal of Organic Chemistry 12:1864-1867 (2009).

Akporiaye et al., 'Combinatorial Approach to the Hydrothermal Synthesis of Zeolites,' Angew. Chemie 37(5):609-611 (1998).

Barman et al., 'Incorporation of active metal sites in MOFs via in situ generated ligand deficient metal-linker complexes' Chem. Commun. 47:11882-11884 (Oct. 11, 2011).

Bhakta et al., 'Metal organic frameworks as templates for nanoscale NaAlH4', Journal of American Chemical Society, vol. 131, No. 37, Sep. 23, 2009, pp. S1-S14.

Britt et al., "Metal-Organic frameworks with high capacity and selectivity for harmful gases", PNAS, 2008, vol. 105, No. 33, pp. 11623-11627.

Burrows, Andrew D., 'Mixed-component metal-organic frameworks (MC-MOFs): enhancing functionality through solid solution formation and surface modifications', Crystengcomm, vol. 13, No. 11, Jan. 1, 2011, pp. 3623-3642.

Burrows, Andrew D., et al., "Post-Synthetic Modification of Tagged MOFs", Angewa. Chem. Int . Ed., (Oct. 20, 2008), vol. 47, pp. 8482-8486, XP008150669.

Carboni et al., "Highly porous and stable metal-organic frameworks for uranium extraction," Chemical Science, 4:2396-2402, Apr. 4, 2013.

Carlucci et al., 'Nanoporous three-dimensional networks topologically related to cooperite from the self-assembly of copper(I)centres and 1,2,4,5-tetracyanobenzene,' New J. Chem. 23(23):397-401 (1999).

Chen et al. "Photoluminescent Metal-Organic Polymer Constructed from Trimetallic Clusters and Mixed Carboxylates", Inorg. Chem. 2003, 42, 944-946.

Chen et al., 'Noncovalently Netted, Photoconductive Sheets with Extremely High Carrier Mobility and Conduction Anisotropy from Triphenylene-Fused Meetal Trigon Conjugates,' In. J. Am. Chem. Soc. 131:7287-7297 (2009).

Chen, Binling, et. al., "Zeolitic imidazolate framework materials: recent progress in synthesis and applications", Journal of Materials

(56) References Cited

OTHER PUBLICATIONS

Chemistry A: Materials for Energy and Sustainability, GB, (Jul. 17, 2014), vol. 2, No. 40, doi:10.1039/C4TA02984D, ISSN 2050-7488, pp. 16811-16831, XP055337959.
Choi et al., 'Reversible Interpenetration in a Metal-Organic Framework Triggered by Ligand Removal and Addition,' Angew. Chem. Int. Ed. 51:8791 -8795 (2012).
Chun et al., 'Concomitant Formation of N-Heterocyclic Carbene-Copper Comlexies within a Supramolecular Network in the Self-Assembly of Immidzolium Dicarboxylate with Metal Ions,' Inorganic Chemistry, Jul. 20, 2009, pp. 6353-6355, vol. 48, No. 14.
Chun et al., 'Cu2O: A versatile Reagent for Base-Free Direct Synthesis of NHC-Copper Complexes and Decoration of 3D-MOF with Coordinatively Unsaturated NHC-Copper Species,' Organometallics, Mar. 16, 2010, pp. 1518-1521, vol. 29, No. 7.
Corma et al., 'A large-cavity zeolite with wide pore windows and potential as an oil refining catalyst,' Nature, vol. 418, pp. 514-517 (Aug. 2002).
Corma et al., "From MOFs to zeolites: zirconium sites for epoxide rearrangement," New J. of Chem. 37:3496-3502, Aug. 2, 2013.
Coskun et al., 'Metal-Organic Frameworks Incorporating Copper-Complexed Rotaxanes,' Angew. Chem. Int. Ed., 51:2160-2163 (2012).
Costa et al., 'Chemical Modification of a Bridging Ligand Inside a Metal-Organic Framework while Maintaining the 3D Structure,' Eur. J. Inorg. Chem. 10:1539-1545 (2008).
Cote et al., 'Porous, Crystalline, Covalent Organic Frameworks,' Science 310:1166-1170 (2005).
Cote et al., 'Reticular Synthesis of Microporous and Mesoporous 2D Covalent Organic Frameworks,' J. Am. Chem. Soc. 129:12914-12915 (2007).
Crees et al., 'Synthesis of a Zinc(II) Imidazolium Dicarboxylate Logand Metal-Organic Framework (MOF): a Potential Precursor to MOF-Tethered N-Heterocyclic Carbene Compounds,' Inorganic Chemistry, Jan. 19, 2010, vol. 49, No. 4, pp. 1712-1719.
Cui et al., 'In Situ Hydrothermal Growth of Metal-Organic Framework 199 Films on Stainless Steel Fibers for Solid-Phase Microextraction of Gaseous Benzene Homologues,' Anal. Chem. 81(23):9771-9777 (2009).
Demessence, A et al., 'Strong CO2 Bnding in a Water-Stable, Triazolate-Bridged Metal-Organic Framework Functionalized with Ethylenediamine,' J. Am. Chem. Soc. 131:8784-8786 (2009).
Demir et al., 'Role of Copper Species in the Oxidative Dimerization of Arylboronic Acids: Synthesis of Symmetrical Biaryls,' Journal of Organic Chemistry 68(26):10130-10134 (2003).
Deng et al., 'Large-Pore Apertures in a Series of Metal-Organic Frameworks,' Science 336:1018-1023 (May 25, 2012).
Deng, H. et al., "Large-Pore Apertures in a Series of Metal-Organic Frameworks," Science, vol. 336, No. 6084, May 12, 2012, pp. 1018-1023.
Deska, Malgorzata, "Donor-acceptor rotaxanes with tetracationic cyclophane ring", ARKIVOC, 2013, i, 185-242.
Deska, Malgorzata, "Rotaxanes and pseudorotaxanes with threads containing viologen units", ARKIVOC, 2013, i, 66-100.
Dhakshinamoorthy et al., "Metal-organic frameworks as heterogeneous catalysts for oxidation reactions", Catal. Sci. Technol., Apr. 28, 2011, 1, 856-867.
Dietzel, Pascal D. C., et. al., "Application of metal-organic frameworks with coordinatively unsaturated metal sites in storage and separation of methane and carbon dioxide", Journal of Materials Chemistry, (Aug. 21, 2009), vol. 19, No. 39, doi:10.1039/b911242a, ISSN 0959-9428, pp. 7362-7370, XP055197279.
Song et al., 'A Multiunit Catalyst with Synergistic Stability and Reactivity: A PolyoxometalateMetal Organic Framework for Aerobic Decontamination,' J. Am. Chem. Soc. 133(42):16839-16846 (Sep. 13, 2011).
Szeto et al., "A Thermally Stable Pt/Y-Based Metal-Organic Framework: Exploring the Accessibility of the Metal Centers with Spectroscopic Methods Using H2O, CH3OH, and CH3CN as Probes", J. Phys. Chem. B, 2006, 110, 21509-21520.

Szeto et al., "Characterization of a New Porous Pt-Containing Metal-Organic Framework Containing Potentially Catalytically Active Sites: Local Electronic Structure at the Metal Centers", Chem. Mater., 2007, 19, 211-220.
Tanabe et al., 'Systematic Functionalization of a Metal-Organic Framework via a Postsynthetic Modification Approach,' J. Am. Chem. Soc. 130(26):8508-8517 (2008).
Tilford et al., 'Facile Synthesis of a Highly Crystalline, Covalently Porous Boronate Network,' 18(22):5296-5301 (Oct. 11, 2006).
Tranchemontagne et al., 'Hydrogen Storage in New Metal-Organic Frameworks,' J. Phys. Chem. C 116(24):13143-13151 (May 24, 2012).
Vitillo et al., 'Role of Exposed Metal Sites in Hydrogen Storage in MOFs,' J. Am. Chem. Soc. 130(26):8386-8396 (2008).
Wang, Zhenqiang, et al., 'Postsynthetic Covalent Modification of a Neutral Metal—Organic Framework', J. Am. Chem. Soc., (2007), vol. 129, No. 41, pp. 12368-12369.
Whitfield et al. Metal-organic frameworks based on iron oxide octahedral chains connected by benzendicarboxylate dianions. Solid State Sciences, 2005. vol. 7, pp. 1096-1103.
Yaghi et al., "Preparation of Single Crystals of Coordination Solids in Silica Gels: Synthesis and Structure of CuII (1,4-C4H4N2)(C4O4)(OH2)4", Journal of Solid State Chemistry, 117, 256-260 (1995).
Yang et al., 'CH4 storage and CO2 capture in highly porous zirconium oxide based metal-organic frameworks,' Chem. Commun., 48:9831-9833, Aug. 15, 2012.
Yang et al., 'Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties,' Crystal Growth Design 7(10):2009-2015 (2007).
Zhenqiang Wang et al., 'Tandem Modification of Metal-Organic Frameworks by a Postsynthetic Approach', Angew Chem Int Ed, (200800686), vol. 47, pp. 4699-4702.
Zhou et al., 'Introduction to Metal-Organic Frameworks,' Chemical Reviews 112:673-674 (Jan. 26, 2012).
Zou et al., "Novel Eclipsed 2D Cadmium(II) Coordination Polymers with Open-Channel Structure Constructed from Terephthalate and 3-(2-Pyridyl)pyrazole: Crystal Structures, Emission Properties, and Inclusion of Guest Molecules", Inorg. Chem. 2004, 43, 5382-5386.
Koh et al., 'A Crystalline Mesoporous Coordination Copolymer with High Microporosity,' Angew Chem Int'l, 2008, pp. 677-680, vol. 47.
Koh et al., "A Crystalline Mesoporous Coordination Copolymer with High Microporosity", Angew. Chem. Int. Ed. 2008, 120, pp. 689-692.
Kong et al., 'Mapping of Functional Groups in Metal-Organic Frameworks', Science, vol. 341, No. 6148, Jul. 25, 2013, pp. 882-885.
Koza et al., 'An efficient High Yielding Approach for the Homocoupling of Aryl Boronic Acids,' Synthesis 15:2183-2186 (2002).
Kyoungmoo et al., "A Crystalline Mesoporous Coordination Copolymer with High Microporosity," Angew. Chem. Int. Ed. 47(4):689-92 (2008).
Ling et al., 'A zinc(II) metal-organic framework based on triazole and dicarboxylate ligands for selective adsorption of hexane isomers,' Chem. Comm. 47:7197-7199 (2011).
Luo et al., 'Two new metal-triazole-benzenedicarboxylate frameworks affording an uncommon 3,4-connected net and unique 4,6-connected rod packing: hydrothermal synthesis, structure, thermostability and luminescence studies,' CrystEngComm 11 (6): 1097-1102 (2009).
Mason, Jarad A., "Evaluating metal-organic frameworks for natural gas storage", Chemical Science, vol. 5, Accepted Oct. 22, 2013, pp. 32-51.
McDonald, Thomas M. et al., 'Capture of Carbon Dioxide from Air and Flue Gas in the Alkylamine-Appended Metal-Organic Framework mmen-Mg 2 (dobpdc)', Journal of the American Chemical Society, vol. 134, No. 16, Apr. 4, 2012, pp. 7056-7065.

(56) References Cited

OTHER PUBLICATIONS

Mendoza-Cortes et al., 'Adsorption Mechanism and Uptake of Methane in Covalent Organic Frameworks: Theory and Experiment,' J. Phys. Chem. 114:10824-10833 (2010).
Morris et al., 'Framework mobility in the metal-organic framework crystal IRMOF-3: Evidence for aromatic ring and amine rotation,' Journal of Molecular Structure 1004:94-101 (2011).
Morris et al., 'Synthesis, Structure, and Metalation of Two New Highly Porous Zirconium Metal-Organic Frameworks,' Inorg. Chem. 51:6443-6445 (Jun. 7, 2012).
O'Keeffe et al., 'Deconstructing the Crystal Structures of Metal-Organic Frameworks and Related Materials into Their Underlying Nets,' Chem. Rev. 112(2):675-702 (Feb. 8, 2012).
Oisaki et al., "A Metal-Organic Framework with Covalently Bound Organometallic Complexes," J. of the Amer. Chem. Soc., pp. 9262-9264, vol. 132, No. 27, 2010.

\* cited by examiner dobdc$^{4-}$ m-dobdc$^{4-}$

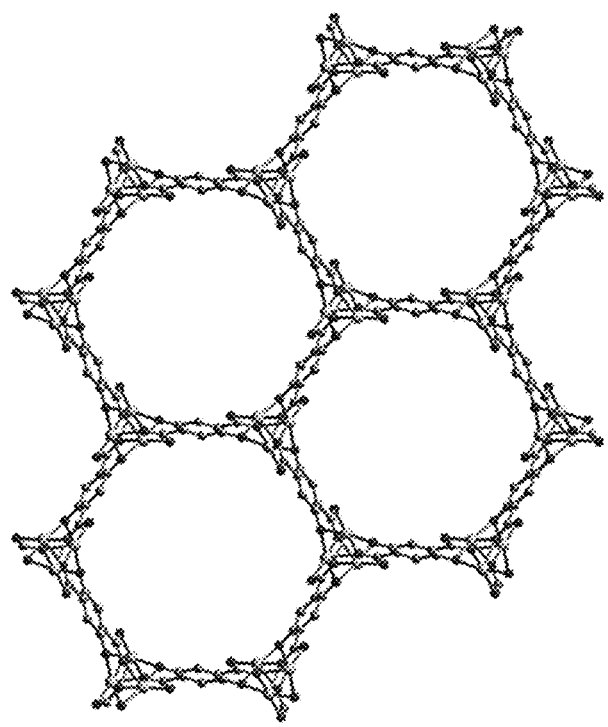
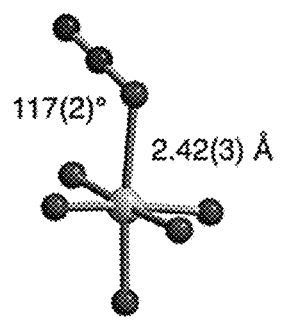
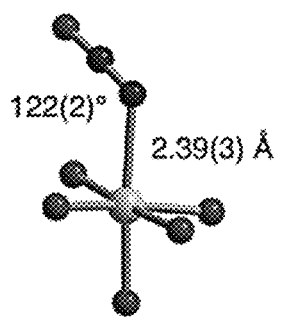
FIG. 3A
FIG. 3B

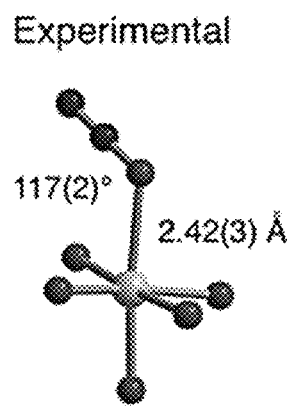
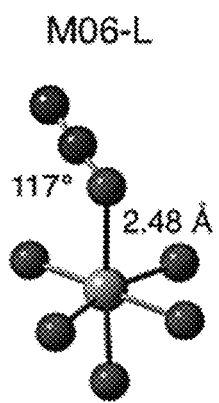
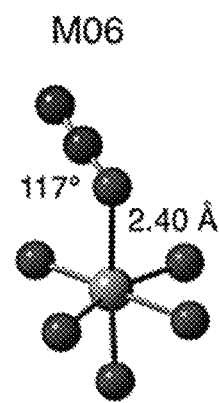
*FIG. 4A*
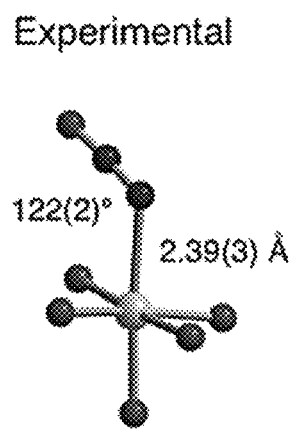
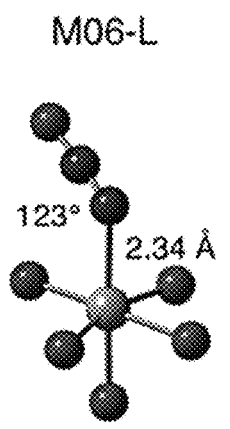
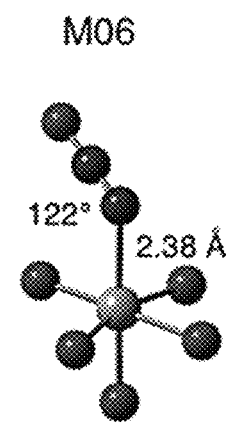
*FIG. 4B*
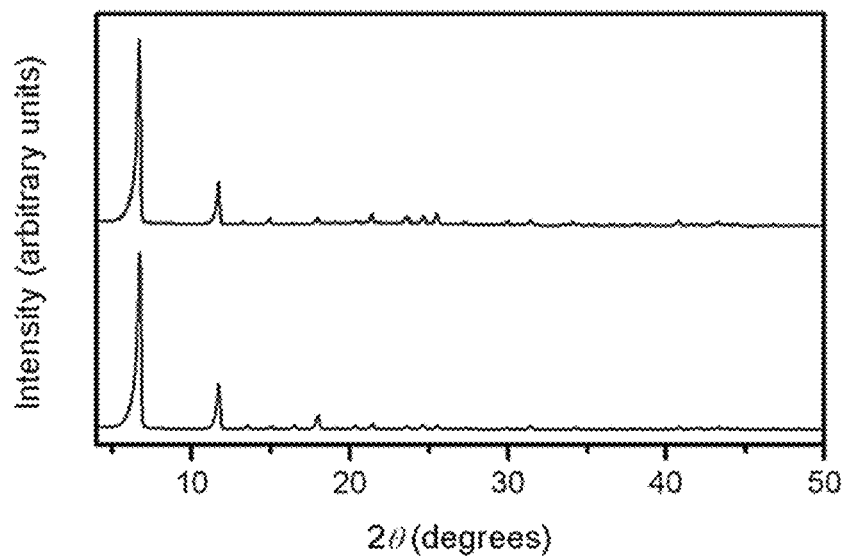
*FIG. 5*

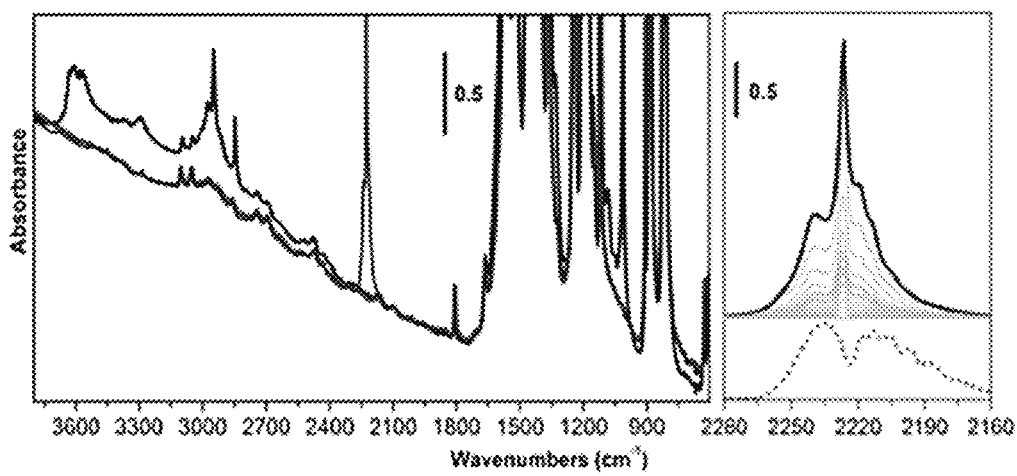
FIG. 15A          FIG. 15B
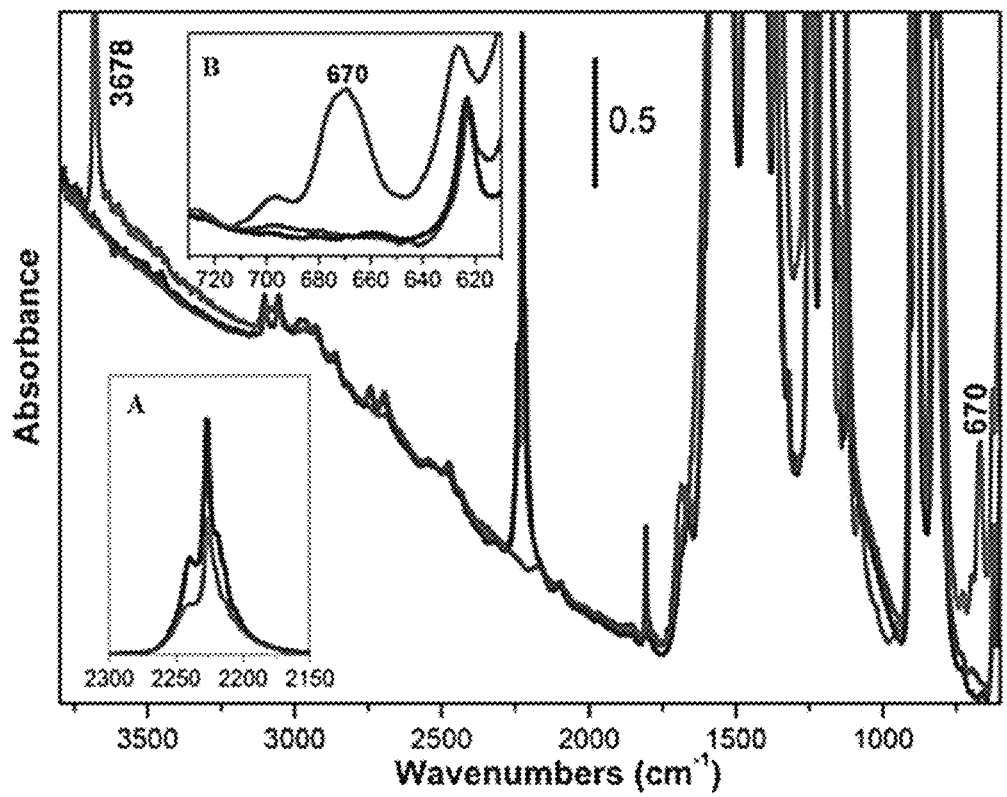
FIG. 16A-B

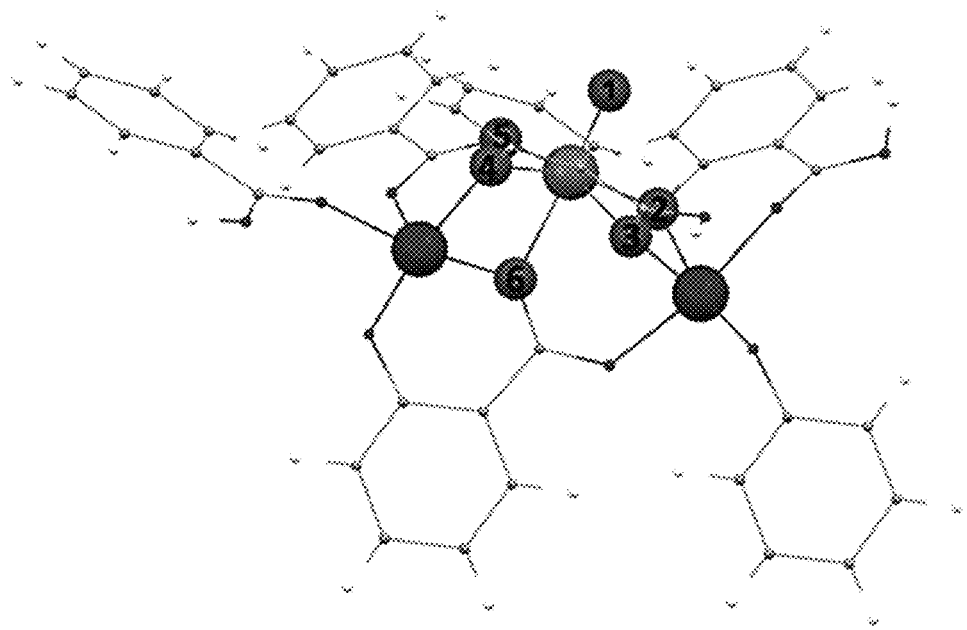
*FIG. 27*
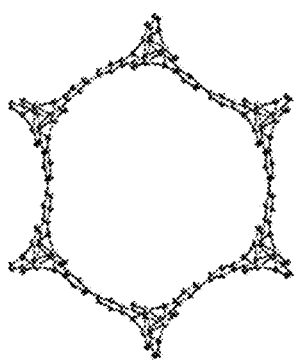 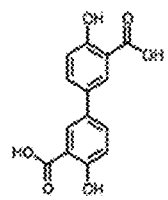 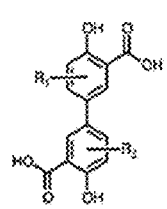 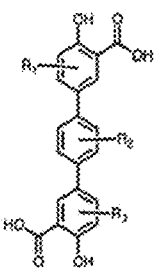
*FIG. 28A*  *FIG. 28B*  *FIG. 28C*  *FIG. 28D*

REDOX-ACTIVE METAL-ORGANIC FRAMEWORKS FOR THE CATALYTIC OXIDATION OF HYDROCARBONS

CROSS REFERENCE TO RELATED APPLICATIONS

This application claims priority under 35 U.S.C. § 119 from Provisional Application Ser. No. 62/161,374, filed May 14, 2015, the disclosure of which is incorporated herein by reference.

STATEMENT REGARDING FEDERALLY SPONSORED RESEARCH

This invention was made with government support under Grant No. DE-SC0008688 and Grant No. DE-AC02-05CH11231 awarded by the United States Department of Energy. The government has certain rights in the invention.

TECHNICAL FIELD

The disclosure provides for metal organic frameworks (MOFs) which comprise a plurality of redox-active metals or metal ions that are linked together by a plurality of dioxide-benzenedicarboxylate-based organic linking ligands. The disclosure further provides for the use of these MOFs in variety of applications, including catalyzing the oxidization of various hydrocarbons to higher oxidation states.

BACKGROUND

Metal-organic frameworks (MOFs) are porous crystalline materials that are constructed by linking metal clusters called Secondary Binding Units (SBUs) and organic linking ligands. MOFs have high surface area and high porosity which enable them to be utilized in diverse fields, such as gas storage, catalysis, and sensors.

The selective and efficient conversion of light alkanes into value-added chemicals remains an outstanding challenge with tremendous economic and environmental impact, especially considering the recent worldwide increase in natural gas reserves. In nature, C—H functionalization is carried out by copper and iron metalloenzymes, which activate dioxygen and, through metal-oxo intermediates, facilitate two- or four-electron oxidations of organic substrates.

SUMMARY

The disclosure three-dimensional metal-organic frameworks (MOFs) that comprise a plurality of redox active metals or metal ions connected by a plurality of 2,5-dioxido-1,4-benzenedicarboxylate (dobdc$^{4-}$) and/or 2,4-dioxido-15-benzenedicarboxylate (m-dobdc$^{4-}$) based organic linking ligands. The MOFs of the disclosure are stable to desolvation and comprise coordinatively-unsaturated redox active metal centers in a single, well-defined environment. In a particular embodiment, the disclosure provides for a Fe$_2$(dobdc) (1) based framework, which hexagonal pore channels of the framework are lined with a single type of square pyramidal iron(II) site (see FIG. 3A). The high density and redox-active nature of these open metal sites engender excellent O$_2$/N$_2$ and hydrocarbon separation properties. The disclosure demonstrates the reactivity of MOFs of the disclosure towards a gaseous two-electron oxidant and O-atom transfer agent (e.g., N$_2$O), generating a highly reactive iron(IV)-oxo species capable of oxidizing strong C—H bonds. In a further embodiment, the MOFs disclosed herein, catalyze the oxidation of light hydrocarbons (e.g., methane, ethane, and propane) into corresponding alcohols and/or aldehydes; catalyze the oxidation of cyclohexane into KA oil (i.e., a mixture of cyclohexanol and cyclohexanone); catalyze the oxidation of benzene to phenol; and catalyze the oxidation of alkenes to corresponding epoxides (e.g., propylene to propylene oxide, and ethylene to ethylene oxide).

The disclosure also provides that the MOFs of the disclosure may also be comprised of a plurality of redox-inactive metals or metal ions in addition to the redox-active metal or metal ions (i.e., mixed-metal MOFs). In a further embodiment, the mixed MOFs of the disclosure are highly selective catalysts which allow for the conversion of (C$_1$-C$_6$)-hydrocarbons to corresponding alcohols versus other oxidative products.

In a particular embodiment, the disclosure provides for a MOF that comprises a plurality of redox-active metals or metal ions connected by a plurality of organic linking ligands comprising the structure(s) selected from the group consisting of:

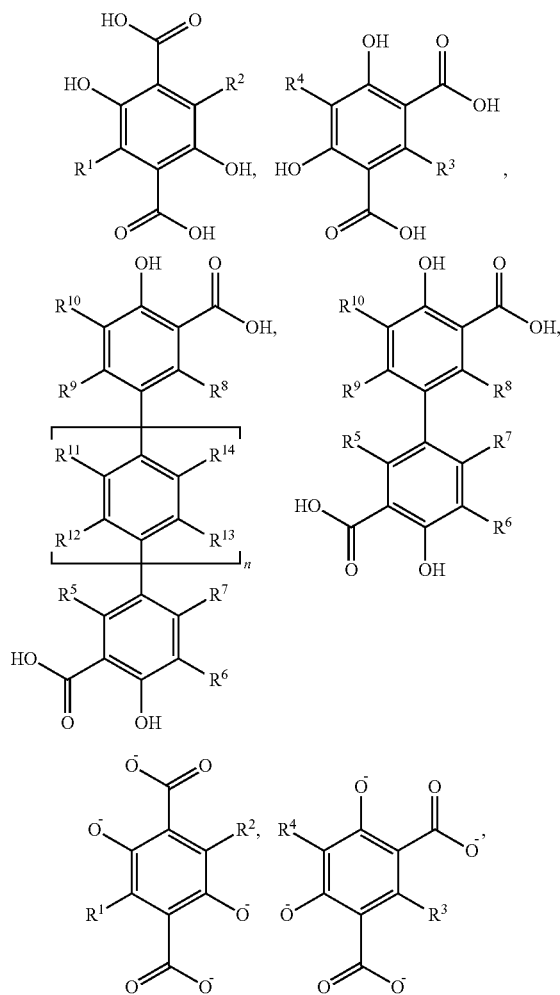

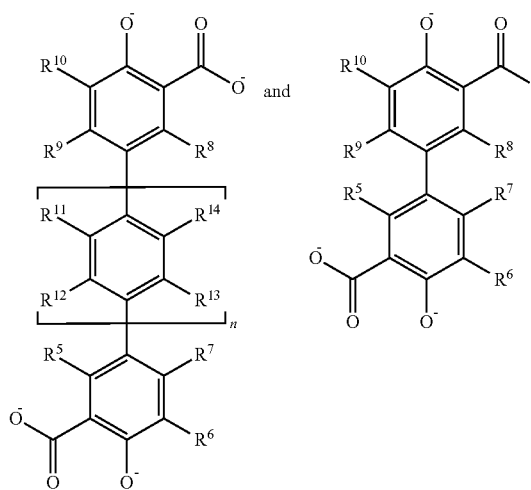

wherein $R^1$-$R^{14}$ are independently selected from H, D, optionally substituted FG, optionally substituted ($C_1$-$C_{20}$) alkyl, optionally substituted ($C_1$-$C_{19}$) heteroalkyl, optionally substituted ($C_1$-$C_{20}$)alkenyl, optionally substituted ($C_1$-$C_{19}$) heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system.

In one embodiment, the organic linking ligand comprises a structure selected from the group consisting of:

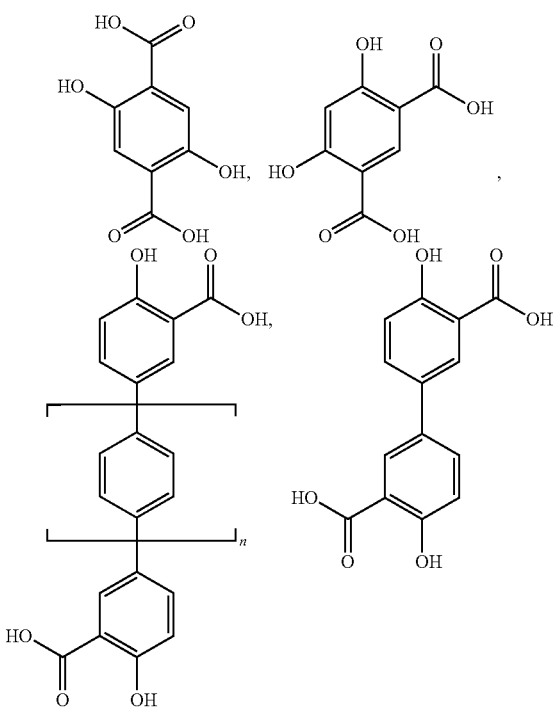

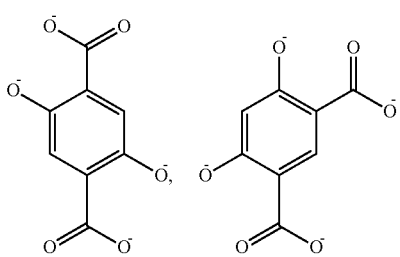

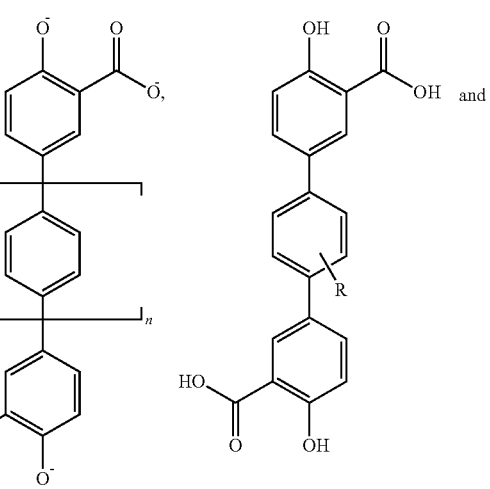

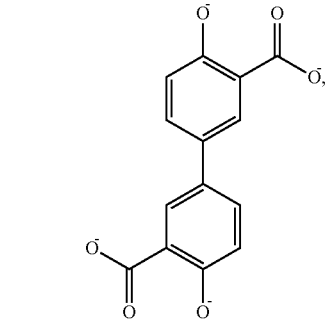

wherein

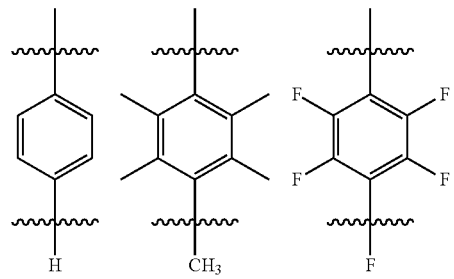

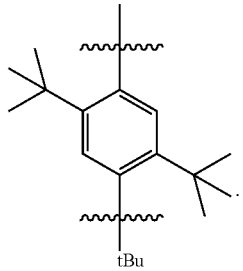

In a specific embodiment, the organic linking ligand is selected from:

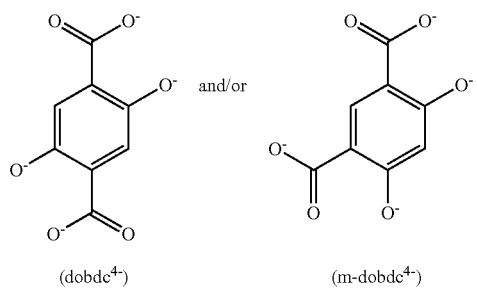 [SMILES: O=C([O-])c1cc([O-])c(C(=O)[O-])cc1[O-] ; O=C([O-])c1cc(C(=O)[O-])c([O-])cc1[O-]]

In all of the foregoing embodiments, the MOF is capable of catalytically oxidizing $(C_1-C_6)$-hydrocarbons to their corresponding alcohols, epoxides and/or aldehydes. In a further embodiment, the MOF comprises repeating units of a metal (e.g., $M^1$) linked through a carboxylate to the linking ligand. For example, in certain embodiment the MOF comprises repeating units of the formula $(M^1)_2$(dobdc) and/or of the formula $(M^1)_2$(m-dobdc), wherein $M^1$ is a redox-active metal or metal ion. In yet a further embodiment, the redox-active metal is selected from Fe, Mn, Co, Ni, and Cu, or a divalent cation of any of the foregoing.

In another embodiment, the disclosure also provides for a MOF that is a mixed metal MOF comprising a plurality of redox-active metals or metal ions and a plurality redox-inactive metals or metal ions that are connected by a plurality of organic linking ligands comprising the structure(s) selected from the group consisting of:

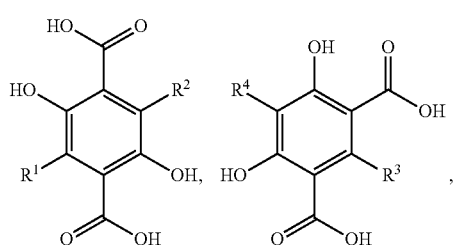

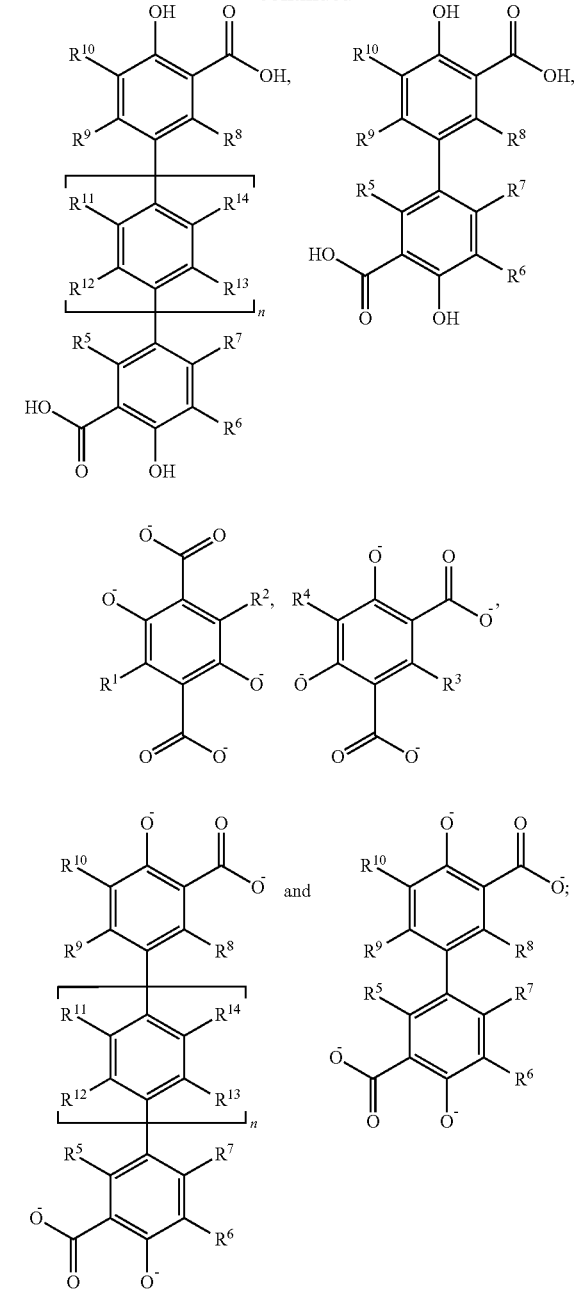

wherein $R^1$-$R^{14}$ are independently selected from H, D, optionally substituted FG, optionally substituted $(C_1-C_{20})$ alkyl, optionally substituted $(C_1-C_{19})$ heteroalkyl, optionally substituted $(C_1-C_{20})$alkenyl, optionally substituted $(C_1-C_{19})$ heteroalkenyl, optionally substituted $(C_1-C_{19})$alkynyl, optionally substituted $(C_1-C_{19})$heteroalkynyl, optionally substituted $(C_1-C_{19})$cycloalkyl, optionally substituted $(C_1-C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In one embodiment, the organic linking ligand comprises a structure selected from the group consisting of:

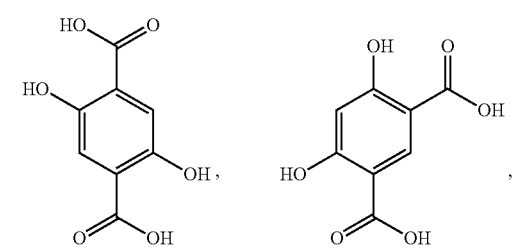

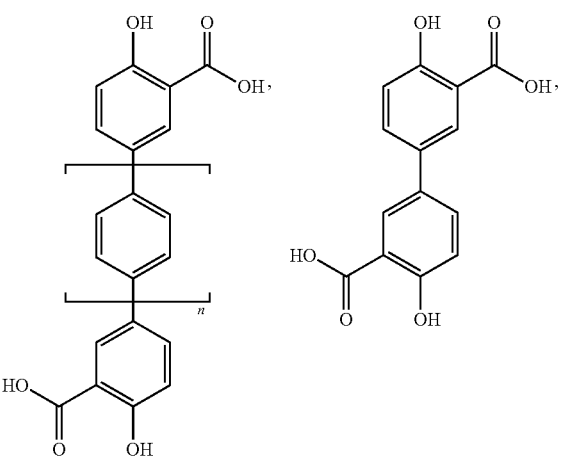

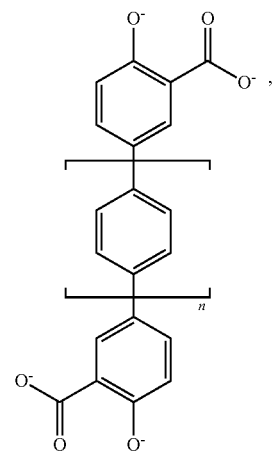

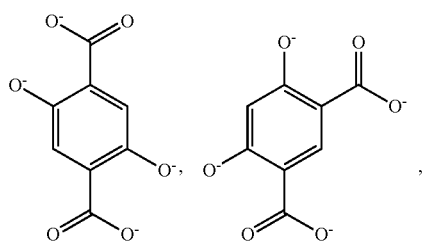

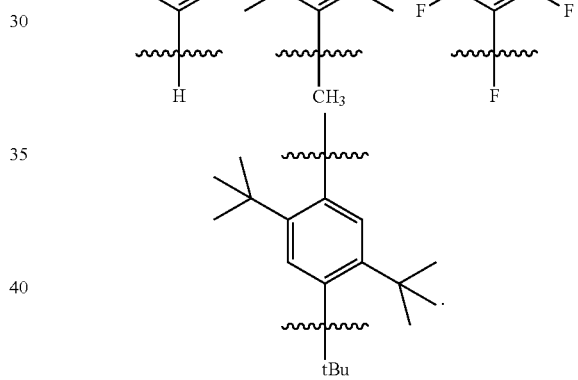

wherein:

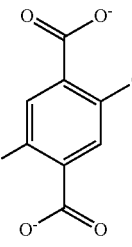

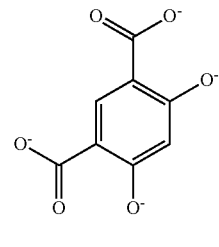

In a specific embodiment, the organic linking ligand is selected from:

(dobdc$^{4-}$)  (m-dobdc$^{4-}$)

wherein, the MOF is capable of catalytically oxidizing of small hydrocarbons to their corresponding alcohols and aldehydes. In a further embodiment, the plurality of redox-inactive metal ions is selected from Mg, Ca, Sr, Ba, Sc, Y, Ti, Zr, V, Nb, Ta, Cr, Mo, W, Re, Ru, Os, Rh, Ir, Pd, Pt, Ag, Au, Zn, Cd, Hg, Al, Ga, In, Si, Ge, Sn, Pb, As, Te, La, Ce, Pr, Nd, Sm, Eu, Gd, Tb, Db, Tm, Yb, and La, or a divalent cation of any of the foregoing.

In another embodiment, the disclosure further provides for a MOF that comprises repeating units of the formula $(M^1)(M^2)_{2-x}$(linking ligand) and/or of the formula $(M^1)_x(M^2)_{2-x}$(linking ligand), $(M^1)_x(M^2)_{2-x}$(dobdc) and/or of the formula $(M^1)_x(M^2)_{2-x}$(m-dobdc), wherein at least one of $M^1$-$M^2$ is a redox-active metal or metal ion, x is a number less than or equal to 1, 0.3, or 0.1. In yet another embodiment, $M^1$ is selected from Fe, Mn, Co, Ni, and Cu, or a divalent cation of any of the foregoing. In yet another embodiment, $M^2$ is selected from Mg, Ca, Sr, Ba, Sc, Y, Ti, Zr, V, Nb, Ta, Cr, Mo, W, Re, Ru, Os, Rh, Ir, Pd, Pt, Ag, Au, Zn, Cd, Hg, Al, Ga, In, Si, Ge, Sn, Pb, As, Te, La, Ce, Pr, Nd, Sm, Eu, Gd, Tb, Db, Tm, Yb, and La, or a divalent cation of any of the foregoing.

In a particular embodiment, the disclosure provides for a MOF of the disclosure, wherein the MOF is reacted with a terminal oxidant, such as $N_2O$. In a further embodiment, a MOF disclosed herein is reacted with $N_2O$ at a temperature of about 75° C. and at a pressure between 1 to 10 bar.

In a certain embodiment, the disclosure also provides for a catalytic device comprising a MOF disclosed herein. In a further embodiment, the device comprises a column or bed which comprises a MOF of the disclosure.

In a particular embodiment, the disclosure further provides methods for oxidizing a molecule or compound, comprising contacting the molecule or compound with a MOF disclosed herein. In another embodiment, the molecule or compound is a $C_1$-$C_6$ alkane, a $C_1$-$C_6$ alkene, a $C_1$-$C_6$ alkyne, benzene, or a $C_3$-$C_6$ cycloalkyl. In a further embodiment, a $C_1$-$C_6$ alkane is converted to a corresponding $C_1$-$C_6$ alcohol or $C_1$-$C_6$ aldehyde by contacting the $C_1$-$C_6$ alkane with a MOF disclosed herein. In yet a further embodiment, a $C_1$-$C_6$ alkane is selectively converted to the $C_1$-$C_6$ alcohol versus the $C_1$-$C_6$ aldehyde in a ratio of 20:1 by contacting the $C_1$-$C_6$ alkane with a MOF disclosed herein. In another embodiment, a $C_1$-$C_6$ alkene is converted to a $C_1$-$C_6$ corresponding epoxide by contacting the $C_1$-$C_6$ alkene with a MOF disclosed herein. In yet another embodiment, cyclohexane is converted into KA oil by contacting cyclohexane with a MOF disclosed herein.

DESCRIPTION OF DRAWINGS

FIG. 3A-B presents the structure of bare and $N_2$O-dosed $Fe_2$(dobdc). (A) Structure of $Fe_2$(dobdc), showing hexagonal channels lined with 5-coordinate iron(II) sites. The view is down the c axis, along the helical chains of iron(II) ions. (B) Experimental structures for $N_2$O binding in $Fe_2$(dobdc) loaded with 0.35 equivalents of $N_2$O at room temperature and then slowly cooled to 10 K. $N_2$O binds with a bent Fe—$N_2$O angle, with a mixture of 60% $\eta^1$-O coordination and 40% $\eta^1$-N coordination. For comparison of calculated structures with experimental, see FIG. 4A-B.

FIG. 4A-B provides a comparison of the experimental and theoretical structures of $N_2$O adducts of $Fe_2$ (dobdc). (A) $\eta^1$-O coordination of the $N_2$O molecule. (B) $\eta^1$-N coordination of the $N_2$O molecule. All distances are in Å and all angles are in degrees. Shown are N, O and, Fe (experiment) or Fe (theory).

FIG. 5 presents powder X-ray (PXRD) diffraction patterns for $Fe_{0.1}Mg_{1.9}$ (dobdc) before (bottom) and after (top) $N_2$O/ethane treatment.

FIG. 15A-B provides (A) FTIR spectra of $Fe_2(dobdc)$ outgassed at room temperature 2 h (black curve) and activated at 433 K for 18 h (red curve) and in contact with 40 mbar of $N_2O$ at room temperature (blue curve). The spectrum of the activated sample clearly shows the disappearance of all features associated with methanol, with all other bands unchanged. (B) FTIR spectra (background subtracted) in the 2280-2160 $cm^{-1}$ spectral range of $Fe_2(dobdc)$ in contact with 40 mbar of $N_2O$ (blue curve) and following progressive desorption at room temperature (light grey curves). A clear maximum is seen at 2226 $cm^{-1}$. The dotted blue line represents the spectrum of 40 mbar of gaseous $N_2O$ in the same spectral range.

FIG. 16A-B provides In situ transmission-mode FTIR spectra of $Fe_2(dobdc)$ (green) and $Fe_2(OH)_2(dobdc)$ (red). A thin film of $Fe_2(dobdc)$ was activated at 433 K for 18 h (red curve), in contact with 180 mbar of $N_2O$ at room temperature (blue curve) and heated at 60° C. for 14 hours (green curve). Inset (A): background subtracted spectra illustrating the ν (N—N) region and inset (B) magnification of 730-610 $cm^{-1}$ spectral range, testifying the formation of $Fe_2(OH)_2$ (dobdc).

FIG. 27 presents a wireframe representation of the cluster model for 4 (89-atom cluster model). Highlighted in ball and stick, the Fe atom and its first coordination sphere and the Zn centers. The 90-atom cluster model for 2 is similar, except 01 is replaced with an OH. Shown are: Fe; Zn; O; C and H.

FIG. 28A-D shows (A) Structure of the metal-organic framework $M_2(dobpdc)$ ($dobpdc^{4-}$=4,4'-dioxidobiphenyl-3, 3'-dicarboxylate), showing hexagonal channels lined with 5-coordinate $M^{2+}$ sites. The view is down the c axis, along the helical chains of $M^{2+}$ ions. $M^{2+}$=yellow; oxygen=red; carbon=gray; hydrogen atoms not shown for clarity. (B) Structure of the ligand, $dobpdc^{4-}$. (C) Structure of a substituted ligand of (B) and (D) a 3-ring variations of the expanded linkers.

DETAILED DESCRIPTION

Figure 1:
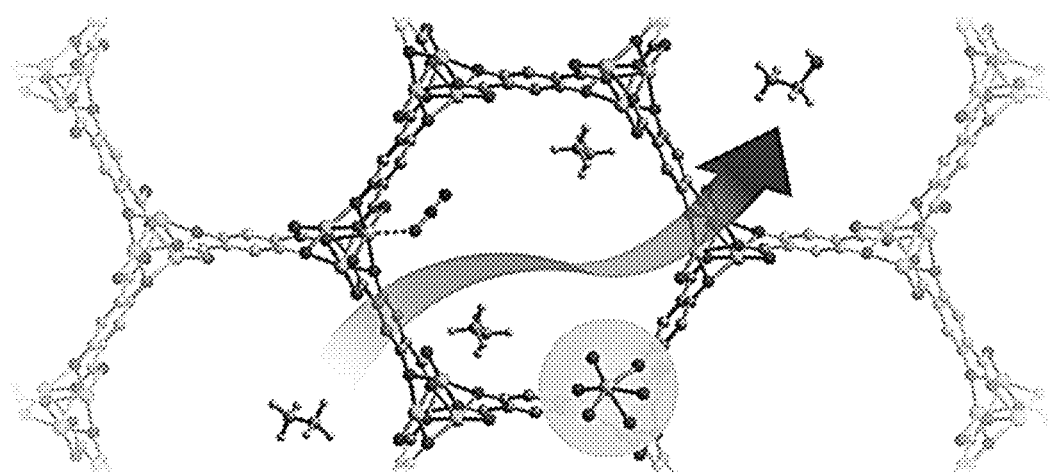
FIG. 1 diagrams a $M_2$(dobdc)-based framework showing a close-up of a SBU and the oxidation of ethane molecule to ethanol via oxidation by the framework.
Figure 2A:
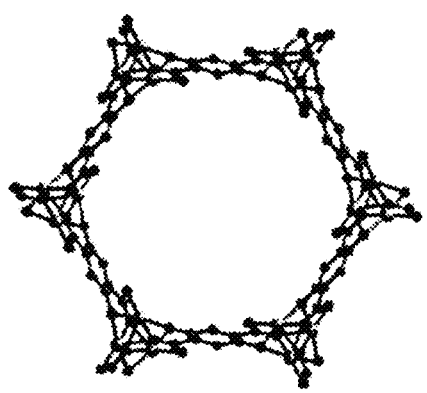
FIG. 2A-C provides (A) Structure of the metal-organic framework $M_2$(dobdc), showing hexagonal channels lined with 5-coordinate $M^{2+}$ sites. The view is down the c axis, along the helical chains of $M^{2+}$ ions. $M^{2+}$=yellow; oxygen=red; carbon=gray; hydrogen atoms not shown for clarity. (B) Structure of the ligand, dobdc$^{4-}$. (C) Structure of the ligand m-dobdc$^{4-}$ which forms a similar framework $M_2$(m-dobdc) that also has hexagonal channels lined with open metal sites.
Figure 2B:
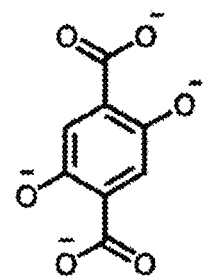
Figure 2C:
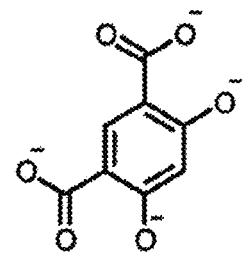
Figure 6:
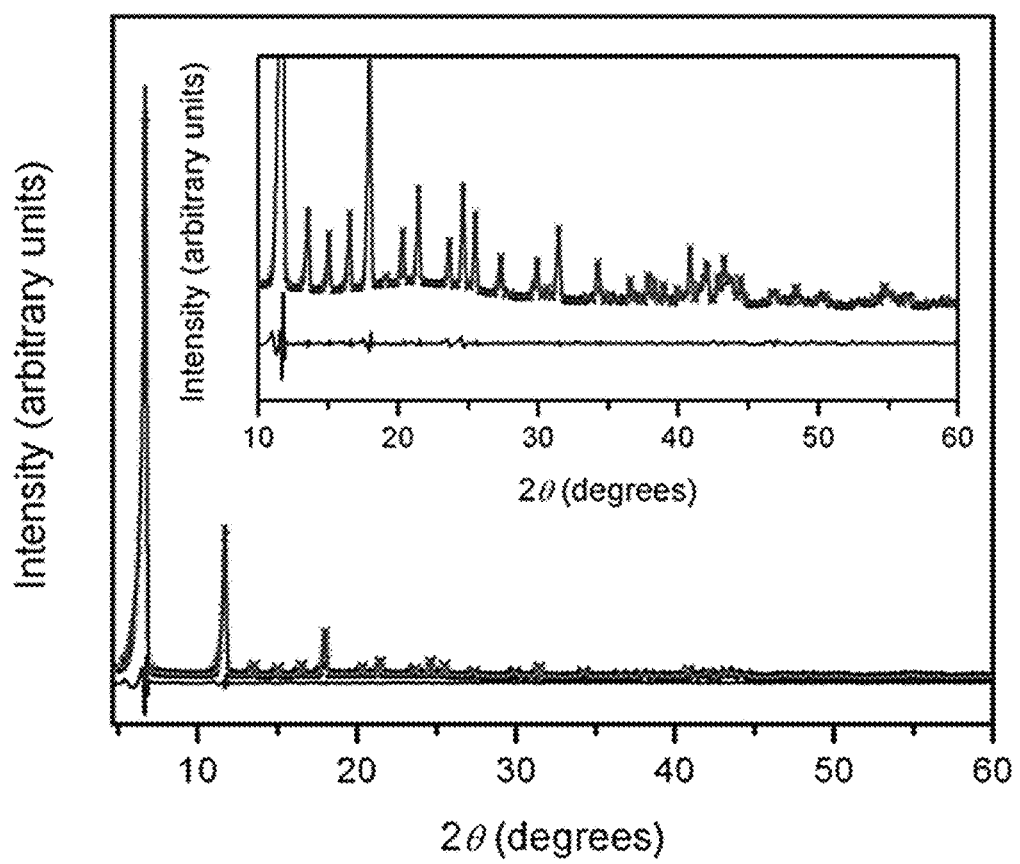
FIG. 6 shows the unit cell of $Fe_{0.1}Mg_{1.9}$ (dobdc). X-ray powder diffraction data obtained from a sample of $Fe_{0.1}Mg_{1.9}$ (dobdc). a=25.9485 (9) Å', c=6.8574 (4) Å', and V=3998.7 (3) Å. The crosses and top line represent the experimental and calculated diffraction patterns, respectively. The bottom line represents the difference between experimental and calculated patterns. The data were collected at 298 K.

As used herein and in the appended claims, the singular forms "a," "an," and "the" include plural referents unless the context clearly dictates otherwise. Thus, for example, reference to "an organic linking ligand" includes a plurality of such linking ligands and reference to "the metal ion" includes reference to one or more metal ions and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. With respect to any term that is presented in one or more publications that is similar to, or identical with, a term that has been expressly defined in this disclosure, the definition of the term as expressly provided in this disclosure will control in all respects.

Metal-organic frameworks (MOFs) are porous crystalline materials that are constructed by the linkage of inorganic metal clusters called secondary building units (SBUs) with organic linkers. These materials have very large surface areas and pore volumes.

The selective and efficient conversion of light alkanes into value-added chemicals remains an outstanding challenge with tremendous economic and environmental impact, especially considering the recent worldwide increase in natural gas reserves. In nature, C—H functionalization is carried out by copper and iron metalloenzymes, which activate dioxygen and, through metal-oxo intermediates, facilitate two- or four-electron oxidations of organic substrates. Duplicating this impressive reactivity in synthetic systems has been the focus of intense research. In particular, iron(IV)-oxo complexes have now been structurally characterized in various geometries (octahedral, trigonal bipyramidal) and spin states (S=1, S=2), and have proven to be competent catalysts for a variety of oxygenation reactions. However, in the absence of a protective protein superstructure, terminal iron-oxo species are highly susceptible to a variety of decomposition pathways, including dimerization to form oxo-bridged diiron complexes, intramolecular ligand oxidation, and solvent oxidation. Tethering a molecular iron species to a porous solid support such as silica or polystyrene could potentially prevent many of these side-reactions. In practice, however, complexes heterogenized in this manner are challenging to characterize by available techniques, and additional problems associated with steric crowding, site inaccessibility, and metal leaching inevitably arise. Iron cations can also be incorporated into zeolites, either as part of the framework or at extraframework sites, producing reactive iron centers that have no direct molecular analogue. Fe-ZSM-5, for example, has been shown to oxidize methane to methanol stoichiometrically when pretreated with nitrous oxide. However, characterization of these materials is nontrivial due to the presence of multiple iron species, and the nature of the active sites in Fe-ZSM-5 remains largely a matter of speculation.

The use of a metal-organic framework to support isolated terminal iron-oxo moieties is a currently unexplored yet highly promising area of research. The high surface area, permanent porosity, chemical and thermal stability, and synthetic tunability displayed by many of these materials makes them appealing in this regard. Additionally, metal-organic frameworks are typically highly crystalline with well-defined metal centers suited for characterization by single crystal and/or powder diffraction techniques. Furthermore, while molecular iron(IV)-oxo complexes generally utilize nitrogen-based chelating ligands, the metal cations in metal-organic frameworks are often ligated by weaker-field ligands, such as carboxylates and aryloxides, which are constrained in their coordination position by the extended framework structure. Thus, in addition to increased stability, terminal oxos in these materials might also have novel electronic properties and reactivity imparted by their unique coordination environment.

While spectroscopic and theoretical studies have long attributed the reactivity of non-heme enzymatic and synthetic iron(IV)-oxo complexes to a quintet spin state, only a small handful of mononuclear high-spin iron(IV)-oxo species have been characterized, with all but one exhibiting a trigonal bipyramidal coordination geometry. In these systems, the oxo moiety is either extremely unstable-[Fe(O)(H$_2$O)$_5$]$^{2+}$, for example, has a half life of roughly 10 s or is inaccessible to substrates due to bulky ligand scaffolds, leading to sluggish reactivity. On the other hand, the Fe$_2$(dobdc) framework features sterically accessible, site-isolated metal centers entrenched in a weak-field ligand environment. Utilizing these two properties, it is possible not only to generate such a species, albeit fleetingly, but also to direct it towards the facile activation of one of the strongest C—H bonds known.

Accordingly, The disclosure provides for metal-organic frameworks (MOFs) comprising a plurality of redox-active metals or metal ions linked together with a plurality of organic linking moieties comprising the structure(s) selected from the group consisting of:

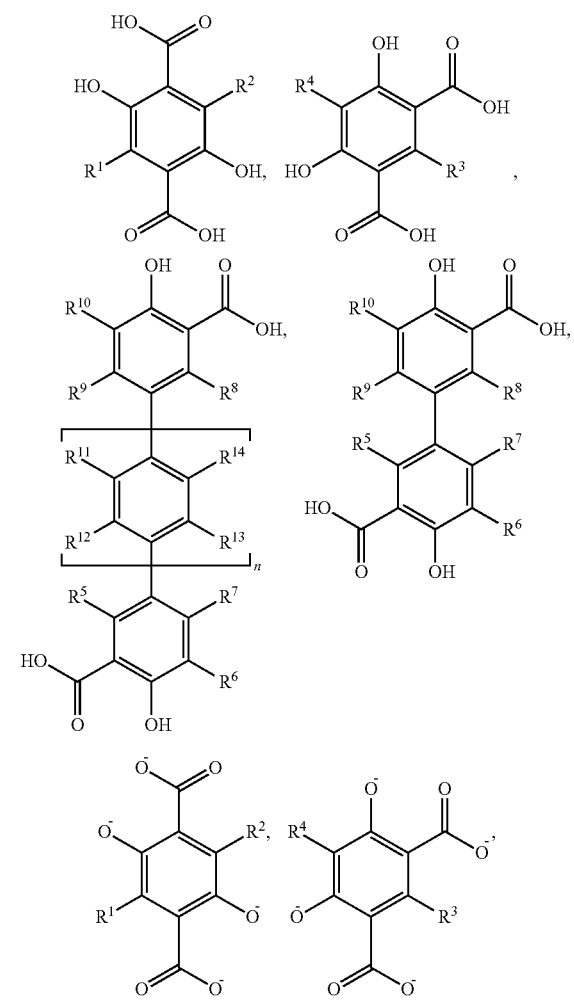

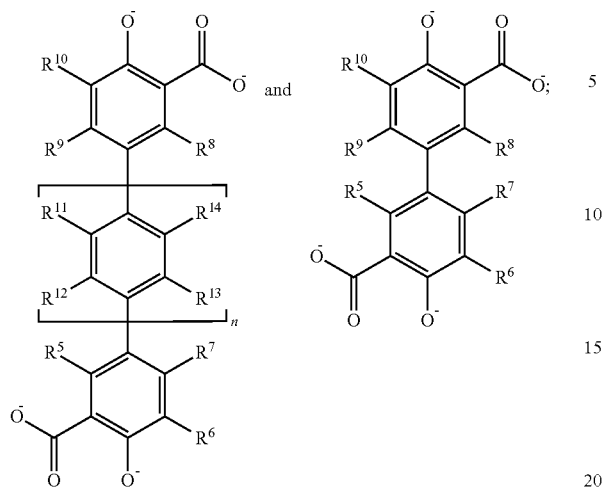

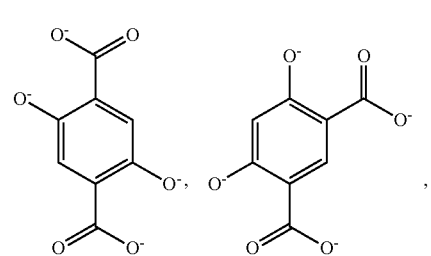

wherein $R^1$-$R^{14}$ are independently selected from H, D, optionally substituted FG, optionally substituted ($C_1$-$C_{20}$) alkyl, optionally substituted ($C_1$-$C_{19}$) heteroalkyl, optionally substituted ($C_1$-$C_{20}$)alkenyl, optionally substituted ($C_1$-$C_{19}$) heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In one embodiment, the organic linking ligand comprises a structure selected from the group consisting of:

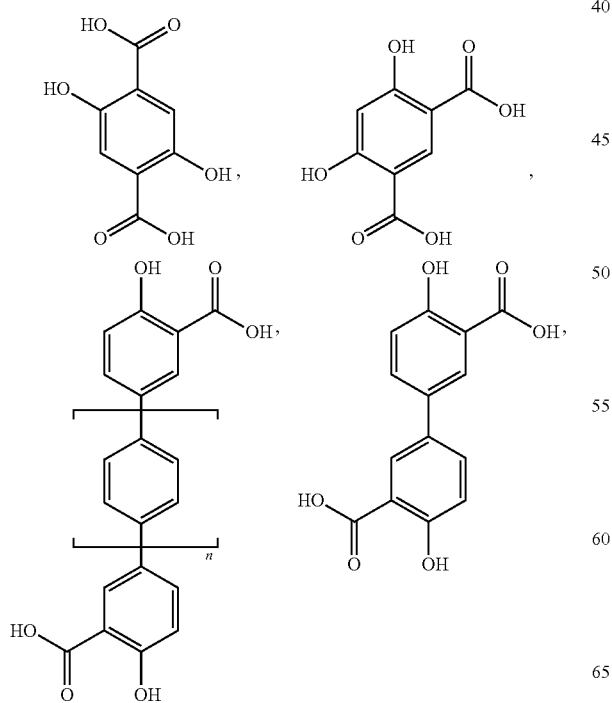

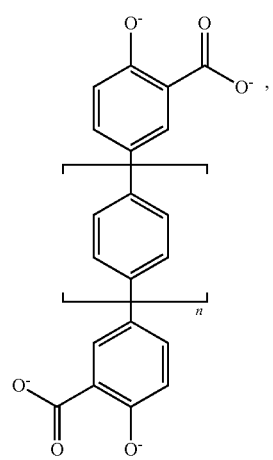

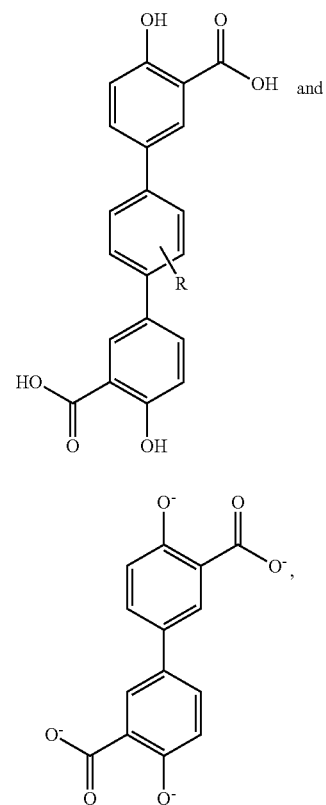

wherein

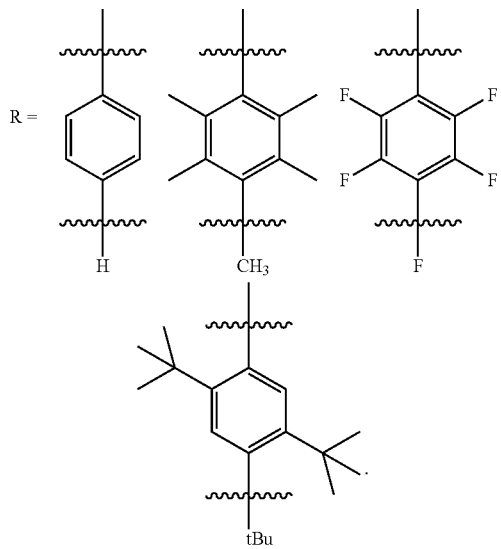

In a specific embodiment, the organic linking ligand is selected from:

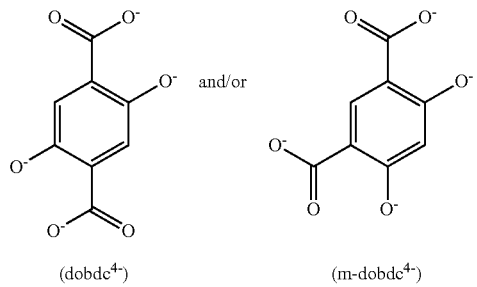 [SMILES: O=C([O-])c1cc([O-])c(C(=O)[O-])cc1[O-] ; O=C([O-])c1cc(C(=O)[O-])c([O-])cc1[O-]]

($dobdc^{4-}$=2,5-dioxido-1,4-benzenedicarboxylate, $m\text{-}dobdc^{4-}$=2,4-dioxido-1,5-benzenedicarboxylate). In all of the foregoing embodiments, the MOF is capable of catalytic oxidation of a hydrocarbon (e.g., ($C_1$-$C_6$)-hydrocarbons) to higher oxidation states (e.g., catalytic oxidation of small hydrocarbons to their corresponding alcohols and aldehydes).

In a further embodiment, the disclosure provides for MOFs that are comprised of a plurality of different redox-active metals or metal ions linked together by a plurality of linking moieties of the disclosure (e.g., $dobdc^{4-}$ and/or $m\text{-}dobdc^{4-}$ linking moieties). In yet a further embodiment, a MOF disclosed herein is comprised of a plurality of redox-active metal or metal ions and a plurality of redox-inactive metal or metal ions, which are linked together by dioxido-benzenedicarboxylate-based organic linking moieties or dihydrooxyterphenyldicarboxylate-based linking moieties. In yet a further embodiment, a MOF of the disclosure (e.g., a mixed metal MOF) is highly selective for catalytically oxidizing an alkane to its corresponding alcohol (e.g., a light weight alkane (e.g., $C_1$-$C_6$ alkane) to a corresponding alcohol) over other oxidative products (e.g., carbonyls, epoxides, and carboxylic acids). In a particular embodiment, a MOF disclosed herein catalyzes the oxidation of a light weight alkane to alcohol versus other oxidative products in a ratio of 2:1, 5:1, 10:1, 15:1, 20:1, 25:1, 30:1, 35:1, 50:1, or 99:1, or in range that falls in between any of the foregoing. For example, a mixed metal MOF disclosed herein can selectively catalyze the oxidation of ethane to ethanol versus acetaldehyde in a 25:1 ratio.

Suitable alkanes that can be oxidized by the methods and compositions of the disclosure include methane ($CH_4$), ethane ($C_2H_6$), propane ($C_3H_8$), butane ($C_4H_{10}$), pentane ($C_5H_{12}$), hexane ($C_6H_{14}$), heptane ($C_7H_{16}$), octane ($C_8H_{18}$), nonane ($C_9H_{20}$), decane ($C_{10}H_{22}$), undecane ($C_{11}H_{24}$), and dodecane ($C_{12}H_{26}$). The methods include not only a single compound, but also combinations of compounds, such as solutions, mixtures and other materials which contain at least one alkane. For alkane/alkene-substrates, propane, propene, ethane, ethene, butane, butene, pentane, pentene, hexane, hexene, cyclohexane, octane, octene, styrene, p-nitrophenoxyoctane (8-pnpane), and various derivatives thereof, can be used. The term "derivative" refers to the addition of one or more functional groups to an alkane, including, but not limited, alcohols, amines, halogens, thiols, amides, carboxylates, etc.

In a certain embodiment, the disclosure provides for reacting the MOF disclosed herein with a terminal oxidant, such as $N_2O$, to generate a $M^{2+}$ redox-active metal center (e.g., $Fe^{2+}$, $Mn^{2+}$, $Co^{2+}$, $Ni^{2+}$, and $Cu^{2+}$). The oxidation can be carried out at low temperatures (about 75° C.) and at low pressures (1 to 10 bar). Accordingly, the MOF disclosed herein can utilize very inexpensive oxidants in thermodynamically favorable conditions without having to use adjuvants, like acids. For example, it was shown herein that the high-spin iron(II) centers within $Fe_2(dobdc)$ ($dobdc^{4-}$=2,5-dioxido-1,4-benzenedicarboxylate) can activate $N_2O$, most likely forming a transient, high-spin iron(IV)-oxo intermediate, which rapidly reacts to afford $Fe_2$ $(OH)_2(dobdc)$. Significantly, the magnesium-diluted analogue, $Fe_{0.1}Mg_{1.9}$ (dobdc), is found to selectively oxidize ethane to ethanol in the presence of $N_2O$ under mild conditions.

Currently, no widespread commercial process exists for the selective oxidative conversion of hydrocarbons into value-added chemical feedstocks such as methanol, ethanol or propanol. Industrially, methanol is produced in an indirect and energy intensive processes beginning with the steam reformation of natural gas; ethanol is largely produced from the acid-catalyzed hydration of ethylene, which itself is produced by steam cracking. The selective hydroxylation of, e.g., $C_1$ to $C_3$, hydrocarbons by the MOFs disclosed herein presents a large environmental and economic impact. More so, when one considers the dramatic worldwide increase in using shale gas reserves, which consists largely of methane but also contains a significant amount of ethane and other light alkane impurities. The metal-organic framework disclosed herein are capable of oxidizing ethane into its various oxygenates when heated to 75° C. in the presence of nitrous oxide. Products include ethanol, acetaldehyde, and ether oligomers. Much greater selectivity, however, can be achieved when using a mixed metal MOF of the disclosure.

In a particular embodiment, a mixed metal MOF of the disclosure can be represented by the formula: $(M^1)_x(M^2)_{2-x}$ (dobdc, m-dobdc and/or $H_4dotpdc^R$), wherein at least one of $M^1$ or $M^2$ is redox-active metal and x is a number less than or equal to 1, 0.9, 0.8, 0.75, 0.7, 0.65, 0.6, 0.55, 0.5, 0.45, 0.4, 0.35, 0.3, 0.25, 0.2, 0.15, 0.1, or 0.05. In a particular embodiment, $M^1$ is selected from Fe, Mn, Co, Ni, and Cu, or a divalent cation of any of the foregoing. In another embodiment, $M^2$ is selected from Fe, Mn, Co, Ni, Cu, Be, Mg, Ca, Sr, Ba, Sc, Y, Ti, Zr, V, Nb, Ta, Cr, Mo, W, Re, Ru, Os, Rh, Ir, Pd, Pt, Ag, Au, Zn, Cd, Hg, Al, Ga, In, Si, Ge, Sn, Pb, As, Te, La, Ce, Pr, Nd, Sm, Eu, Gd, Tb, Db, Tm, Yb, and La, or a divalent cation of any of the foregoing. In yet another embodiment, $M^2$ is selected from Mg, Ca, Sr, Ba, Sc, Y, Ti, Zr, V, Nb, Ta, Cr, Mo, W, Re, Ru, Os, Rh, Ir, Pd, Pt, Ag, Au, Zn, Cd, Hg, Al, Ga, In, Si, Ge, Sn, Pb, As, Te, La, Ce, Pr, Nd, Sm, Eu, Gd, Tb, Db, Tm, Yb, and La, or a divalent cation of any of the foregoing. For example, for a MOF of the disclosure represented by the formula $Fe_xMg_{2-x}$ (dobdc), wherein x<0.3, catalyzed the oxidation of ethane so that only ethanol and acetaldehyde were generated. Further, a ratio of 25:1 of ethanol to acetaldehyde was generated when x=0.1. The MOFs of the disclosure have also been shown to catalytically convert propane to propanol, and propylene to propylene oxide in a highly selective manner. Further, other similar oxidations are possible when using MOFs which are comprised of different redox-active and redox-inactive metals as well as using m-dobdc instead of dobdc.

One of main advantages of the MOFs disclosed herein is high selectively for converting hydrocarbons, (e.g., ($C_1$-$C_6$)-hydrocarbons) to corresponding alcohols (e.g., ($C_1$-$C_6$)-alcohols) under mild conditions can be achieved by using a cheap and abundant first-row transition metal(s). Moreover, de-activated MOFs (e.g., metal in an inactive 3+ state instead of an active 2+ state) can be regenerated by treating the MOFs with a reducing agent, such as exposing the MOFs to 1,4-dienes (e.g., cyclohexadiene).

In a particular embodiment, a MOF of the disclosure can be used for a variety of applications, including for gas, liquid or vapor separation, gas storage, separation of bioproducts or compounds, or catalysis. In particular embodiment, the disclosure provides for MOFs that selectively catalyze the oxidations of one or more molecules. In a further embodiment, a MOF disclosed herein performs one or more of the following catalytic oxidations: oxidation of alkanes (such as ($C_1$-$C_6$) alkanes) into corresponding alcohols and/or aldehydes; catalyzes the oxidation of cyclohexane into KA oil (i.e., a mixture of cyclohexanol and cyclohexanone); catalyzes the oxidation of benzene to phenol; and the oxidation of alkenes to corresponding epoxides (e.g., propylene to propylene oxide, and ethylene to ethylene oxide).

The disclosure also provides an apparatus and method for catalyzing the oxidation of compounds having a feed side and an effluent side separated by a MOF of the disclosure, wherein the one or more reactant(s) are fed on one side and the oxidized product(s) are generated as effluent. The apparatus may comprise a column separation format, such as a heated glass column, wherein the column may comprise the MOF.

In a particular embodiment, a MOF disclosed herein is part of a device. In a further embodiment, the device is a catalytic device which catalyzes the oxidation of light hydrocarbons (e.g., methane, ethane, and propane) into corresponding alcohols and/or aldehydes; catalyzes the oxidation of cyclohexane into KA oil (i.e., a mixture of cyclohexanol and cyclohexanone); catalyzes the oxidation of benzene to phenol; and the oxidation of alkenes to corresponding epoxides (e.g., propylene to propylene oxide, and ethylene to ethylene oxide).

The disclosure also provides methods using a MOF disclosed herein. In a certain embodiment, a method to catalytically oxidize one or more hydrocarbons using a MOF disclosed herein is provided.

A MOFs used in the embodiments of the disclosure include a plurality of pores for catalysis. In one variation, the plurality of pores has a unimodal size distribution. In another variation, the plurality of pores have a multimodal (e.g., bimodal) size distribution.

The following examples are intended to illustrate but not limit the disclosure. While they are typical of those that might be used, other procedures known to those skilled in the art may alternatively be used.

EXAMPLES

General. Unless otherwise noted, all procedures were performed under an $N_2$ atmosphere using standard glove box or Schlenk techniques. N,N-dimethylformamide (DMF) was dried using a commercial solvent purification system designed by JC Meyer Solvent Systems and then stored over 4 Å molecular sieves. Anhydrous methanol was purchased from commercial vendors, further dried over 3 Å sieves for 24 hours, and deoxygenated prior to being transferred to an inert atmosphere glove box, where it was stored over 3 Å molecular sieves. The ethane, argon, and nitrous oxide used in reactivity studies were purchased at 99.999%, 99.999%, and 99.998% purity, respectively. The 30% $N_2O/N_2$ mixture used to synthesize $Fe_2(OH)_2$(dobdc) was purchased from commercial vendors using 99.5% purity $N_2O$ and 99.999% purity $N_2$. All other reagents were obtained from commercial vendors at reagent grade purity or higher and used without further purification. Carbon, hydrogen, and nitrogen analyses were obtained from the Microanalytical Laboratory at the University of California, Berkeley.

$^1$H-Nuclear Magnetic Resonance. $^1$H-NMR spectra were obtained using a Bruker AVB-400 instrument and peaks were referenced to residual solvent peaks.

Figure 7:
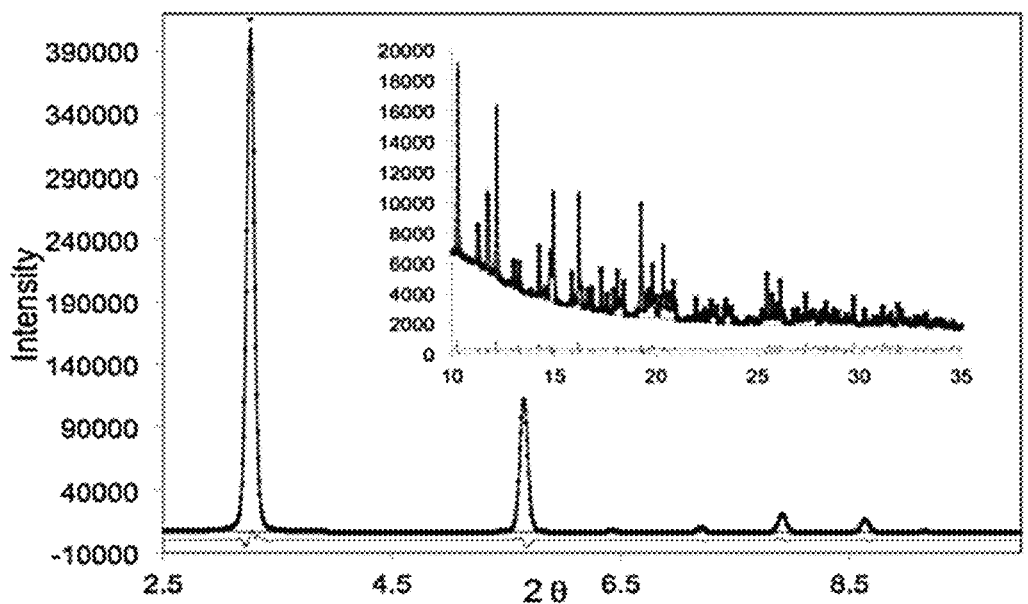
FIG. 7 provides a Rietveld refinement (100 K) of $Fe_2$(OH)$_2$(dobdc). X-ray powder diffraction data obtained from a sample of $Fe_2$(OH)$_2$(dobdc). The middle line, crosses, and top line represent the background, experimental, and calculated diffraction patterns, respectively. The bottom line represents the difference between experimental and calculated patterns. The data were collected at 100 K.
Figure 8:
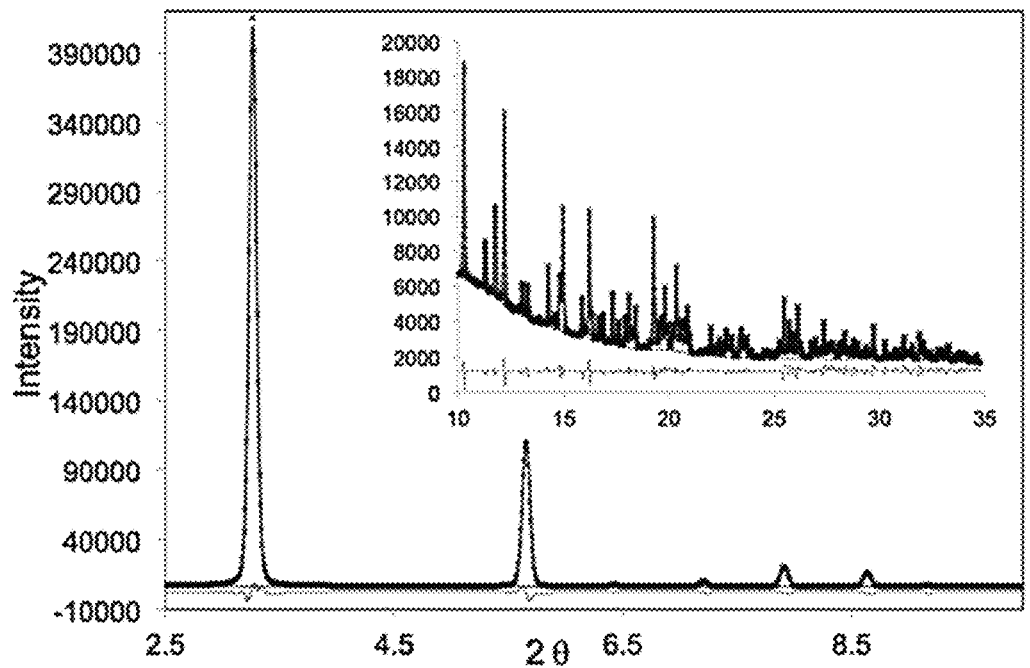
FIG. 8 provides a Rietveld refinement (298 K) of $Fe_2$(OH)$_2$(dobdc). X-ray powder diffraction data obtained from a sample of $Fe_2$(OH)$_2$(dobdc). The middle line, crosses, and top line represent the background, experimental, and calculated diffraction patterns, respectively. The bottom line represents the difference between experimental and calculated patterns. The data were collected at 298 K.
Figure 9:
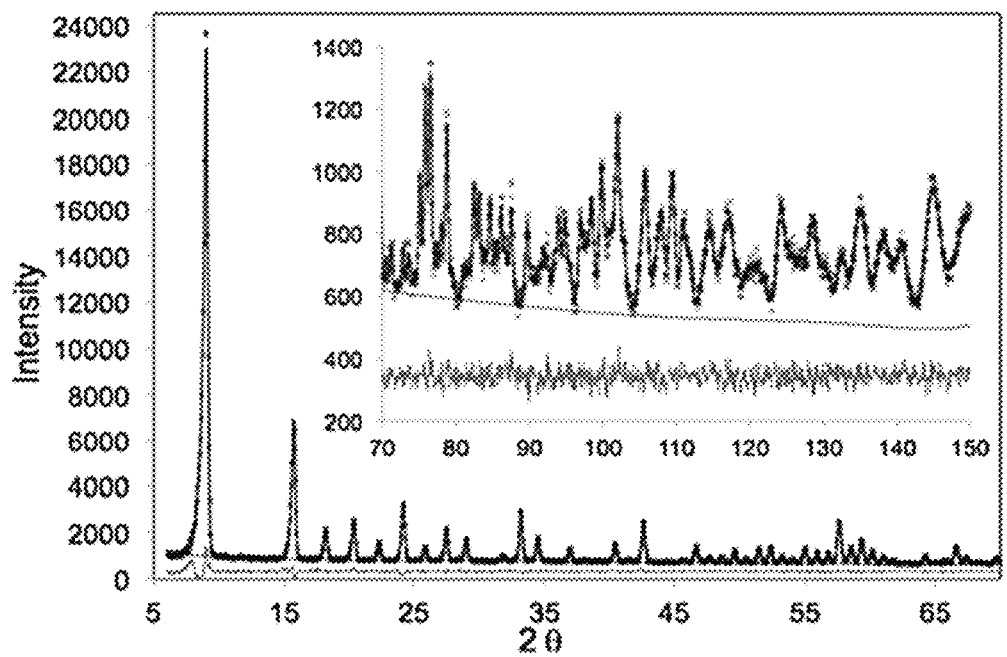
FIG. 9 provides a Rietveld refinement (10 K) of bare $Fe_2$(dobdc). Neutron powder diffraction data obtained from bare $Fe_2$(dobdc) at 10 K. The middle line, crosses, and top line represent the background, experimental, and calculated diffraction patterns, respectively. The bottom line represents the difference between experimental and calculated patterns.
Figure 10:
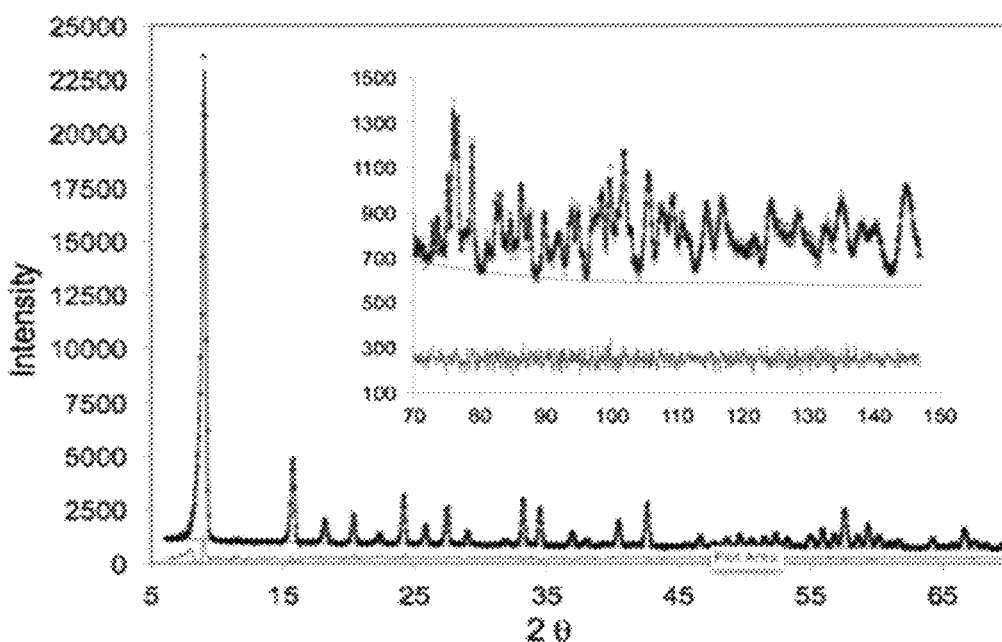
FIG. 10 provides a Rietveld refinement (10 K) of $Fe_2$(dobdc) ($N_2$O)$_{0.7}$. Neutron powder diffraction data obtained from $Fe_2$(dobdc) loaded with approximately 0.35 $N_2$O per $Fe^{2+}$. The middle line, crosses, and top line represent the background, experimental, and calculated diffraction patterns, respectively. The bottom line represents the difference between experimental and calculated patterns. The data were collected at 10 K.
Figure 11:
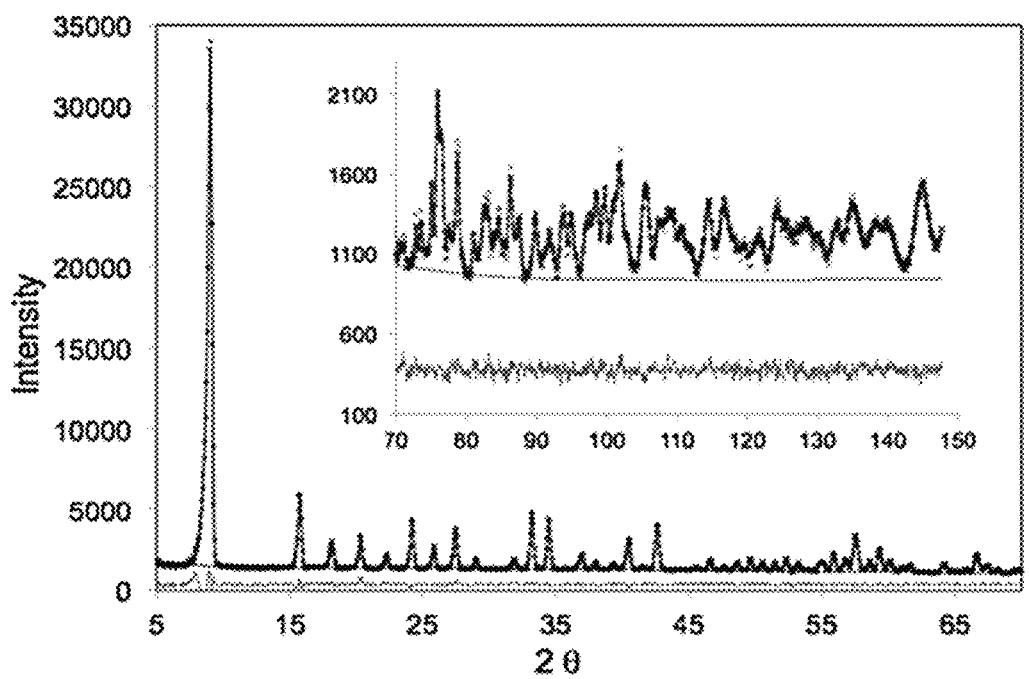
FIG. 11 provides a Rietveld refinement (10 K) of $Fe_2$ (dobdc) ($N_2$O)$_{1.2}$. Neutron powder diffraction data obtained from $Fe_2$(dobdc) loaded with approximately 0.6 $N_2$O per $Fe^{2+}$. The middle line, crosses, and top line represent the background, experimental, and calculated diffraction patterns, respectively. The bottom line represents the difference between experimental and calculated patterns.
Figure 12:
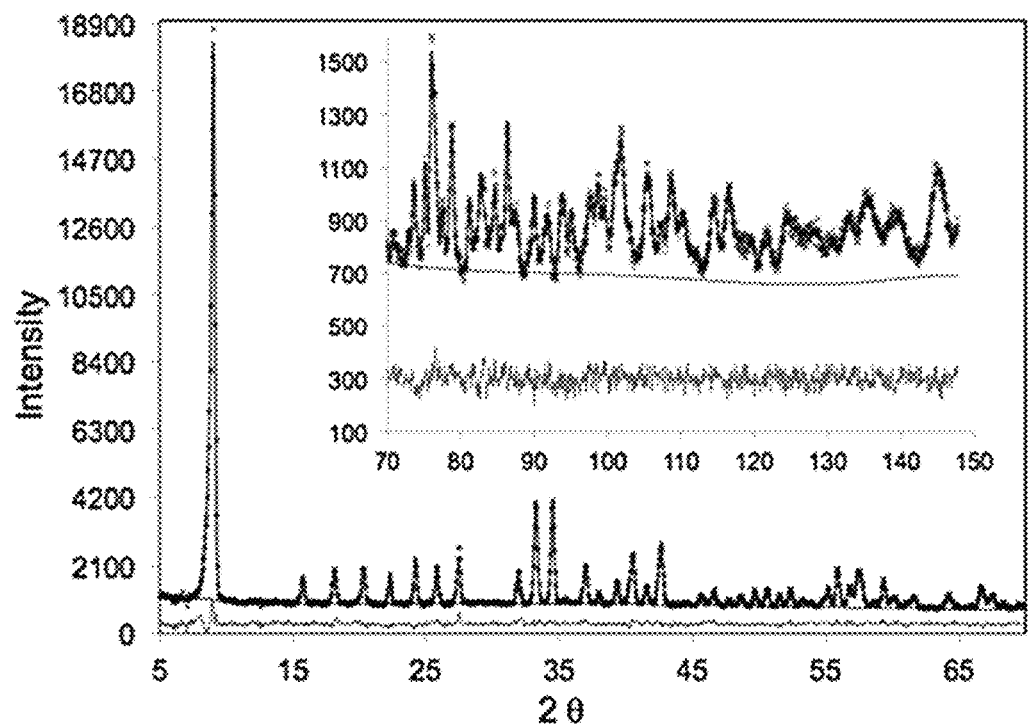
FIG. 12 provides a Rietveld refinement (10 K) of $Fe_2$ (dobdc) ($N_2$O)$_{2.5}$. Neutron powder diffraction data obtained from $Fe_2$(dobdc) loaded with approximately 1.25 $N_2$O per $Fe^{2+}$. The middle line, crosses, and top line represent the background, experimental, and calculated diffraction patterns, respectively. The bottom line represents the difference between experimental and calculated patterns. The data were collected at 10 K.

Powder X-Ray Diffraction Data Collection and Refinement. X-ray diffraction data on $Fe_2(OH)_2$(dobdc) were collected on a Beamline 17-BM-B at the Advanced Photon Source at Argonne National Laboratory (see FIGS. 7 and 8). The sample was first heated in the presence of $N_2O$, from room temperature to 60° C. over the course of two days. Excess $N_2O$ was removed, and the sample was pumped into an $N_2$ purged glove box where it was loaded into a 1.0 mm borosilicate capillary. The capillary was attached to a custom designed gas cell to maintain an inert atmosphere, and then brought out of the glove box. The cell was then attached to an outgassing port on a Micromeritics ASAP 2020, where the remaining $N_2$ was removed and the sample was dosed with a small amount of Helium to serve as exchange gas. The capillary was then flame sealed for measurement. At 17-BM the capillary was mounted onto the goniometer head and then centered in the beam. Powder X-ray diffraction patterns (PXRD) were recorded using a Bruker D8 Advance diffractometer (Göbel-mirror monochromated Cu Kα radiation λ=1.54056 Å).

EXAFS Data Collection and Refinement.

X-ray absorption spectra (XAS) were collected at the Advanced Light Source (ALS) on beamline 10.3.2 with an electron energy of 1.9 GeV and an average current of 500 mA. The radiation was monochromatized by a Si(111) double-crystal monochromator. Intensity of the incident X-ray was monitored by an $N_2$-filled ion chamber ($I_0$) in front of the sample. Fluorescence spectra were recorded using a seven-element Ge solid-state detector. The rising K-edge energy of Fe metal foil was calibrated at 7111.20 eV.

Data reduction of the XAS spectra was performed using custom-made software. Pre-edge and post-edge contributions were subtracted from the XAS spectra, and the results were normalized with respect to the edge jump. Background removal in k-space was achieved through a five-domain cubic spline. Curve fitting was performed with Artemis and IFEFFIT software using ab initio-calculated phases and amplitudes from the program FEFF.

Powder Neutron Diffraction Data Collection and Refinement.

Neutron powder diffraction (NPD) data (see FIGS. 9-12) were collected on the high-resolution neutron powder diffractometer, BT1, at the National Institute of Standards and Technology (NIST) Center for Neutron Research. An activated sample of $Fe_2$(dobdc) (2.027 g) was placed inside a He-purged glove box and loaded into a vanadium sample can equipped with a gas loading lid. The sample was then sealed inside of the can using an indium o-ring and was then removed from the glove box and placed on a bottom-loading closed cycle refrigerator. The sample was first cooled to 10 K for data collection of the bare framework using a Ge(311) monochromator ($\lambda$=2.0781 Å) and a 60 minute collimator. $Fe_2$(dobdc) was then warmed to room temperature where it was dosed with various predetermined amounts of $N_2O$ gas, approximately 0.35, 0.60, and 1.25 $N_2O$ molecules per $Fe^{2+}$ site. For each gas dosing the pressure was first allowed to equilibrate over a ten minute period at room temperature, and then the sample was slowly cooled to 10 K over a period of approximately 2.5 hours for data collection. Room-temperature neutron powder diffraction data were collected on the high-resolution neutron powder diffractometer, BT1, using a Ge(311) monochromator ($\lambda$=2.0781 Å) and a 60 minute collimator. All NPD data were analyzed using the Rietveld method as implemented in EXPGUI/GSAS software package.

Mössbauer Spectroscopy.

Iron-57 Mössbauer spectra were obtained at 295 K with a constant acceleration spectrometer and a cobalt-57 rhodium source. Prior to measurements the spectrometer was calibrated at 295 K with $\alpha$-iron foil. Samples were prepared inside a $N_2$-filled glove box and contained 20 mg/cm$^2$ of sample (7 mg/cm$^2$ of iron) diluted with boron nitride. All spectra were fit with symmetric Lorentzian quadrupole doublets using the WMOSS Mössbauer Spectral Analysis Software (wmoss.org).

Transmission and ATR Infrared Spectroscopy.

Attenuated total reflectance (ATR) infrared spectra were collected at 4 cm$^{-1}$ resolution on a Perkin Elmer Avatar Spectrum 400 FTIR spectrometer equipped with a Pike attenuated total reflectance accessory. The instrument was placed inside an $N_2$-filled glove bag for measurement of air-sensitive samples. In situ transmission FTIR spectra were collected at 2 cm$^{-1}$ resolution on a Bruker Vertex 70 spectrophotometer equipped with a DTGS detector. The materials were examined in the form of self-supporting pellets (15-20 mg/cm$^2$) mechanically protected with a pure gold frame. Samples were inserted in a quartz IR cell, equipped with KBr windows and characterized using a very small optical path. The cell was attached to a conventional high vacuum glass line capable of a residual pressure less than 10$^{-4}$ mbar. This setting allowed both thermal treatment and adsorption-desorption cycles of molecular probes in situ. All materials were prepared and inserted into the IR cell inside an $N_2$-filled glove box to avoid contact with oxygen and moisture. $Fe_2$(dobdc) samples were activated under dynamic vacuum (residual pressure <10$^{-4}$ mbar) at 433 K for 18 h before being contacted with increasing pressures of $N_2O$ (up to 40 mbar).

Low-Pressure $N_2$ Isotherms.

For all gas adsorption measurements, 100-200 mg of sample were transferred to a preweighed glass sample tube under an atmosphere of nitrogen and capped with a Transeal. Samples were then transferred to a Micromeritics ASAP 2020 gas adsorption analyzer and heated at a rate of 0.1 K/min from room temperature to a final temperature of 433 K and 483 K for $Fe_2$(dobdc) and $Fe_{0.1}Mg_{1.9}$(dobdc), respectively. Samples of $Fe_2(OH)_2$(dobdc) were degassed at room temperature. Samples were considered activated when the outgas rate at the degassing temperature was less than 2 pbar/min. Evacuated tubes containing degassed samples were then transferred to a balance and weighed to determine the mass of sample. The tube was transferred to the analysis port of the instrument where the outgas rate was again determined to be less than 2 pbar/min. Nitrogen gas adsorption isotherms at 77 K were measured in liquid nitrogen.

Calculations for Periodic Systems.

Starting from the experimental powder X-ray crystal structure, the periodic structures for 2 and 4 were fully optimized using periodic density functional theory as implemented in the Vienna ab initio simulation package (VASP) employing the generalized gradient approximation exchange-correlation functional PBE. A Hubbard U correction of 5 eV was added to the intra-site Coulomb interactions of the d-orbitals of the iron atoms to decrease the delocalization of electron density that results from the presence of the self-interaction of electrons in the PBE non-hybrid density functional. The VASP calculations use projector-augmented wave potentials to describe the interaction between core and valence electrons. A plane-wave kinetic energy cutoff of 610 eV was used and the integration over the irreducible Brillouin zone was carried out over a 3×3×3 k-points grid. Atomic positions were relaxed until the forces were lower than 0.06 eV/A. All possible spin states were considered.

Cluster Calculations.

From the initial periodic structures of 2 and 4, we designed two corresponding model clusters containing three neighboring metal centers (along a single helical chain) and their first coordination spheres. These clusters are analogous to the recently reported 88-atom cluster for $Fe_2$(dobdc), which contained three pentacoordinate Fe(II) centers and six organic linkers. As in the case of the 88-atom cluster model, the cluster model of 4 (containing 89 atoms, equivalent to the 88-atom cluster plus an additional O atom coordinated to the central Fe) and the cluster model of 2 (containing 90 atoms, equivalent to the 88-atom cluster plus an additional OH group coordinated to the central Fe) were designed to maintain an overall zero charge for the model system and to preserve a good representation of the first coordination sphere of the central iron atom from the periodic structure. The charge of the cluster was set to zero by addition of protons was noted. The cluster models were simplified by substituting the two peripheral Fe(II) ions with Zn(II) ions, while keeping only the central Fe ion in the cluster (note that Fe(II) ions were not replaced by Zn(II) ions for the periodic calculations).

Two-step constrained geometry optimizations were performed. In the first step, the protons added to neutralize the cluster charge were optimized, while all the other atoms were kept in fixed positions. In the second step, only the central Fe and its first coordination sphere were allowed to relax. The first coordination sphere consists of the Fe atom, the five O atoms of the bare MOF, and the atoms of the adsorbate (O, OH, or $N_2O$); since this involves optimizing six atoms of the bare MOF, it is denoted "opt6". All the optimizations were followed by frequency calculations to confirm that the stationary point was a minimum, which was indicated by the absence of any imaginary frequency in the optimized degrees of freedom.

All density functional cluster calculations used the Gaussian 09 software package or a locally modified version of Gaussian 09. The PBE, M06-L, M06, M08-SO, MPW1B95, and PW6B95 exchange-correlation functionals were employed. For the Minnesota density functionals (M06-L, M06, M08-SO, MPW1B95, and PW6B95), an ultrafine grid (99 radial nodes and 590 angular nodes) was used to perform numerical integrations. The stable=opt keyword of Gaussian was used to test the stability of the Kohn-Sham Slater determinant and converge to a stable solution. An automatic density-fitting set generated by the Gaussian program was used to reduce the cost for calculations done with the local density functionals, PBE and M06-L. The 6-31G(d) basis set was used for H, C, N, O, and Mg while the Stuttgart [8s7p6d1f\6s5p3d1f] ECP10MDF contracted effective core potential basis set was employed for Fe and Zn. Single-point calculations were performed with the 6-311+G(2df,p) basis set for H, C, and O and the Stuttgart [8s7p6d1f 6s5p3d1f] ECP10MDF contracted effective core potential basis set for Fe and Zn. These basis sets have been previously successfully employed in the study of molecular systems with similar M=O and M-OH motifs.

Multi-Reference Calculations.

Single-point multiconfigurational complete active space (CASSCF) calculations followed by second-order perturbation theory (CASPT2) were performed at the DFT-optimized (PBE/SDD(Fe, Zn), 6-31G(d) (C, H, O)) geometries of the cluster models of 2 and 4. These calculations were performed with the Molcas 7.8 software package. Scalar relativistic effects were included by use of the second order Douglas-Kroll-Hess Hamiltonian. The computational cost arising from the two-electron integrals was reduced by employing the Cholesky decomposition technique (RICD). The relativistic all-electron ANO-RCC basis sets were used for all atoms; in particular, the ANO-RCC-VTZP basis set was used for Fe, for the five first-coordination-sphere O atoms of Fe in the MOF fragment, and for the O or OH atoms of the adsorbate. ANO-RCC-VDZP was used for the Zn and all other O atoms, and ANO-RCC-MB was used for all C and H atoms. No symmetry (point group $C_1$) was used, and all possible spin states were considered. The default IPEA shift of 0.25 eV was used in CASPT2, along with an imaginary shift of 0.2 eV.

An active space containing 10 electrons in 11 orbitals (10,11) was used for the cluster model of 4. An active space containing 5 electrons in 5 orbitals (5,5), which contains the five d electrons of Fe(III) in the five 3d orbital was used for the cluster model of 2. The sigma bonding orbital of the metal to the —OH ligand is doubly occupied in the inactive space, along with the five other Fe—O sigma bonding orbitals.

Synthesis of $Fe_2(OH)_{0.6}(dobdc)$ and $Fe_2(OH)_2(dobdc)$.

$Fe_2(dobdc)$ was synthesized according to Bloch et al. (*J. Am. Chem. Soc.* 133, 14814-14822 (2011)). An evacuated schlenk flask containing fully desolvated $Fe_2(dobdc)$ (100 mg, 0.33 mmol) was placed under an atmosphere of 30% $N_2O$ and 70% $N_2$. The flask was immersed in an oil bath, and the temperature was increased by 10° C. every 12 hours, from 25° C. up to 60° C., to obtain $Fe_2(OH)_2(dobdc)$ as a dark red-brown solid. If the reaction is stopped after 12 hours at 35° C., the partially oxidized $Fe_2(OH)_{0.6}(dobdc)$ (as determined by Mössbauer) is obtained. Anal. Calc. for $C_8H_4Fe_2O_8$: C, 28.28; H, 1.19. Found: C, 29.18; H, 1.16. IR (solid-ATR): 3679 (m), 1532 (s), 1450 (s), 1411 (s), 1361 (s), 1261 (s), 1154 (w), 1129 (w), 1077 (w), 909 (m), 889 (s), 818 (s), 807 (s), 667 (s), 630 (m), 594 (s), 507 (s).

Synthesis of $Fe_2(^{18}OH)_{0.6}(dobdc)$.

Dried $^{18}O$-labeled ammonium nitrate (50 mg, 0.58 mmol) was placed in a stainless steel reactor equipped with a two-way valve connected to a hose adapter. The reactor was evacuated and refilled with $N_2$ (3×) and then heated, closed, to 200° C. After 24 hours, the reactor was cooled to 0° C., and the evolved $N_2^{18}O$ was carefully condensed into an evacuated schlenk flask cooled to 77 K containing $Fe_2(dobdc)$ (15 mg, 0.05 mmol). The sample was allowed to react for 12 hours at 35° C., after which the partially oxidized sample was analyzed by IR.

Synthesis of $Fe_{0.1}Mg_{1.9}(dobdc)$.

In a 500 mL schlenk flask, $H_4(dobdc)$ (1.75 g, 8.8 mmol), $MgCl_2$ (1.47 g, 15.4 mmol), and $FeCl_2$ (0.84 g, 6.6 mmol) were dissolved in DMF (310 mL) and MeOH (40 mL). The reaction was stirred vigorously at 120° C. for 16 hours. The precipitate was filtered and stirred in fresh DMF (250 mL) at 120° C. for three hours. Two more DMF washes at 120° C. were performed, after which the precipitate was filtered and soaked in methanol at 60° C. The methanol exchanges were repeated until no DMF stretches were visible by IR. The framework was fully desolvated under dynamic vacuum (<15 μbar) at 210° C. for 2 days to afford $Fe_{0.1}Mg_{1.9}$ (dobdc) as a bright yellow-green solid (2.02 g, 8.2 mmol, 93% yield). $Fe_{0.44}Mg_{1.56}$(dobdc) and other analogs with different Fe:Mg ratios can be obtained by simply varying the ratio of $MgCl_2$ and $FeCl_2$ while keeping all other synthetic conditions the same. The iron to magnesium ratio was determined by ICP-OES. Anal. Calc. for $C_8H_2Fe_{0.1}Mg_{1.9}O_6$: C, 39.08; H, 0.82. Found: C, 39.37; H, 0.43. IR (solid-ATR): 1577 (s), 1484 (m), 1444 (s), 1429 (s), 1372 (s), 1236 (s), 1210 (s), 1123 (m), 911 (m), 892 (s), 828 (s), 820 (s), 631 (s), 584 (s), 492 (s).

Synthesis of $Fe_2(Dobpdc)$ and Other Expanded Analogues:

$Fe_2(dobpdc)$ ($dobpdc^{4-}$=4,4'-dioxidobiphenyl-3,3'-dicarboxylate) can be synthesized by combining 2.5 equivalents of $FeCl_2$ with 1 equivalent of ligand in a mixture of DMF:MeOH (8:2) at 120° C. for 18 hours; the three-ring frameworks can be synthesized in a similar manner. After methanol exchanges, the frameworks can be fully desolvated upon heating to 250° C. under dynamic vacuum to generate exposed $Fe^{II}$ sites. The mixed Fe/Mg frameworks can be synthesized by using a mixture of $FeCl_2$ and $MgCl_2$ for a total of 2.5 equivalents of metal per equivalent of ligand.

Synthesis of $Fe_2(Dotpdc)$ and Other Expanded Analogues:

$Fe_2(dotpdc)$ ($H_4dotpdc$=4,4''-dihydroxy-[1,1':4',1''-terphenyl]-3,3''-dicarboxylic acid:

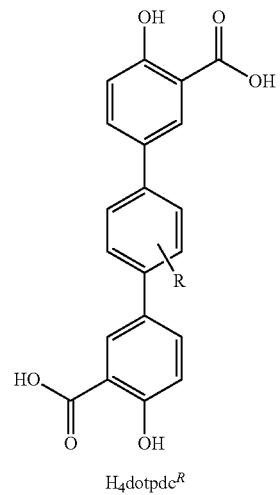

$H_4dotpdc^R$ can be synthesized by combining 2.5 equivalents of $FeCl_2$ with 1 equivalent of ligand in a mixture of DMF:MeOH (9:1) at 140° C. for 48 hours. After methanol exchanges, the framework can be fully desolvated upon heating to 180° C. under dynamic vacuum to generate exposed $Fe^{II}$ sites. Frameworks containing the other ligand derivatives (R=H, $CH_3$, F, and tBu):

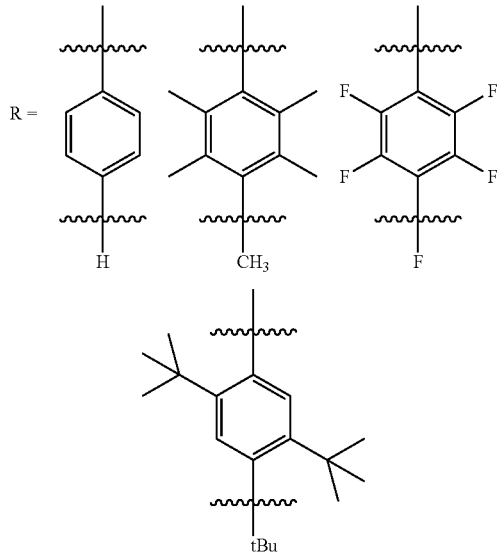

can be synthesized in a similar manner.

PXRD characterization and Rietveld Analysis of $Fe_xMg_{2-x}$ (dobdc) frameworks: Data was first collected at room temperature using a Si (111) monochromator ($\lambda$=0.7291 Å, $\Delta E/E$=1.5*10$^{-4}$) and then again after the sample was cooled at a rate of 2 K/min to 100 K in an $N_2$ cryostream. It should be noted that the sample was held at 100 K for 30 minutes prior to data measurement to allow for temperature equilibration. Rietveld analysis was carried out on both data sets in order to elucidate the site positions of the OH groups on the $Fe^{3+}$ centers. Results of Rietveld analysis obtained from X-ray diffraction experiments of $Fe_2(OH)_2$ (dobdc) can be seen in TABLE 1 and TABLE 2:

TABLE 1

Rietveld Refinement (100K.) of $Fe_2$ $(OH)_2$(dobdc).
Space group R-3, a = 25.6125(2) Å, c = 6.8036(1) Å, and V = 3865.20(8) Å$^3$. This data was obtained from 11-BM at the Advanced photon source at Argonne National Laboratory using a wavelength of 0.7291 Å.

| Atom | x | y | z | occ. | Uiso*100 (Å$^2$) |
|---|---|---|---|---|---|
| Fe | 0.3893(1) | 0.3510(1) | 0.1539(3) | 1.0 | 2.95* |
| O1 | 0.3230(3) | 0.2972(4) | 0.356(1) | 1.0 | 2.3(2) |
| O2 | 0.3009(4) | 0.2289(3) | 0.594(1) | 1.0 | 2.3(2) |
| O3 | 0.3553(3) | 0.2727(4) | 0.000(1) | 1.0 | 2.3(2) |
| C1 | 0.3164(8) | 0.2467(6) | 0.415(2) | 1.0 | 1.1(2) |
| C2 | 0.3260(6) | 0.2052(7) | 0.288(2) | 1.0 | 1.1(2) |
| C3 | 0.3431(5) | 0.2202(7) | 0.092(2) | 1.0 | 1.1(2) |
| C4 | 0.3492(6) | 0.1795(7) | -0.044(2) | 1.0 | 0.9(2) |
| OH | 0.4524(4) | 0.3473(5) | 0.294(1) | 1.0 | 8.66* |

*Uaniso Fe = [$U_{11}$, $U_{22}$, $U_{33}$, $U_{12}$, $U_{13}$, $U_{23}$] = [4.0(2), 1.9(2), 1.7(1), 0.5(2), 0.4(2), 0.4(2)];
Uaniso Ox = [$U_{11}$, $U_{22}$, $U_{33}$, $U_{12}$, $U_{13}$, $U_{23}$] = [7(1), 15(1), 8(1), 10(1), 0.00, 0.00]

TABLE 2

Rietveld Refinement (298K) of the $Fe_2(OH)_2$(dobdc).
Space group R-3, a = 25.6191(2) Å, c = 6.8042(1) Å, and V = 3867.55(9) Å$^3$

| Atom | x | y | z | occ. | Uiso*100 (Å$^2$) |
|---|---|---|---|---|---|
| Fe | 0.3897(1) | 0.3512(1) | 0.1540(4) | 1.0 | 3.14* |
| O1 | 0.3222(4) | 0.2967(4) | 0.358(1) | 1.0 | 2.6(2) |
| O2 | 0.3005(4) | 0.2295(4) | 0.596(1) | 1.0 | 2.6(2) |
| O3 | 0.3553(4) | 0.2736(4) | -0.004(2) | 1.0 | 2.6(2) |
| C1 | 0.3167(8) | 0.2473(7) | 0.416(2) | 1.0 | 1.6(2) |
| C2 | 0.3265(6) | 0.2051(7) | 0.294(2) | 1.0 | 1.6(2) |
| C3 | 0.3431(6) | 0.2219(7) | 0.101(2) | 1.0 | 1.6(2) |
| C4 | 0.3488(6) | 0.1815(7) | -0.039(2) | 1.0 | 1.6(2) |
| Ox | 0.4528(5) | 0.3489(6) | 0.297(1) | 1.0 | 12.2* |

*Uaniso Fe = [$U_{11}$, $U_{22}$, $U_{33}$, $U_{12}$, $U_{13}$, $U_{23}$] = [4.4(2), 1.8(2), 1.5(1), 0.3(2), 0.5(2), -0.3(2)];
Uaniso Ox = [$U_{11}$, $U_{22}$, $U_{33}$, $U_{12}$, $U_{13}$, $U_{23}$] = [8(1), 27(2), 9(1), 14(1), 0.00, 0.00]

For the unit cell determination of $Fe_xMg_{2-x}$(dobdc), a microcrystalline sample of the material was gently ground and loaded into a 1.0 mm borosilicate capillary inside an $N_2$-filled glove box. The sample was sealed temporarily with silicone grease before it was taken out of the box and flame-sealed. Diffraction data were collected during an overnight scan in the $2\theta$ range of 4-65° with 0.020 steps using a Bruker AXS D8 Advance diffractometer equipped with CuK$\alpha$ radiation ($\lambda$=1.5418 Å), a Lynxeye linear position-sensitive detector, and mounting the following optics: Göbel mirror, fixed divergence slit (0.6 mm), receiving slit (3 mm), and secondary beam Soller slits (2.5°). The generator was set at 40 kV and 40 mA. A standard peak search, followed by indexing via the Single Value Decomposition approach, as implemented in TOPAS-Academic, allowed the determination of approximate unit cell dimensions. Precise unit cell dimensions were determined by performing a structureless Le Bail refinement in TOPAS-Academic.

Neutron Fourier Difference Analysis of $Fe_2$(Dobdc).

Neutron Fourier difference analysis of the bare $Fe_2$(dobdc) framework revealed no excess scattering density in the channel indicating that the sample was sufficiently activated. The structural model of the activated material was refined with all structural and peak profile parameters free to vary, resulting in a structure very similar to that previously determined (see TABLE 3).

TABLE 3

Rietveld Refinement (10K) of $Fe_2$(dobdc). Fractional atomic coordinates, occupancies, and isotropic displacement parameters obtained from Rietveld refinement of structural model of the bare $Fe_2$(dobdc) framework at 10K, space group R-3, a = 26.1826(6) Å, c = 6.8506(2) Å, and V = 4067.1(2) Å$^3$.

| Atom | x | y | z | occ. | Uiso*100 (Å$^2$) |
|---|---|---|---|---|---|
| Fe | 0.3815(2) | 0.3518(2) | 0.1416(5) | 1.0 | 0.4(1) |
| O1 | 0.3293(3) | 0.2963(3) | 0.369(1) | 1.0 | 0.4(1) |
| O2 | 0.3001(3) | 0.2259(3) | 0.600(1) | 1.0 | 0.4(1) |
| O3 | 0.3550(3) | 0.2737(3) | 0.011(1) | 1.0 | 0.4(1) |
| C1 | 0.3189(3) | 0.2453(3) | 0.4267(9) | 1.0 | 0.51(6) |
| C2 | 0.3278(3) | 0.2063(3) | 0.2915(8) | 1.0 | 0.51(6) |
| C3 | 0.3441(3) | 0.2221(3) | 0.0908(8) | 1.0 | 0.51(6) |
| C4 | 0.3490(3) | 0.1809(3) | -0.030(1) | 1.0 | 0.51(6) |
| H | 0.3621(5) | 0.1922(5) | -0.173(2) | 1.0 | 1.8(3) |

Once completed, the same procedure was carried out for data obtained from the sample loaded with gas revealing both the site positions and orientations of framework bound $N_2O$ (see TABLES 4-6).

TABLE 4

Rietveld Refinement (10K) of $Fe_2(dobdc)$ $(N_2O)_{0.7}$. Fractional atomic coordinates, occupancies, and isotropic displacement parameters obtained from Rietveld refinement of structural model of the 0.35 $N_2O$ per $Fe^{2+}$ in the $Fe_2(dobdc)$ framework at 10K, space group R-3, a = 26.1660(4) Å, c = 6.8595(2) Å, and V = 4067.2(2) Å$^3$.

| Atom | x | y | z | occ. | Uiso*100 (Å$^2$) |
|---|---|---|---|---|---|
| Fe | 0.3819(1) | 0.3520(2) | 0.1437(4) | 1.0 | 0.49(5) |
| O1 | 0.3279(2) | 0.2957(2) | 0.3676(8) | 1.0 | 0.20(4) |
| O2 | 0.3010(2) | 0.2272(2) | 0.6019(7) | 1.0 | 0.20(4) |
| O3 | 0.3550(2) | 0.2738(2) | 0.0084(8) | 1.0 | 0.20(4) |
| C1 | 0.3193(2) | 0.2463(2) | 0.4292(7) | 1.0 | 0.42(2) |
| C2 | 0.3275(2) | 0.2063(2) | 0.2887(7) | 1.0 | 0.42(2) |
| C3 | 0.3438(2) | 0.2213(2) | 0.0924(7) | 1.0 | 0.42(2) |
| C4 | 0.35061(2) | 0.1817(2) | −0.0272(7) | 1.0 | 0.42(2) |
| H | 0.3619(4) | 0.1930(3) | −0.1712(15) | 1.0 | 1.3(2) |
| O11 | 0.471(1) | 0.358(1) | 0.272(4) | 0.22(1) | 1.6(8) |
| N12 | 0.5174(5) | 0.3960(4) | 0.2071(17) | 0.371(7) | 2.9(3) |
| N13 | 0.5607(6) | 0.4314(6) | 0.1533(26) | 0.223(6) | 1.6(4) |
| N11a | 0.4718(9) | 0.3605(9) | 0.2628(32) | 0.161(7) | 1.1(6) |
| O13a | 0.562(2) | 0.433(2) | 0.146(7) | 0.16(1) | 3(1) |

TABLE 5

Rietveld Refinement (10K) of $Fe_2(dobdc)$ $(N_2O)_{1.2}$. Fractional atomic coordinates, occupancies, and isotropic displacement parameters obtained from Rietveld refinement of structural model of the 0.60 $N_2O$ per $Fe^{2+}$ in the $Fe_2(dobdc)$ framework at 10K, space group R-3, a = 26.1577(4) Å, c = 6.8671(2) Å, and V = 4069.1(2) Å$^3$.

| Atom | x | y | z | occ. | Uiso*100 (Å$^2$) |
|---|---|---|---|---|---|
| Fe | 0.3829(1) | 0.3523(2) | 0.1428(5) | 1.0 | 0.94(5) |
| O1 | 0.3268(2) | 0.2945(2) | 0.3667(8) | 1.0 | 0.17(4) |
| O2 | 0.3019(2) | 0.2274(2) | 0.6000(7) | 1.0 | 0.17(4) |
| O3 | 0.3550(2) | 0.2733(2) | 0.0093(8) | 1.0 | 0.17(4) |
| C1 | 0.3189(2) | 0.2452(2) | 0.4273(7) | 1.0 | 0.86(2) |
| C2 | 0.3280(2) | 0.2059(2) | 0.2857(7) | 1.0 | 0.86(2) |
| C3 | 0.3446(2) | 0.2211(2) | 0.0933(7) | 1.0 | 0.86(2) |
| C4 | 0.3521(2) | 0.1833(2) | −0.0262(7) | 1.0 | 0.86(2) |
| H | 0.3602(3) | 0.1927(3) | −0.170(1) | 1.0 | 1.0(2) |
| O11 | 0.468(1) | 0.3533(9) | 0.272(3) | 0.232(5) | 1.5(7) |
| N12 | 0.5145(4) | 0.3915(4) | 0.211(2) | 0.532(7) | 7.9(4) |
| N13 | 0.5575(8) | 0.4275(8) | 0.152(4) | 0.232(5) | 6.8(7) |
| N11a | 0.4712(6) | 0.3560(6) | 0.264(2) | 0.310(6) | 5.5(5) |
| O13a | 0.5599(8) | 0.4296(8) | 0.151(3) | 0.310(6) | 3.3(6) |

TABLE 6

Rietveld Refinement (10K) of $Fe_2(dobdc)$ $(N_2O)_{2.5}$. Fractional atomic coordinates, occupancies, and isotropic displacement parameters obtained from Rietveld refinement (10K) of the $Fe_2(dobdc)$ dosed with 1.25 $N_2O$ per $Fe^{2+}$, space group R-3, a = 26.1243(5) Å, c = 6.87522(2) Å, and V = 4063.6(2) Å$^3$.

| Atom | x | y | z | occ. | Uiso*100 (Å$^2$) |
|---|---|---|---|---|---|
| Fe | 0.3828(2) | 0.3518(2) | 0.1479(6) | 1.0 | 0.95(9) |
| O1 | 0.3271(3) | 0.2952(3) | 0.3619(9) | 1.0 | 0.32(7) |
| O2 | 0.3006(3) | 0.2252(3) | 0.593(1) | 1.0 | 0.32(7) |
| O3 | 0.3554(3) | 0.2736(3) | 0.006(1) | 1.0 | 0.32(7) |
| C1 | 0.3194(2) | 0.2471(3) | 0.4234(9) | 1.0 | 0.81(4) |
| C2 | 0.3267(3) | 0.2057(3) | 0.2872(8) | 1.0 | 0.81(4) |
| C3 | 0.3457(2) | 0.2223(3) | 0.0956(9) | 1.0 | 0.81(4) |
| C4 | 0.3507(3) | 0.1808(3) | −0.0232(9) | 1.0 | 0.81(4) |
| H | 0.3632(3) | 0.1931(4) | −0.169(2) | 1.0 | 1.35(3) |
| O11 | 0.4704(7) | 0.3515(9) | 0.249(4) | 0.320(8) | 3.7(9) |
| N12 | 0.5176(3) | 0.3919(3) | 0.213(1) | 0.639(9) | 5.4(4) |
| N13 | 0.5610(5) | 0.4309(7) | 0.164(3) | 0.320(8) | 4.9(6) |
| N11a | 0.4711(5) | 0.3630(7) | 0.268(2) | 0.308(8) | 1.4(4) |
| N13a | 0.5657(6) | 0.4187(16) | 0.142(4) | 0.308(8) | 10.4(8) |
| N21 | 0.1468(8) | 0.1587(8) | 0.605(3) | 0.383(5) | 10.0(8) |
| N22 | 0.1620(7) | 0.1862(7) | 0.462(3) | 0.383(5) | 8.0(7) |
| O23 | 0.1744(1) | 0.2166(9) | 0.331(3) | 0.383(5) | 3.8(7) |
| N11aa | 0.5090(6) | 0.3732(7) | 0.333(2) | 0.310(5) | 2.4(5) |
| O11aa | 0.559(1) | 0.403(1) | 0.402(4) | 0.310(5) | 0.7(6) |
| N11ab | 0.4619(8) | 0.3481(8) | 0.285(3) | 0.310(5) | 3.7(6) |

Figure 13:
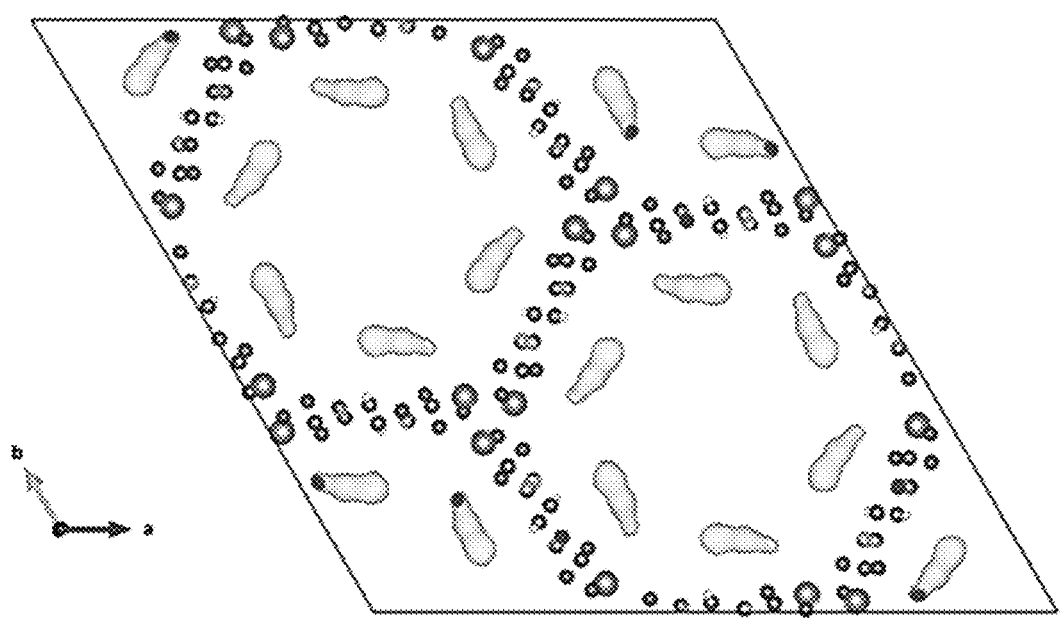
FIG. 13 shows a Fourier difference map of $Fe_2$(dobdc) ($N_2$O)$_{0.6}$. Fourier Difference Map of data obtained from $Fe_2$(dobdc) loaded with 0.35 $N_2$O per $Fe^{2+}$. Globules represent excess scattering density in the channels of the framework that result from $N_2$O molecules binding at the $Fe^{2+}$ site.

Unlike X-rays, neutrons are scattered from the nucleus allowing neighboring atoms with similar electron densities to exhibit nonlinear variations in scattering power. Nitrogen and oxygen have coherent scattering lengths of 9.36 fm and 5.80 fm, respectively. This implies that neutrons should be very sensitive to the atomic assignment of O and N, an especially important feature when considering the large esds associated with bond distances determined from position averaged powder data. Fourier Difference Analysis of the data obtained from the sample loaded with 0.35 $N_2O$ per $Fe^{2+}$ reveals that the $N_2O$ binds in an end-on fashion with a distance of approximately 2.40(2) A from the $Fe^{2+}$ and is angled with respect to the framework surface at 118(2)° (see FIG. 13). For assignment of the atoms responsible for binding to the metal site, both $Fe^{2+}$—O and $Fe^{2+}$—N binding were tried. First, the occupancies of the N—N—O atoms were constrained to be equal. Once a stable refinement was achieved, the occupancies of the individual atoms in the $N_2O$ molecule were allowed to vary independently of one another. In either case of M-O or M-N binding, the occupancies of both terminal $N_2O$ atoms deviated significantly from the average value and lead to an improvement in the overall refinement. The observed increase and/or decrease in the occupancies correlated with our expectations based on the known differences in scattering lengths of the O and N. The results imply that pure O or N coordination at the metal site was incorrect. Further, the structural model showed only average distances for both N—N and N—O, around 1.15 Å, and so a clear assignment of the binding mechanism of the $N_2O$ could not be made purely through assessment of bond distances. Considering all of these factors, the refinement with mixed O and N binding for the $N_2O$ molecules were performed revealing an average of approximately 60% O and 40% N at the open metal site. The intramolecular $N_2O$ angle was refined at a value of 178(2)°, which, within error of the neutron diffraction experiment, did not deviate from the expected linear geometry.

Figure 14:
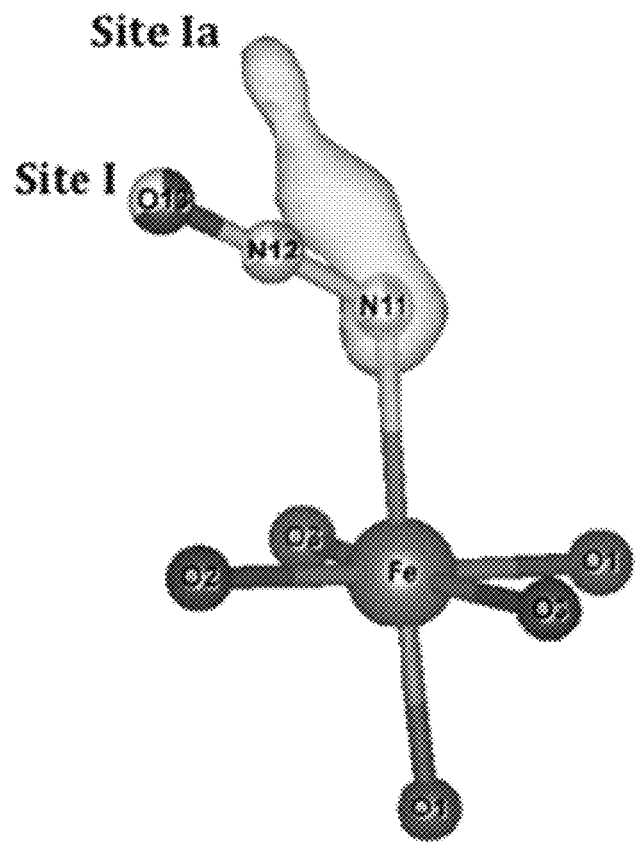
FIG. 14 shows a Fourier difference map of $Fe_2(dobdc)$ $(N_2O)_{2.5}$. Fourier Difference Map of data obtained from $Fe_2(dobdc)$ loaded with 1.25 $N_2O$ per $Fe^{2+}$. Globules represent excess scattering density in the channels of the framework that result from $N_2O$ molecules binding at the $Fe^{2+}$ site. There is a slight rearrangement from the site I $N_2O$ orientation, denoted site Ia, upon population of the secondary adsorption site.

At higher loadings (0.6 and 1.25 equivalents of $N_2O$), disorder at the metal and the presence of multiple binding sites prevented accurate determination of the binding mode (see FIG. 14). In particular, upon increasing the $N_2O$ loading to 0.6 and then 1.25 $N_2O$ per $Fe^{2+}$, there was further population of the site I molecule and then the subsequent introduction of a secondary adsorption site. Population of binding site II appeared to induce a rearrangement of the site I molecule, referred to from this point forward as site Ia (see FIG. 14). While the data was not good enough to distinguish the binding mechanism in these two different orientations, a significant change in the angle of the $N_2O$ with respect to the framework surface was seen, which changes from ~120° to ~145°. Intermolecular distances between site I and II, on the order of 2.2 Å, are significantly shorter than the sum of the van der Waals radii for N (1.55 Å) and/or O (1.52 Å). As a result, this interaction was expected to be quite unfavorable. Further, the refined occupancies of site II, ~34%, and site I, ~68%, support the idea that the two sites are never simultaneously occupied.

In situ transmission-mode FTIR charcterization of $Fe_2$(dobdc). Contact with 40 mbar of $N_2O$ causes the appearance of extremely strong bands in the 2280-2160 $cm^{-1}$ spectral range, associated with $\nu$(N—N) of $N_2O$, while the rest of the IR spectrum was substantially unaffected (see FIG. 15A). Dominant absorptions due to the framework modes below 1600 $cm^{-1}$ do not allow the monitoring of the $\nu$(N—O) band in $N_2O$, which was expected to be around 1286 $cm^{-1}$. The spectrum profile verified the formation of a condensed phase inside the $Fe_2$(dobdc) channels, as the $\nu$(N—N) band does not present the expected profile of a free linear rotator (P and R branches with the lack of the pure vibrational transition, Q branch).

FIG. 15B illustrates in detail the spectral range due to $\nu$(N—N) band (spectra reported after background subtraction). The spectrum at highest coverage (blue curve) is characterized by a very intense band, ascribable to the $\nu$(N—N) in $N_2O$ molecule, behaving as an hindered rotator. The maximum was observed at 2226 $cm^{-1}$, a position very close to that expected for the fundamental transition of pure $N_2O$ molecule (2224 $cm^{-1}$). The very small blue shift with respect to the position of $N_2O$ gas indicated that $N_2O$ interacts weakly with the Fe(II) species, giving rise to a physically adsorbed (liquid-like) phase. The main peak was accompanied by further components at higher (clear maximum at 2240 $cm^{-1}$) and lower (broad features at 2220, 2214 and 2206 $cm^{-1}$) frequencies, suggesting that, at the measuring temperature (beam temperature), $N_2O$ molecules may still partially retain their roto-vibrational profile (compare the spectra with that obtained in case of gaseous $N_2O$, blue dotted spectrum).

In case of Fe-silicalite the appearance of a doublet at 2282 $cm^{-1}$ and at 2248 $cm^{-1}$ was assigned to the formation of two slightly different Fe—$N_2O$ adducts, while a component at 2226 $cm^{-1}$ was associated to the formation of weaker adducts with Brønsted sites. In the present case similar assignments were discarded, as all the above-mentioned signals disappeared at the same rate upon outgassing at room temperature (see light grey spectra in FIG. 15B). The total reversibility of these components further confirmed the weak nature of the interaction of $N_2O$ with the Fe(II) sites in $Fe_2$(dobdc) sample.

Prolonged heating in $N_2O$ at 60° C. gave rise to a spectrum characterized by a strong band at 3678 $cm^{-1}$ and by a clear component at 670 $cm^{-1}$. The peak at 3678 $cm^{-1}$ can be associated to a $\nu$(O—H) specie and the component at 670 $cm^{-1}$ can be ascribed to a $\nu$(Fe—OH) specie. The formation of these hydroxide species was associated with the reactivity of $N_2O$, as indicated by the decrease in intensity for the adsorbed $N_2O$ band (see FIG. 16A).

Cyclohexadiene Reactivity of $Fe_2(OH)_{0.6}$(dobdc). Neat cyclohexadiene (160 mg, 2.0 mmol) was added to $Fe_2(OH)_{0.6}$(dobdc) (66 mg, 0.125 mmol Fe(III), determined by Mössbauer) and allowed to react for 24 hours, during which a visible color change from red-brown to light yellow was observed. The sample was then extracted with $CD_3CN$ (3×1 mL), and the products analyzed by 1H NMR using 1,2,4,5-tetramethylbenzene as an internal standard. Benzene as the sole product was obtained in quantitative yield.

Reactivity of $Fe_2$(dobdc) and $Fe_{0.1}Mg_{1.9}$(dobdc) with $N_2O$ and $C_2H_6$.

In a typical flow-through experiment, a mixture of gases (2 mL/min $N_2O$, 10 mL/min $C_2H_6$, and 8 mL/min Ar for a total flow 20 mL/min) was flowed over a packed bed of metal-organic framework (50 to 100 mg) contained within a glass column. The column was heated to 75° C. for twenty-four hours, after which the products were extracted with $CD_3CN$ (3×1 mL) and analyzed by 1H NMR using 1,4-dichlorobenzene as an internal standard. While a cold bath maintained at −78° C. was installed downstream of the glass reactor in order to collect condensable organic products, at the temperatures tested all the products appear to remain bound to the framework. Yield for $Fe_{0.1}Mg_{1.9}$(dobdc): 9.5:1 ethanol:acetaldehyde, 60% yield based on Fe.

In a typical batch experiment, a Parr bomb was charged with 50-100 mg of $Fe_{0.1}Mg_{1.9}$(dobdc), $N_2O$ (1.5 bar), and $C_2H_6$ (7.5 bar) and heated to 75° C. in a sand bath. After twenty-four hours, the bomb was cooled and the products extracted with $CD_3CN$. Yield for $Fe_{0.1}Mg_{1.9}$(dobdc): 25:1 ethanol:acetaldehyde, 1.6 turnovers based on Fe. In a typical experiment, this corresponds to functionalization of roughly 1% of the ethane molecules.

Reactivity of $Fe_2$(Dobpdc) with $N_2O$ and Ethane:

Heating $Fe_{0.25}Mg_{1.75}$(dobpdc) in a bomb with 1.5 bar of $N_2O$ and 8.5 bar of ethane at 75° C. results in a 13:1 mixture of ethanol:acetaldehyde. The overall yield is ~70% with respect to iron, due to catalyst decomposition into an inactive Fe(III) phase.

Reactivity of $Fe_2$(Dobpdc) with Cyclohexane and Iodosylarene:

At room temperature, 1 equiv. of $Fe_2$(dobpdc) was combined with 2 equiv. of the oxidant 2-(tert-butylsulfonyl)iodosylbenzene and 20 equiv. of cyclohexane in $CD_3CN$. Analysis of the products shows that cyclohexanol and cyclohexanone were produced in a 1.2:1 ratio.

Figure 29A:
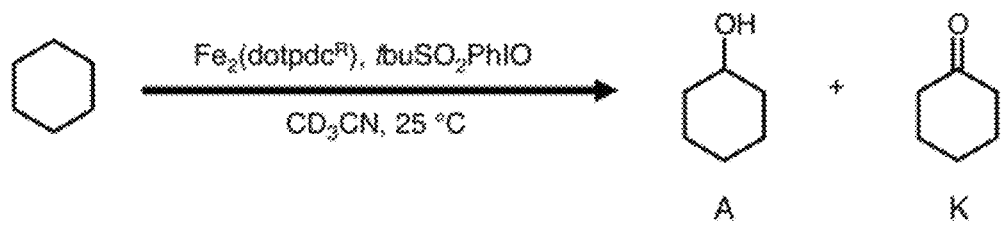
FIG. 29A-B shows (A) A reaction scheme. The framework is combined with 5 to 20 equiv of the oxidant, $tBuSO_2PhIO$, and 150 equiv. of cyclohexane, to form cyclohexanol and cyclohexanone. (B) A:K ratios obtained from $Fe_2(dotpdc)^R$ (R=H, F, $CH_3$, and tBu). For the unsubstituted derivative, the A:K ratio is roughly 3:1; however, this changes to greater than 8:1 for the tBu-functionalized ligand.
Figure 29B:
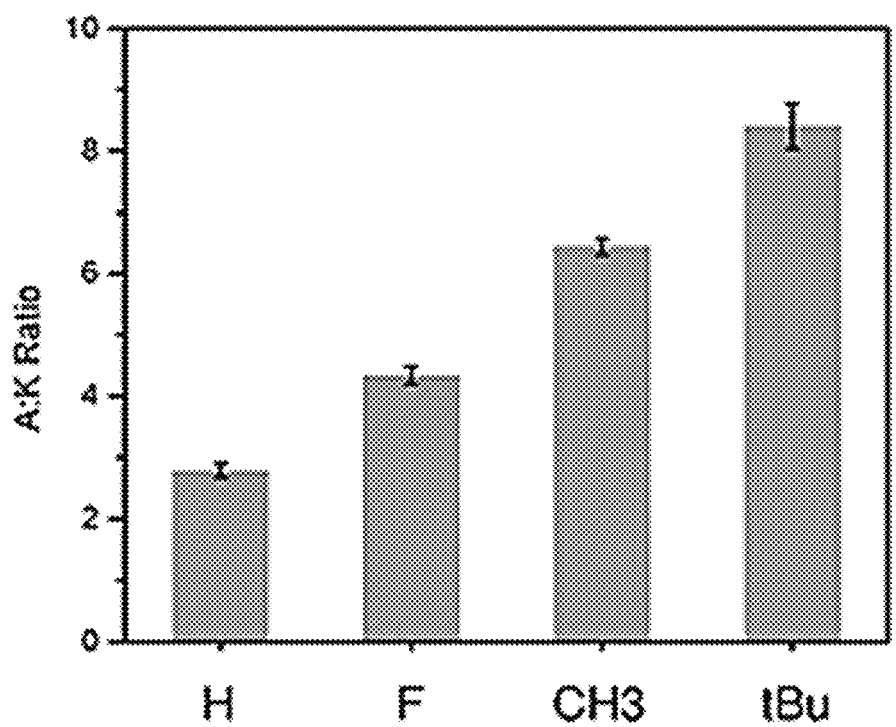

Reactivity of $Fe_2$(Dotpdc) with Cyclohexane and Iodosylarene:

At room temperature, 1 equiv. of $Fe_2$(dotpdc$^R$) was combined with 5 to 20 equiv. of the oxidant 2-(tert-butylsulfonyl)iodosylbenzene and 150 equiv. of cyclohexane in $CD_3CN$ (see FIG. 29a). After 1.5 hours, analysis of the products shows that exclusively cyclohexanol and cyclohexanone were produced, in nearly quantitative yields based on oxidant. The alcohol:ketone (A:K) ratios depended on the identity of the organic ligand (see FIG. 29b). It was found that more hydrophobic, alkyl-containing ligand substituents led to higher A:K ratios. Solution- and gas-phase studies suggest the ligand substituents alter the pore environment and help modulate the cyclohexane concentration inside the pore. Briefly, alkyl substituents interact more favorably with cyclohexane, leading to higher local cyclohexane concentrations and greater A:K selectivities. This can be potentially extended from cyclohexane to other hydrocarbons.

Control Experiments.

No products were observed if $N_2O$, ethane, or $Fe_2$(dobdc)/$Fe_{0.1}Mg_{1.9}$ (dobdc) was removed from the reaction mixture. The same flow-through and batch experiments performed on $Mg_2$(dobdc) led to no observed products. The same conditions applied to $Fe_2$(dobdc) diluted in $Mg_2$(dobdc) did not lead to a clean reaction (unlike $Fe_{0.1}Mg_{1.9}$ (dobdc)). Finally, an autoxidation process was ruled out by repeating the batch experiment with added $O_2$ (1 bar), $N_2O$ (1.5 bar), and $C_2H_6$ (7.5 bar). The yield was significantly lower (11% based on iron) and the ethanol selectivity much worse (1:2.67 ethanol:acetaldehyde), indicating that the reported reactivity is not due to autoxidation.

Analyzing the Reversible Binding of N2O to Fe$_2$(dobdc).

The binding of nitrous oxide to 1 under conditions in which the Fe—N$_2$O interaction is reversible was first investigated. Experimental studies on the coordination chemistry of N$_2$O are scarce, as metal-N$_2$O adducts are challenging to synthesize due to the poor σ-donating and π-accepting properties of the molecule. Indeed, of the several proposed binding modes, only one-end-on, $\eta^1$-N-has been structurally characterized in a molecular complex. To establish the coordination mode of N$_2$O in 1, powder neutron diffraction data, which are very sensitive to the atomic assignment of O and N, were collected on a sample dosed with various loadings of N$_2$O. At low loadings, the best fit was an average of approximately 60% $\eta^1$-O and 40% $\eta^1$-N coordination, with Fe—N$_2$O distances of 2.42(3) and 2.39(3) A, respectively. In both cases, a bent Fe—N$_2$O angle close to 120° was observed (see FIG. 3B). Density functional theory (DFT) studies of N$_2$O-bound 1 using the M06 functional show excellent agreement with experimental (see FIG. 4A-B). Furthermore, these calculations predict the $\eta^1$-O coordination mode to be favored over the $\eta^1$-N mode by just 1.1 kJ/mol (see TABLES 7 and 8). This is consistent with the nearly equal population split observed, although the magnitude of the difference is smaller than the reliability of the calculations.

TABLE 7

Calculated relative energies (kJ/mol) for N$_2$O bound to the Fe(II) site of the 88-atom cluster. The relative energies of $\eta^1$-N and $\eta^1$-O coordination modes are computed using M06-L and M06 density functionals with the def2-TZVP and SDD(Fe, Zn), 6-31G(d) (C, H, O, N) basis sets. The level of optimization is opt6.

| Functional mode | Binding | SDD (Fe, Zn), 6-31G(d) (C, H, O, N) | def2-TZVP |
|---|---|---|---|
| M06-L | $\eta^1$-O | 0.0 | 0.0 |
|  | $\eta^1$-N | −4.6 | −9.5 |
| M06 | $\eta^1$-O | 0.0 | 0.0 |
|  | $\eta^1$-N | 1.1 | −4.5 |

TABLE 8

Binding energies$^a$ (kJ/mol) of $\eta^1$-N and $\eta^1$-O coordination modes of N$_2$O bound to the iron(II) site of the 88-atom cluster. The calculations were done using M06-L and M06 density functionals with SDD(Fe, Zn), 6-31G(d) (C, H, O, N) basis set. The level of optimization is opt6.

| Functional | Binding mode | Binding energy (kJ/mol) |
|---|---|---|
| M06-L | $\eta^1$-O | 41.4 |
|  | $\eta^1$-N | 46.1 |
| M06 | $\eta^1$-O | 45.6 |
|  | $\eta^1$-N | 44.5 |

$^a$Binding Energy = E(cluster) + E(N$_2$O) − E(complex)

While $\eta^1$-O coordination with a bent Fe—O—N angle has been proposed in a variety of systems ranging from isolated metal atoms to iron zeolites, $\eta^1$-N coordination with a bent Fe—N—N angle is much more unusual. It suggests little n-back-bonding from the metal d-orbitals into the π* of N$_2$O, in contrast to previously reported vanadium and ruthenium-N$_2$O adducts, which have linear metal-N—N—O geometries and for which n-interactions have been postulated as significant contributors to the stability of the complexes. The bent geometry, long Fe—N$_2$O bond length, and mixed N- and O-coordination indicate N$_2$O was bound only weakly to the iron(II) centers in the framework, a hypothesis corroborated by in-situ transmission-mode infrared spectroscopy. Spectra collected on a thin-film of 1 dosed at room temperature with N$_2$O displayed a maximum at 2226 cm$^{-1}$, which was very close to the fundamental v(N—N) transition for unbound N$_2$O (2224 cm$^{-1}$), suggesting a physically adsorbed phase with little to no perturbation of the N$_2$O molecule (see FIG. 15A-B). As expected, this interaction is fully reversible, and the band completely disappears under applied vacuum. Consistent with these experimental results, DFT studies calculate binding energies of 45.6 and 44.5 kJ/mol for the $\eta^1$-O and $\eta^1$-N modes, respectively, with a natural bond order analysis showing weak back-bonding in both configurations (see TABLE 9).

TABLE 9

Natural bond analysis of $\eta^1$-N and $\eta^1$-O coordination modes of N$_2$O bound to the iron(II) site of the 88-atom cluster.

| Binding mode | % Back-bonding |
|---|---|
| $\eta^1$-O | 42% |
| $\eta^1$-N | 43% |

Figures 17A, 17B:
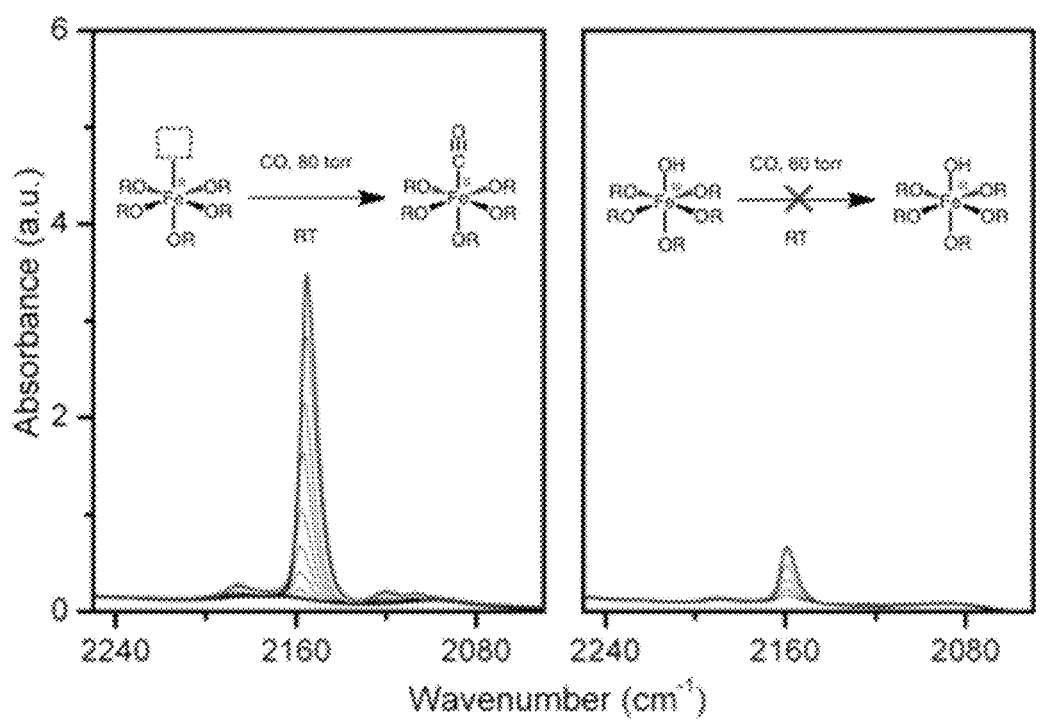
FIG. 17A-B presents the results of CO titration experiments before and after heating $Fe_2(dobdc)$ in the presence of $N_2O$. (A) CO dosed on an activated sample of bare $Fe_2$ (dobdc) (B) CO dosed on a sample that has contacted $N_2O$ at room temperature for one day, and then overnight at 60° C. shows that the number of open Fe(II) sites has been reduced dramatically (less than 10% remaining).
Figure 18A:
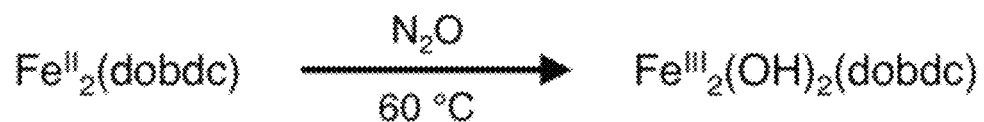
FIG. 18A-B provides for the preparation and Mössbauer spectrum of $Fe_2(OH)_2(dobdc)$. (A) Reaction scheme for the preparation of 2 from $Fe_2(dobdc)$. (B) Mössbauer spectrum of 2, with the fit in black. The red component has parameters consistent with high-spin Fe(III) (5=0.40(2) mm/s, IAEQ, =0.96(1) mm/s, area=80(2)%). A minor component (green) is assigned as unreacted Fe(II) sites, and another minor component (purple) is assigned as an amorphous Fe(III) decomposition product.
Figure 18B:
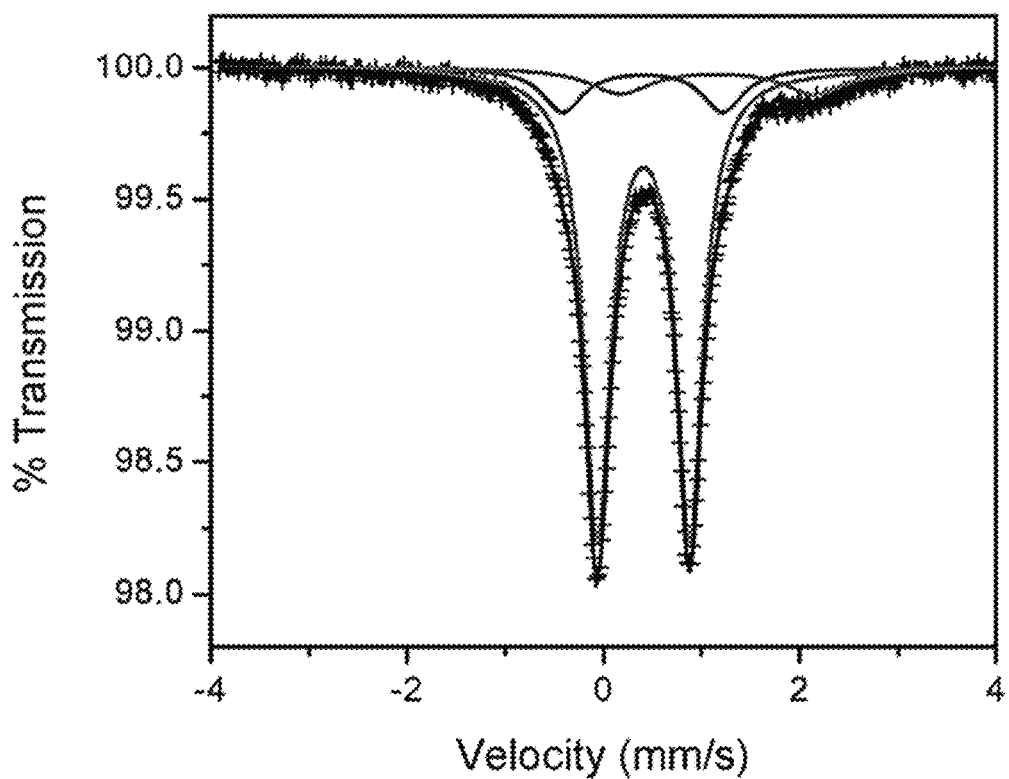
Figure 19:
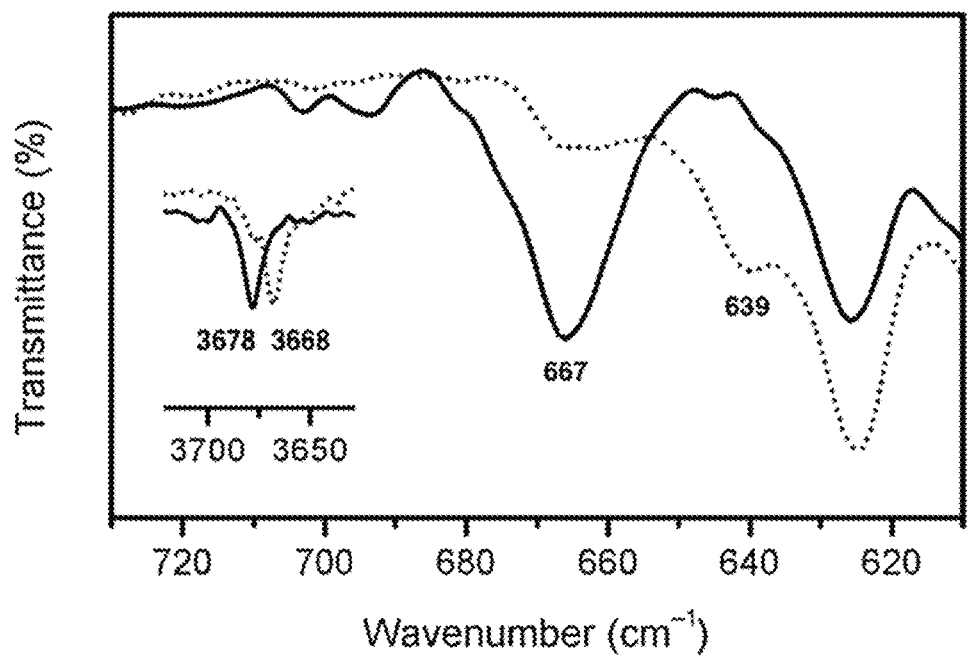
FIG. 19 provides an ATR-FTIR spectra of $Fe_2(OH)_{0.6}$ (dobdc) (black) and $Fe_2(^{18}OH)_{0.6}(dobdc)$ (dotted red).
Figure 20A:
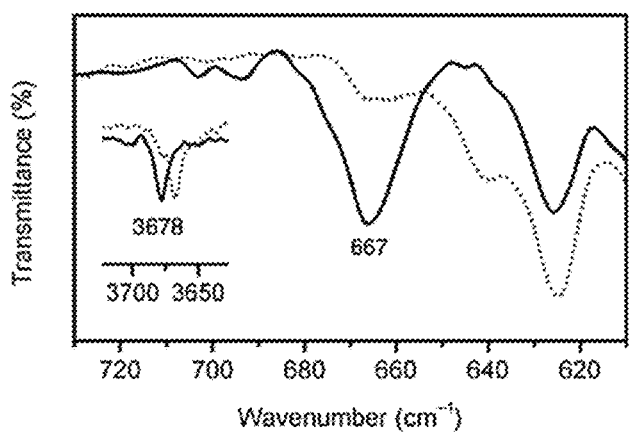
FIG. 20A-B provides the structure and infrared spectrum of $Fe_2(OH)_2(dobdc)$. (A) Infrared spectrum of a partially oxidized sample, $Fe_2(OH)_{0.6}(dobdc)$ (black) and $Fe_2(^{18}OH)_{0.6}(dobdc)$ (dotted red). The peaks at 667 and 3678 $cm^{-1}$ shift to 639 and 3668 $cm^{-1}$, respectively, upon $^{18}O$ labeling. (B) The structure of $Fe_2(OH)_2(dobdc)$ obtained by powder X-ray diffraction data (100 K). Selected interatomic distances (A) for 1: Fe—O1=1.92(1); Fe—O2=2.01(1); Fe—O3=2.08(1); Fe—O4=2.04 (1); Fe—O5=2.04(1); Fe—O6=2.20(1); Fe—Fe=3.16(1).
Figure 20B:
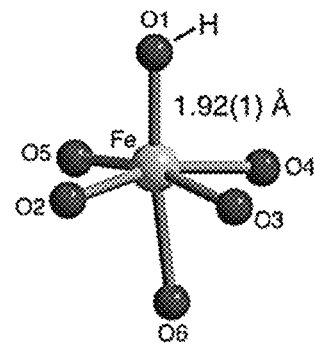
Figure 21:
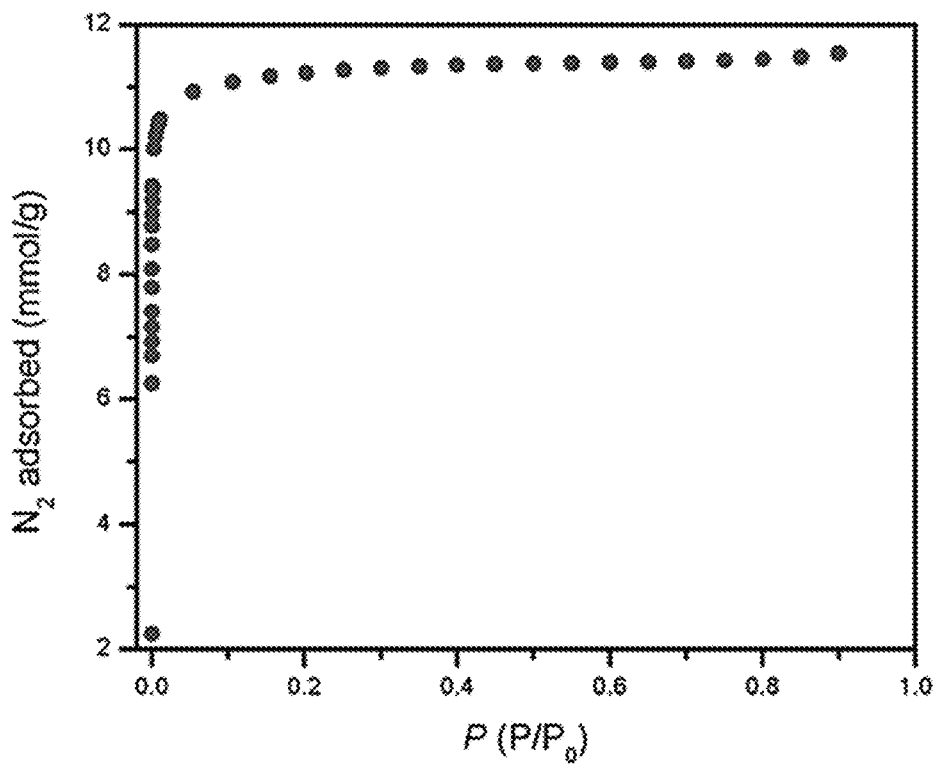
FIG. 21 provides a $N_2$ adsorption isotherm in $Fe_2(OH)_2$ (dobdc) at 77 K.
Figure 22:
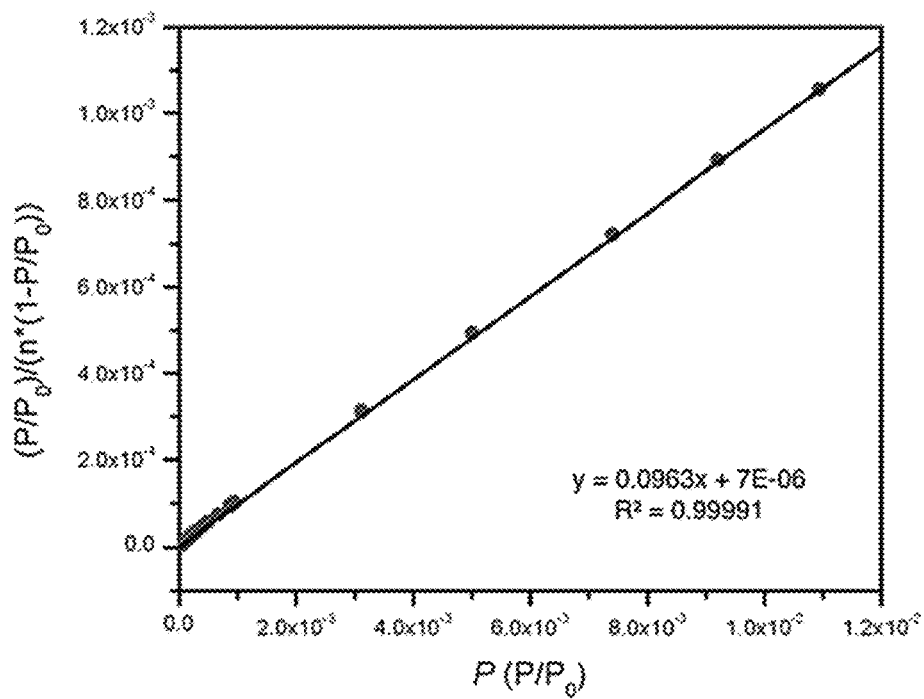
FIG. 22 presents a BET plot of the $N_2$ adsorption isotherm in $Fe_2(OH)_2(dobdc)$ at 77 K. The black line represents a linear best fit of the data points (circles). Inset: parameters for the linear best fit and resulting constants for calculation of the BET surface area.
Figure 23:
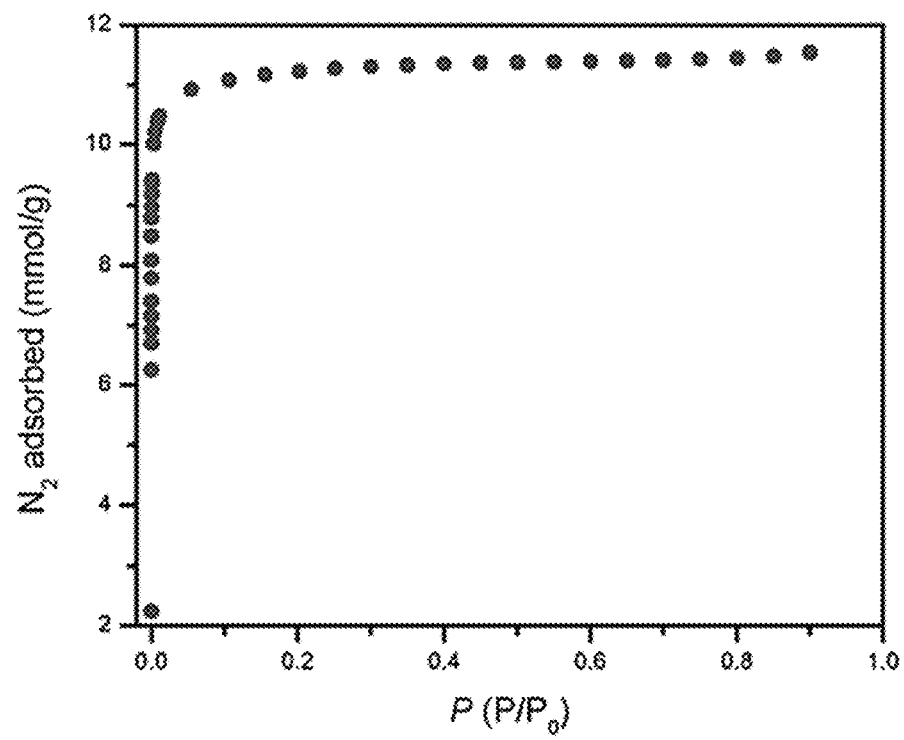
FIG. 23 provides a $N_2$ adsorption isotherm in $Fe_{0.1}Mg_{1.9}$ (dobdc) at 77 K.
Figure 24:
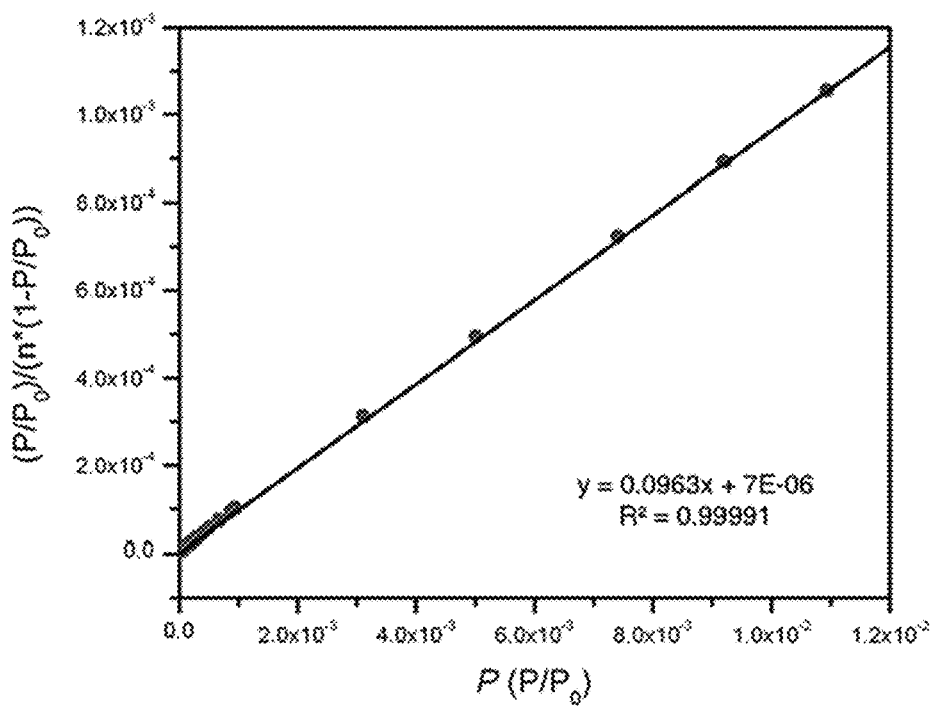
FIG. 24 presents a BET plot of the $N_2$ adsorption isotherm in $Fe_{0.1}Mg_{1.9}$ (dobdc) at 77 K. The black line represents a linear best fit of the data points (circles). Inset: parameters for the linear best fit and resulting constants for calculation of the BET surface area.

Upon heating the N$_2$O-dosed framework to 60° C., the material underwent a drastic color change from bright green to dark red-brown that was suggestive of oxidization. In addition, in situ infrared studies using CO as a probe molecule showed that the open metal sites, which coordinate CO strongly, had been almost entirely consumed (see FIG. 17A-B). Characterization of the resulting product was consistent with the formation of Fe$_2$(OH)$_2$(dobdc) (2), in which each iron center is in the +3 oxidation state and bound to a terminal hydroxide anion (see FIG. 18A). Compound 2 was likely formed via a fleeting iron-oxo intermediate, which rapidly underwent H-atom abstraction, although the source of the H-atom has not been yet determined. Mössbauer spectroscopy was used to probe the local environment of the iron centers in the oxidized material. The $^{57}$Fe Mössbauer spectrum of 2 consists of a doublet characterized by an isomer shift (δ) of 0.40(2) mm/s and a quadrupole splitting (|ΔE$_Q$|) of 0.96(1) mm/s (see FIG. 18B). The isomer shift for the iron centers in 2 is similar to the parameters obtained for the peroxide-coordinated iron(III) centers in Fe$_2$(O$_2$)(dobdc), and is consistent with other high-spin heme and nonheme iron(III) species. In addition, the infrared spectrum of 2 showed the appearance of two new bands as compared to the unoxidized framework, which was assigned as Fe—OH (667 cm$^{-1}$) and O—H (3678 cm$^{-1}$) vibrations. These bands shift to 639 and 3668 cm$^{-1}$, respectively, when N$_2$$^{18}$O is employed for the oxidation; the observed differences of 28 and 10 cm$^{-1}$ were very close to the theoretical isotopic shifts of 27 and 12 cm$^{-1}$ predicted by a simple harmonic oscillator model (see FIG. 20A). Partial oxidation of the framework was achieved by heating at 35° C. for 12 h, leading to the formation of Fe$_2$(OH)$_{0.6}$(dobdc) (2'), which has a similar infrared spectrum (though the bands associated with Fe—OH are less intense) and Mössbauer parameters (see TABLE 10).

TABLE 10

Mössbauer spectral parameters.

| Sample | δ, mm/s | |ΔE$_Q$| mm/s | Γ, mm/s | Area (%) | Assignment |
|---|---|---|---|---|---|
| Fe$_2$(OH)$_2$(dobdc) (1) | 0.40(2) | 0.96(1) | 0.34(1) | 80(2) | Fe$^{III}$—OH |
|  | 0.40(2) | 1.80(6) | 0.50(1) | 13(2) | Unknown Fe$^{III}$ |
|  | 1.21(6) | 1.77(9) | 0.57(15) | 7(2) | Fe$^{II}$ |
| Fe$_2$(OH)$_{0.6}$(dobdc) (1') | 0.44(2) | 0.95(4) | 0.41(4) | 30(3) | Fe$^{III}$—OH |
|  | 1.08(1) | 1.98(2) | 0.44(3) | 70(4) | Fe$^{II}$ |

TABLE 10-continued

Mössbauer spectral parameters.

| Sample | δ, mm/s | $|\Delta E_Q|$ mm/s | Γ, mm/s | Area (%) | Assignment |
|---|---|---|---|---|---|
| $Fe_{0.1}Mg_{1.9}$(dobdc) (2) | 1.08(1) | 2.25(1) | 0.31(2) | 100 | $Fe^{II}$ |
| $Fe_{0.1}Mg_{1.9}$(dobdc) (after $N_2O/C_2H_6$ treatment) | 0.45(1) | 1.08(3) | 0.51(2) | 89(4) | $Fe^{III}$—OH |
| | 1.07(7) | 2.24(11) | 0.34(12) | 11(3) | $Fe^{II}$ |

The framework maintained both crystallinity and porosity after oxidation, with a Brunauer-Emmett-Teller (BET) surface area of 1013 m²/g and a Langmuir surface area of 1171 m²/g. Rietveld analysis of powder X-ray diffraction data collected at 100 K on 2 firmly established the presence of a new Fe—O bond, but did not reveal whether a hydrogen atom is present. However, the Fe—OH bond distance of 1.92(1) Å, which is consistent with the bond lengths of previously reported octahedral iron(III)-hydroxide complexes (1.84-1.93 Å) (see FIG. 18B). In addition, the trans Fe—$O_{axial}$ bond was slightly elongated (Fe—$O_{axial}$=2.20(1) Å; average Fe—$O_{equatorial}$=2.04(1) Å), with the iron center shifted slightly out of the plane of the four equatorial oxygen atoms by 0.23(1) Å. EXAFS analysis of the same sample, as well as periodic DFT calculations, provide bond lengths that were consistent with those obtained from the diffraction data (see TABLE 11 and TABLE 12).

TABLE 11

EXAFS curve fitting parameters for $Fe_2$(dobdc) and comparison with bond lengths obtained by PXRD.

| Path | PXRD R (Å) | EXAFS R (Å) | N | σ² (Å²) | R (%) |
|---|---|---|---|---|---|
| Fe—O | 2.10ᵃ | 2.06(1) | 5 | 0.010(2) | 1.0 |
| Fe—C | 3.05ᵃ | 3.07(5) | 5 | 0.003(4) | $\Delta E_0 = 3.1$ |
| Fe—Fe | 3.00(2) | 2.96(3) | 2 | 0.010(6) | |
| Fe—OC | 3.23ᵃ | 3.22(8) | 10 | 0.010(11) | |

TABLE 12

EXAFS curve fitting parameters for 2 and comparison with bond lengths obtained by DFT (periodic PBE + U) and PXRD (100K data). Note that although the PXRD and EXAFS are in good agreement overall, there are dissimilarities, especially in the Fe— Oaxial bond lengths for 2. This is because while EXAFS can be used to obtain first-shell distances with great accuracy, it is much more limited when resolution of different bond lengths is needed, especially when the scatterers have both a similar distance and atomic number, as is the case in 2.

| Path | DFT R (Å) | PXRD R (Å) | EXAFS R (Å) | N | σ² (Å²) | R (%) |
|---|---|---|---|---|---|---|
| Fe—OH | 1.84 | 1.92(1) | 1.85(3) | 1 | 0.009(1) | 1.1 |
| Fe—$O_{eq}$ | 2.02ᵃ | 2.04ᵃ | 2.02(1) | 4 | 0.009(1) | $\Delta E_0 = 2.70$ |
| Fe—$O_{ax}$ | 2.27 | 2.20(1) | 2.33(4) | 1 | 0.009(1) | |
| Fe—C | 3.01ᵃ | 3.03ᵃ | 2.95(1) | 5 | 0.009(1) | |
| Fe—Fe | 3.23 | 3.16(1) | 3.15(9) | 2 | 0.016(4) | |
| Fe—O—C | 3.19ᵃ | 3.21ᵃ | 3.16(14) | 10 | 0.006(8) | |

Bold numbers are fixed values.
Numbers in parentheses show uncertainty.
ᵃAveraged values.

Surprisingly, the iron(III)-hydroxide species was capable of activating weak C—H bonds. When the partially oxidized sample 2' was exposed to 1,4-cyclohexadiene (C—H bond dissociation energy of 305 kJ/mol) at room temperature, benzene was produced as the sole product in quantitative yield. In the process, the iron of the framework converted entirely back to iron(II), as determined by Mössbauer spectroscopy. Such reactivity is rare for iron(III)-hydroxide compounds. For instance, lipoxygenase, an enzyme that converts 1,4-dienes into alkyl hydroperoxides, is believed to proceed through a non-heme ferric hydroxide intermediate, and several molecular lipoxygenase mimics have also been reported to activate the C—H bond of 1,4-cyclohexadiene and other 1,4-dienes.

Because the isolation of an iron(III)-hydroxide product from a reaction employing a two-electron oxidant strongly suggests the intermediacy of an iron(IV)-oxo species, the oxidation in the presence of a hydrocarbon substrate containing stronger C—H bonds, specifically ethane (C—H bond dissociation energy of 423 kJ/mol) was carried out, hoping to intercept the oxo species before its decay. Indeed, flowing an $N_2O$:ethane:Ar mixture (10:25:65) over the framework at 75° C. led to the formation of various ethane-derived oxygenates, including ethanol, acetaldehyde, diethyl ether, and other ether oligomers, as determined by 1H NMR spectroscopy of the extracted products. It was hypothesized that the complex mixture of products was related to the close proximity of reactive iron centers, which are 8.75(2) Å and 6.84(1) Å apart across and along a channel, respectively, in 1. To avoid oligomerization and over-oxidation, a mixed-metal metal-organic framework, $Fe_{0.1}Mg_{1.9}$(dobdc) (3), in which the iron(II) sites are diluted with redox-inactive magnesium(II) centers, was synthesized. The BET surface area of 1670 m²/g for this material falls between the surface areas of the pure iron and pure magnesium frameworks (1360 and 1800 m²/g, respectively) While determining the exact distribution of metal centers in heterometallic metal-organic frameworks is challenging, the unit cell parameters of 3 are also in between those of $Fe_2$(dobdc) and $Mg_2$(dobdc) (see TABLE 13), suggesting the formation of a solid solution rather than a mixture of two separate phases.

TABLE 13

Unit cell parameters (298K) of $Fe_2$(dobdc), $Fe_xMg_{2-x}$(dobdc), and $Mg_2$(dobdc). The unit cell constants and volumes of $Fe_{0.1}Mg_{1.9}$(dobdc) and $Fe_{0.44}Mg_{1.56}$(dobdc) are in between that of $Fe_2$(dobdc) and $Mg_2$(dobdc) and show a linear correlation with magnesium content, in agreement with Vegard's Law for solid solutions.

| | $Fe_2$ (dobdc) | $Fe_{0.44}Mg_{1.56}$ (dobdc) | $Fe_{0.1}Mg_{1.9}$ (dobdc) | $Mg_2$ (dobdc) |
|---|---|---|---|---|
| a (Å) | 26.1603(10) | 25.9964(8) | 25.9485(9) | 25.9111(20) |
| c (Å) | 6.8657(4) | 6.8465(4) | 6.8574(4) | 6.8687(12) |
| V (Å³) | 4069.1(3) | 4007.1(4) | 3998.7(3) | 3993.7(7) |

Additionally, the Mössbauer spectrum of 3 showed sharp doublets with a significantly different quadrupole splitting than the all-iron analogue (2.25(1) mm/s versus 2.02(1) mm/s in $Fe_2$(dobdc); see TABLE 10), indicating that the iron centers in the magnesium-diluted framework were in an altered, but uniform, environment. Thus, 3 is likely best described as containing either isolated iron centers or short multi-iron segments dispersed evenly throughout a magnesium-based framework.

Figure 25:
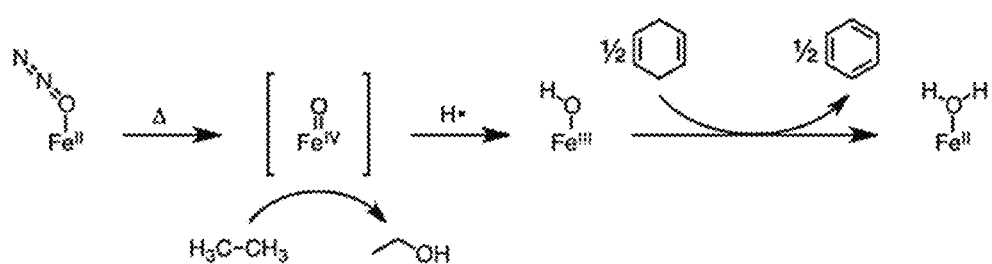
FIG. 25 demonstrates $N_2O$ activation and reactivity of $Fe_2(dobdc)$.

Exposure of 3 to $N_2O$ and ethane under the same flow-through conditions yielded the exclusive formation of ethanol and acetaldehyde in a 10:1 ratio, albeit in low yield (60% with respect to iron). Gas chromatography analysis of the headspace revealed no ethanol, acetaldehyde, or CO, suggesting the products remain bound to the framework (either at open iron or open magnesium sites), which would likely explain the high ethanol selectivity. While the framework was still highly crystalline after $N_2O$/ethane treatment, Mössbauer spectroscopy revealed that roughly 90% of the iron centers have decayed into a species with similar spectral parameters as 2 (see FIG. 5 and TABLE 10). It was postulated that the formation of iron(III)-hydroxide or alkoxide decay products prematurely halted the catalytic cycle, resulting in substoichiometric yields of hydroxylated product (see FIG. 25). Because glass can be a source of H-atoms, the reaction was subsequently repeated in a batch, rather than flow-through mode, in a Teflon-lined stainless-steel bomb, which produced both higher yields with respect to iron (turnover number=1.6) and selectivities (25:1 ethanol:acetaldehyde), showing that the system can indeed be modestly catalytic if competing substrates were excluded.

Figure 26:
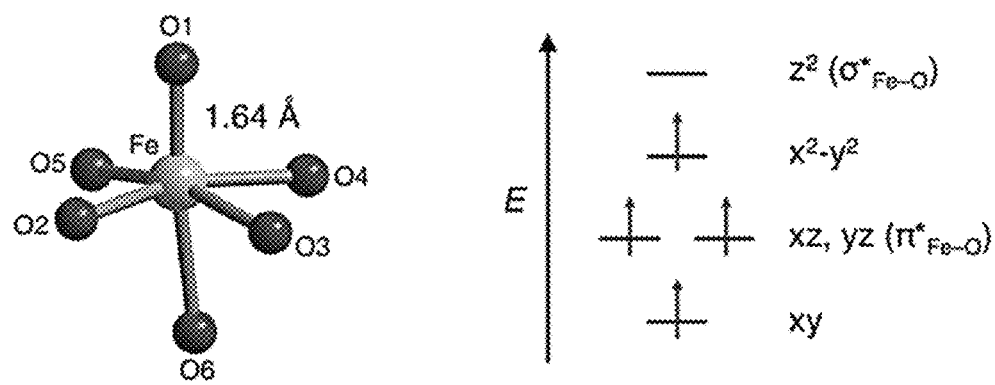
FIG. 26 provides a structure and qualitative molecular orbital (MO) diagram for $Fe_2(O)_2(dobdc)$. DFT and CASSCF/PT2 studies predict a short iron-oxo bond (1.64 Å) and a high-spin, S=2 spin ground state for iron(IV)-oxos installed in the $Fe_2(dobdc)$ framework. Selected interatomic distances (A) for 1: Fe—O1=1.638; Fe—O2=2.004; Fe—O3=2.127; Fe—O4=2.019; Fe—O5=2.054; Fe—O6=2.140.

As the high reactivity of the iron-oxo species precluded isolation in both $Fe_2$(dobdc) and its magnesium-diluted analog, electronic structure calculations were performed on $Fe_2(O)_2$(dobdc) (4) to gain insight into the geometric and electronic structure of iron-oxo units supported within the framework. First, periodic PBE+U geometry optimizations were performed on 4 for the singlet, triplet, and quintet spin states. A quintet ground state was predicted, with a short Fe—O bond length of 1.64 Å, consistent with that of previously reported iron(IV)-oxo complexes (see FIG. 26 and TABLE 14).

TABLE 14

Relative energies (kJ/mol)[a] and Mulliken atomic spin densities on Fe and O1[b] for 2 and 4. Full geometry optimizations were performed by periodic PBE + U for three possible spin states of each 2 and 4.

| Species | 2S | Spin density on Fe | Spin density on O1 | Fe—O1 Distance (Å) | Relative energy (kJ/(mol Fe))[a] |
|---|---|---|---|---|---|
| 2 | 1 | 1.09 | 0.00 | 1.81 | 149.5 |
|   | 3 | 3.34 | −0.15 | 1.87 | 61.7 |
|   | 5 | 4.31 | 0.23 | 1.84 | 0.0 |
| 4 | 0 | 0.00 | 0.00 | 1.64 | 113.9 |
|   | 2 | 1.51 | 0.46 | 1.62 | 76.7 |
|   | 4 | 3.42 | 0.33 | 1.64 | 0.0 |

[a]The lowest-energy spin state for each species has been taken as 0 reference.
[b]O1 is the terminal oxygen as shown in FIG. 27.

The periodic structure was then truncated to an 89-atom model cluster containing three metal centers, six organic linkers, and an oxo moiety to facilitate calculations using more accurate methods. The cluster calculations were simplified by replacing the two peripheral iron(II) centers with closed-shell zinc(II) centers, which have the same charge and a similar ionic radius to iron(II) and magnesium(II) cations (see FIG. 27). The geometry of this cluster was then optimized for the ground state, with all atoms except for the central iron and its first coordination sphere frozen at the coordinates from the periodic PBE+U optimization. As shown in TABLE 15, the M06 calculations also predict a quintet ground state.

TABLE 15

Calculated relative energies (kJ/mol) of the cluster model of 4.

| S | M06 | CASPT2 |
|---|---|---|
| 0 | 210.6 | 249.4 |
| 1 | 136.4 | 127.6 |
| 2 | 0.0 | 0.0 |

Further calculations were performed with several other exchange-correlation functionals, and in each case the ground state was found to be a quintet (see TABLES 16-20).

TABLE 16

Relative energies (kJ/mol)[a], S, $S^2$, and Mulliken spin densities on Fe and O1 for 2 and 4 cluster models. Single-point calculations were done on the 89- and 90-atom models using PBE/SDD(Fe, Zn), 6-311 + G(2df, p)(C, H, O)//PBE/SDD(Fe, Zn), 6-31G(d)(C, H, O).

| Species | State 2M$_s$ | Spin density S | $S^2$ | Fe | O1 | Relative energy (kJ/mol)[a] |
|---|---|---|---|---|---|---|
| 2 (cluster model) | 1 | 0.67 | 1.12 | 0.97 | 0.13 | 52.1 |
|  | 3 | 1.52 | 3.82 | 2.88 | 0.03 | 32.6 |
|  | 5 | 2.50 | 8.76 | 4.27 | 0.34 | 0.0 |
| 4 (cluster model) | 0 (open shell) | 0.79 | 1.42 | −0.08 | 0.07 | 88.4 |
|  | 2 | 1.06 | 2.20 | 1.57 | 0.73 | 54.4 |
|  | 4 | 2.01 | 6.06 | 3.08 | 0.60 | 0.0 |
|  | 6 | 3.01 | 12.01 | 3.97 | 1.16 | 104.8 |

[a]Relative energy is computed with respect to the most stable spin state.

TABLE 17

Relative energies (kJ/mol)[a], S, $S^2$, and Mulliken spin densities on Fe and O1 for 2 and 4 cluster models. Single-point calculations were done on the 89- and 90-atom models using M06/SDD(Fe, Zn), 6-311 + G(2df, p)(C, H, O)//M06-L/SDD(Fe, Zn), 6-31G(d)(C, H, O).

| Species | State 2M$_s$ | Spin density S | $S^2$ | Fe | O1 | Relative energy (kJ/mol)[a] |
|---|---|---|---|---|---|---|
| 2 (cluster model) | 1 | 0.85 | 1.56 | 1.05 | 0.04 | 218.5 |
|  | 3 | 1.53 | 3.87 | 3.11 | −0.13 | 109.6 |
|  | 5 | 2.50 | 8.76 | 4.30 | 0.30 | 0.0 |
| 4 (cluster model) | 0 (open shell) | 0.99 | 1.96 | 1.00 | −1.10 | 210.6 |
|  | 2 | 1.24 | 2.76 | 2.83 | −0.39 | 136.4 |
|  | 4 | 2.05 | 6.28 | 3.65 | 0.31 | 0.0 |
|  | 6 | 3.00 | 12.03 | 4.16 | 1.15 | 57.2 |

[a]Relative energy is computed with respect to the most stable spin state.

TABLE 18

Relative energies (kJ/mol)[a], S, $S^2$, and Mulliken spin densities on Fe and O1 for 2 and 4 cluster models. Single-point calculations were done on the 89- and 90-atom models using M08-SO/SDD(Fe, Zn), 6-311 + G(2df, p)(C, H, O)//M06-L/SDD(Fe, Zn), 6-31G(d)(C, H, O).

| Species | State 2M$_s$ | Spin density S | $S^2$ | Fe | O1 | Relative energy (kJ/mol)[a] |
|---|---|---|---|---|---|---|
| 2 (cluster model) | 1 | 1.01 | 2.02 | 1.02 | 0.01 | 115.8 |
|  | 3 | 1.51 | 3.79 | 2.98 | −0.07 | 82.5 |
|  | 5 | 2.50 | 8.76 | 4.37 | 0.33 | 0.0 |
| 4 (cluster model) | 0 (open shell) | 1.03 | 2.09 | −0.99 | 1.02 | 124.2 |
|  | 2 | 1.31 | 3.03 | 2.78 | −0.87 | 86.8 |
|  | 4 | 2.06 | 6.29 | 3.73 | 0.13 | 0.0 |
|  | 6 | 3.00 | 12.02 | 4.28 | 1.34 | 55.3 |

[a]Relative energy is computed with respect to the most stable spin state.

TABLE 19

Relative energies (kJ/mol)[a], S, S[2], and Mulliken spin densities on Fe and O1 for 2 and 4 cluster models. Single-point calculations were done on the 89- and 90-atom models using MPW1B95/SDD(Fe, Zn), 6-311 + G(2df, p)(C, H, O)//M06-L/SDD(Fe, Zn), 6-31G(d)(C, H, O).

| Species | State 2M$_s$ | Spin density S | S[2] | Fe | O1 | Relative energy (kJ/mol)[a] |
|---|---|---|---|---|---|---|
| 2 (cluster model) | 1 | 0.60 | 0.96 | 1.04 | 0.06 | 143.5 |
|  | 3 | 1.53 | 3.88 | 3.07 | −0.13 | 80.1 |
|  | 5 | 2.50 | 8.76 | 4.34 | 0.29 | 0.0 |
| 4 (cluster model) | 0 (open shell) | 0.80 | 1.44 | 0.72 | −0.61 | 141.7 |
|  | 2 | 1.24 | 2.79 | 2.87 | −0.58 | 96.1 |
|  | 4 | 2.06 | 6.29 | 3.69 | 0.14 | 0.0 |
|  | 6 | 3.00 | 12.02 | 4.21 | 1.20 | 45.3 |

[a]Relative energy is computed with respect to the most stable spin state.

TABLE 20

Relative energies (kJ/mol)[a], S, S[2], and Mulliken spin densities on Fe and O1 for 2 and 4 cluster models. Single-point calculations were done on the 89- and 90-atom models using PW6B95/SDD(Fe, Zn), 6-311 + G(2df, p)(C, H, O)//M06-L/SDD(Fe, Zn), 6-31G(d)(C, H, O).

| Species | State 2M$_s$ | Spin density S | S[2] | Fe | O1 | Relative energy (kJ/mol)[a] |
|---|---|---|---|---|---|---|
| 2 (cluster model) | 1 | 0.60 | 0.96 | 1.03 | 0.07 | 121.4 |
|  | 3 | 1.53 | 3.87 | 3.04 | −0.11 | 69.7 |
|  | 5 | 2.50 | 8.76 | 4.32 | 0.30 | 0.0 |
| 4 (cluster model) | 0 (open shell) | 0.80 | 1.43 | 0.64 | −0.54 | 126.8 |
|  | 2 | 1.23 | 2.74 | 2.79 | −0.43 | 87.4 |
|  | 4 | 2.05 | 6.25 | 3.61 | 0.25 | 0.0 |
|  | 6 | 3.00 | 12.03 | 4.18 | 1.17 | 50.3 |

[a]Relative energy is computed with respect to the most stable spin state.

Note that similar results were obtained when the Zn(II) centers in the 89-atom cluster were replaced with Mg(II) centers (see TABLES 21 and 22).

TABLE 21

Relative energies (kJ/mol)[a], S, S[2], and Mulliken spin densities on Fe and O1 for the cluster model of 4 and the cluster model of 4 with Zn(II) replacing Mg(II). All calculations were done using M06-L/SDD(Fe, Zn), 6-31G(d)(C, H, O, Mg)/opt6.

| Species | State 2M$_s$ | S | S[2] | Fe | O1 | Fe—O1 (Å) | Relative energy (kJ/mol)[a] |
|---|---|---|---|---|---|---|---|
| 4 (cluster model with Zn(II)) | 0 | 0.77 | 1.36 | 0.27 | −0.14 | 1.62 | 138.2 |
|  | 2 | 1.15 | 2.48 | 2.02 | 0.44 | 1.61 | 77.3 |
|  | 4 | 2.04 | 6.22 | 3.31 | 0.60 | 1.64 | 0.0 |
| 4 (cluster model with Mg(II)) | 0 | 0.78 | 1.40 | 0.26 | −0.11 | 1.62 | 138.7 |
|  | 2 | 1.17 | 2.55 | 2.18 | 0.34 | 1.60 | 71.9 |
|  | 4 | 2.06 | 6.29 | 3.35 | 0.61 | 1.64 | 0.0 |

[a]Relative energy is computed with respect to the most stable spin state.

TABLE 22

Relative energies (kJ/mol)[a], S, S[2], and Mulliken spin densities on Fe and O1 for the cluster model of 4 and the cluster model of 4 with Zn(II) replacing Mg(II). All calculations were done using M06/SDD(Fe, Zn), 6-31G(d)(C, H, O, Mg)/opt6.

| Species | State 2M$_s$ | Spin density S | S[2] | Fe | O1 | Fe—O1 (Å) | Relative energy (kJ/mol)[a] |
|---|---|---|---|---|---|---|---|
| 4 (cluster model with Zn(II)) | 0 | 0.86 | 1.60 | 0.41 | −0.47 | 1.58 | 213.3 |
|  | 2 | 1.27 | 2.90 | 2.90 | −0.32 | 1.62 | 132.1 |
|  | 4 | 2.05 | 6.27 | 3.54 | 0.42 | 1.63 | 0.0 |
| 4 (cluster model with Mg(II)) | 0 | 0.91 | 1.73 | −0.60 | 0.58 | 1.59 | 215.6 |
|  | 2 | 1.29 | 2.97 | 2.91 | −0.24 | 1.62 | 125.0 |
|  | 4 | 2.07 | 6.38 | 3.61 | 0.46 | 1.64 | 0.0 |

[a]Relative energy is computed with respect to the most stable spin state.

The electronic structure of the cluster model of 4 was further examined with single-point multi-configurational complete active space (CASSCF) calculations followed by second-order perturbation theory (CASPT2). Again, the ground state was predicted to be the quintet state (see TABLE 15 and TABLE 23).

TABLE 23

State energy splitting of 2 and 4 cluster models calculated by CASSCF and CASPT2.

| Species | 2M$_s$ | Largest CASSCF configuration weight | M[a] | Relative CASSCF energy (kJ/mol) | Relative CASPT2 energy (kJ/mol) |
|---|---|---|---|---|---|
| 2 (cluster model) | 1 | 94% | 0.102 | 328.4 | 294.6 |
|  | 3 | 79% | 0.309 | 216.7 | 145.2 |
|  | 5 | 100% | 0.000 | 0.0 | 0.0 |
| 4 (cluster model) | 0 (open shell) | 77% | 0.272 | 210.5 | 249.4 |
|  | 2 | 74% | 0.306 | 139.3 | 127.6 |
|  | 4 | 77% | 0.311 | 0.0 | 0.0 |

[a]M is a diagnostic used to quantify the extent of multi-reference character of the system, and it is defined to be $$M = \frac{1}{2}\left(2 - n(MCDONO) + \sum_{j=1}^{n_{SOMO}} |n(j) - 1| + n(MCUNO)\right)$$

where n(MCDONC), n$_{SOMO}$, and n(MCUNC) are the most correlated doubly occupied natural orbital, a singly occupied natural orbital, and the most correlating unoccupied natural orbital, respectively.

Both M06 and CASPT2 yield a spin density of 3.7 on iron, consistent with four unpaired spins mainly localized on the metal (see TABLE 17 and TABLE 24).

TABLE 24

Charge and spin densities of the sextet and quintet ground spin states of the cluster models of 2 and 4 from CASSCF calculations.

|  | 2 (cluster model) | | 4 (cluster model) | |
|---|---|---|---|---|
|  | Fe | O1 | Fe | O1 |
| CASSCF Mulliken Spin Density | 4.79 | 0.07 | 3.744 | 0.173 |
| CASSCF Mulliken Charge Density | 1.95 | −0.77 | 1.765 | −0.419 |
| CASSCF LoProp Charge Density | 2.21 | −1.09 | 1.963 | −0.559 |

Density functional and CASPT2 calculations were also performed on the cluster model of 2; all calculations led to a high-spin sextet ground state for the iron(III) center (see TABLES 16-20 and Table 23).

A number of embodiments have been described herein. Nevertheless, it will be understood that various modifications may be made without departing from the spirit and scope of this disclosure. Accordingly, other embodiments are within the scope of the following claims.

What is claimed is:

1. A method of oxidizing a molecule or compound, comprising contacting the molecule or compound with a metal organic framework (MOF) and a terminal oxidant of $N_2O$, wherein the MOF comprises a plurality of redox-active metals or metal ions connected by a plurality of organic linking ligands comprising the structure(s) selected from the group consisting of:

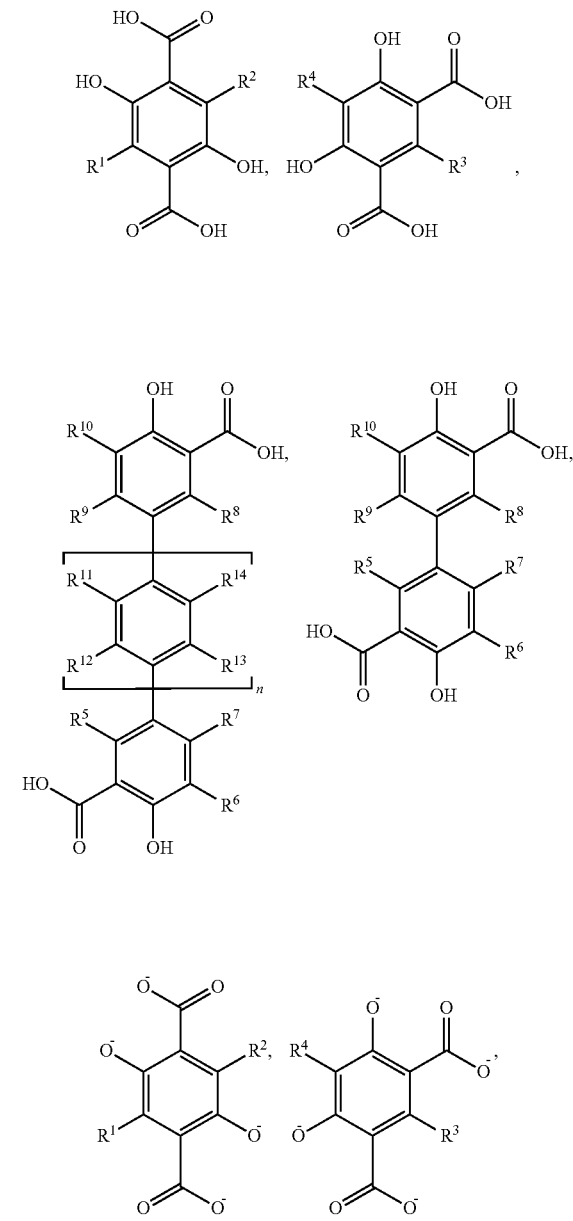

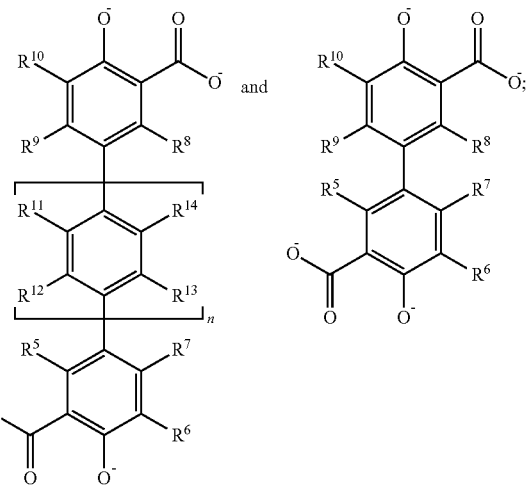

wherein $R^1$-$R^{14}$ are independently selected from H, D, halo, optionally substituted FG, optionally substituted ($C_1$-$C_{20}$) alkyl, optionally substituted ($C_1$-$C_{19}$)heteroalkyl, optionally substituted ($C_1$-$C_{20}$)alkenyl, optionally substituted ($C_1$-$C_{19}$) heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, or optionally substituted heterocycle, optionally substituted mixed ring system, wherein one or more adjacent R groups can be linked together to form one or more substituted rings selected from the group consisting of cycloalkyl, cycloalkenyl, heterocycle, aryl, and mixed ring system; wherein, the MOF is capable of catalytically oxidizing of small hydrocarbons to their corresponding alcohols and aldehydes.

2. The method of claim 1, wherein the molecule or compound is a $C_1$-$C_6$ alkane, a $C_1$-$C_6$ alkene, a $C_1$-$C_6$ alkyne, benzene, or a $C_3$-$C_6$ cycloalkyl.

3. The method of claim 2, wherein the $C_1$-$C_6$ alkane is converted to a corresponding $C_1$-$C_6$ alcohol or $C_1$-$C_6$ aldehyde.

4. The method of claim 3, wherein the $C_1$-$C_6$ alkane is selectively converted to the $C_1$-$C_6$ alcohol versus the $C_1$-$C_6$ aldehyde in a ratio of 25:1.

5. The method of claim 2, wherein the $C_1$-$C_6$ alkene is converted to a $C_1$-$C_6$ corresponding epoxide.

6. The method of claim 2, wherein cyclohexane is converted into a mixture of cyclohexanol and cyclohexanone (KA oil).

7. The method of claim 1, wherein the organic linking ligand comprises a structure selected from the group consisting of:

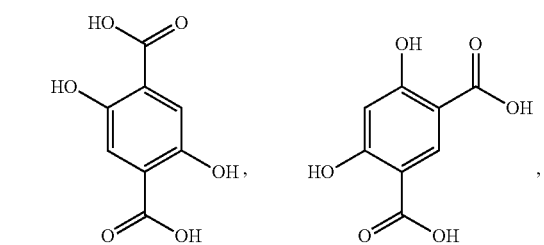

-continued

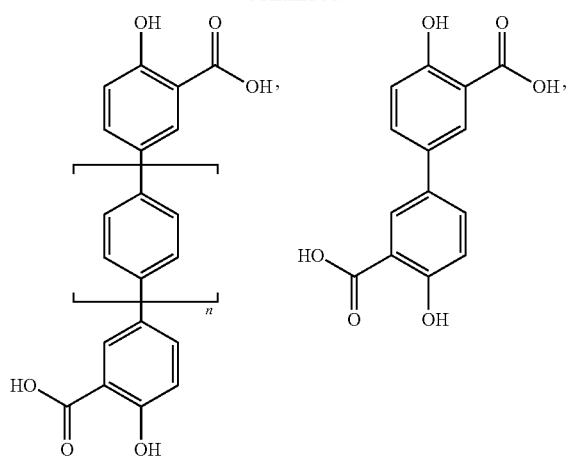

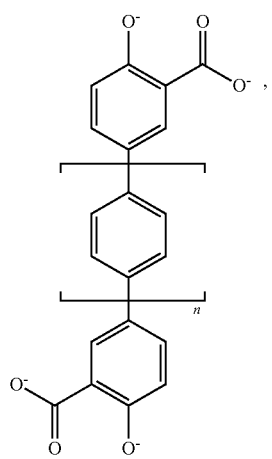

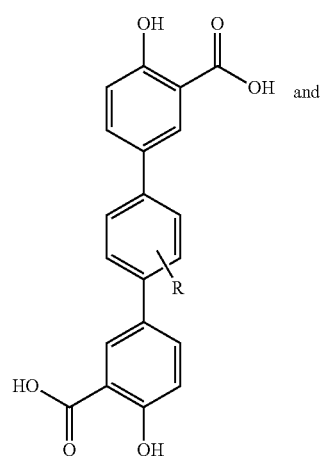

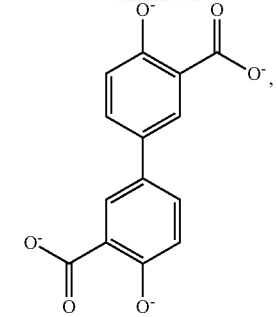

wherein

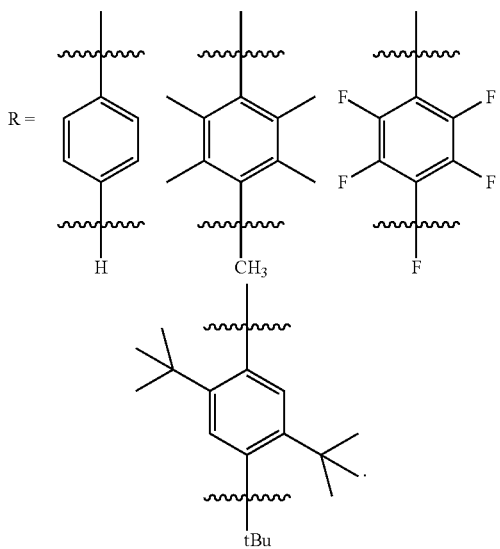

8. The method of claim 1, wherein the organic linking ligand is selected from:

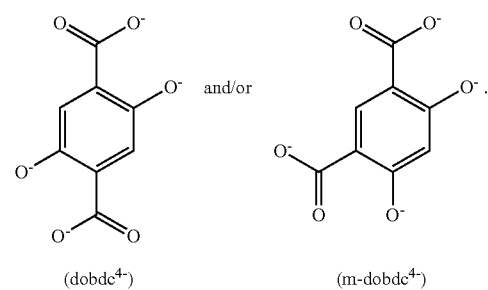 [SMILES: O=C([O-])c1cc([O-])c(C(=O)[O-])cc1[O-] ; O=C([O-])c1cc(C(=O)[O-])c([O-])cc1[O-]]

(dobdc$^{4-}$)   (m-dobdc$^{4-}$)

9. The method of claim 1, wherein the MOF comprises repeating units of the formula $(M^1)_2$(dobdc), of the formula $(M^1)_2$(m-dobdc) and/or of the formula $(M^1)_2(H_4\text{dotpdc}^R)$, wherein $M^1$ is a redox-active metal or metal ion.

10. The method of claim 1, wherein the redox-active metal is selected from the group consisting of Fe, Mn, Co, Ni, Cu, and a divalent cation of any of the foregoing.

11. The method of claim 1, wherein the MOF is a mixed metal MOF and comprises a plurality of redox-active metal ions and a plurality of redox-inactive metal ions.

12. The method of claim 11, wherein the plurality of redox-inactive metal ions is selected from the group consisting of Mg, Ca, Sr, Ba, Sc, Y, Ti, Zr, V, Nb, Ta, Cr, Mo, W, Re, Ru, Os, Rh, Ir, Pd, Pt, Ag, Au, Zn, Cd, Hg, Al, Ga, In, Si, Ge, Sn, Pb, As, Te, La, Ce, Pr, Nd, Sm, Eu, Gd, Tb, Db, Tm, Yb, La, and a divalent cation of any of the foregoing.

13. The method of claim 1, wherein the MOF comprises repeating units of the formula $(M^1)_x(M^2)_{2-x}(dobdc)$, of the formula $(M^1)_x(M^2)_{2-x}(m\text{-}dobdc)$ and/or of the formula $(M^1)_x(M^2)_{2-x}(H_4 dotpdc^R)$, wherein at least one of $M^1$-$M^2$ is a redox-active metal or metal ion, x is a number less than or equal to 1.

14. The method of claim 1, wherein the MOF comprises repeating units of the formula $(M^1)_x(M^2)_{2-x}(dobdc)$, of the formula $M^1_x(M^2)_{2-x}(m\text{-}dobdc)$ and/or of the formula $(M^1)_x(M^2)_{2-x}(H_4 dotpdc^R)$ wherein at least one of $M^1$-$M^2$ is a redox-active metal or metal ion, x is a number less than or equal to 0.3.

15. The method of claim 1, wherein the MOF comprises repeating units of the formula $(M^1)_x(M^2)_{2-x}(dobdc)$, of the formula $M^1_x(M^2)_{2-x}(m\text{-}dobdc)$ and/or of the formula $(M^1)_x(M^2)_{2-x}(H_4 dotpdc^R)$ wherein at least one of $M^1$-$M^2$ is a redox-active metal or metal ion, x is a number less than or equal to 0.1.

16. The method of claim 13, wherein $M^1$ is selected from the group consisting of Fe, Mn, Co, Ni, Cu, and a divalent cation of any of the foregoing, and $M^2$ is selected from the group consisting of Mg, Ca, Sr, Ba, Sc, Y, Ti, Zr, V, Nb, Ta, Cr, Mo, W, Re, Ru, Os, Rh, Ir, Pd, Pt, Ag, Au, Zn, Cd, Hg, Al, Ga, In, Si, Ge, Sn, Pb, As, Te, La, Ce, Pr, Nd, Sm, Eu, Gd, Tb, Db, Tm, Yb, La, and a divalent cation of any of the foregoing.

17. The method of claim 1, wherein the MOF is reacted with $N_2O$ at a temperature of about 75° C. and at a pressure between 1 to 10 bar.

* * * * *